US011377658B2

(12) United States Patent
Gottesman et al.

(10) Patent No.: US 11,377,658 B2
(45) Date of Patent: Jul. 5, 2022

(54) OLIGONUCLEOTIDES FOR TREATMENT OF ANGIOPOIETIN LIKE 4 (ANGPTL4) RELATED DISEASES

(71) Applicant: EMPIRICO INC., San Diego, CA (US)

(72) Inventors: Omri Gottesman, San Diego, CA (US); Shannon Bruse, San Diego, CA (US); Brian Cajes, San Diego, CA (US); David Lewis, Madison, WI (US); David Rozema, Cross Plains, WI (US)

(73) Assignee: EMPIRICO INC., San Diego, CA (US)

(*) Notice: Subject to any disclaimer, the term of this patent is extended or adjusted under 35 U.S.C. 154(b) by 0 days.

(21) Appl. No.: 17/476,317

(22) Filed: Sep. 15, 2021

(65) Prior Publication Data

US 2022/0002731 A1     Jan. 6, 2022

Related U.S. Application Data

(63) Continuation of application No. PCT/US2020/063824, filed on Dec. 8, 2020.

(60) Provisional application No. 62/945,732, filed on Dec. 9, 2019.

(51) Int. Cl.
C12N 15/113      (2010.01)

(52) U.S. Cl.
CPC ...... *C12N 15/1136* (2013.01); *C12N 2310/14* (2013.01); *C12N 2310/315* (2013.01); *C12N 2310/321* (2013.01); *C12N 2310/322* (2013.01); *C12N 2310/351* (2013.01)

(58) Field of Classification Search
None
See application file for complete search history.

(56) References Cited

U.S. PATENT DOCUMENTS

| 7,691,997 B2* | 4/2010 | Khvorova ......... G16B 20/50 536/24.5 |
| 9,352,048 B2 | 5/2016 | Manoharan et al. |
| 2007/0054856 A1 | 3/2007 | Gerber et al. |
| 2010/0172915 A1 | 7/2010 | Gerber et al. |
| 2012/0035115 A1 | 2/2012 | Manoharan et al. |
| 2012/0207770 A1 | 8/2012 | Tan et al. |
| 2019/0038768 A1 | 2/2019 | Rajeev et al. |
| 2019/0202855 A1 | 7/2019 | Sakamuri et al. |

FOREIGN PATENT DOCUMENTS

| WO | WO-2015069932 A1 | 5/2015 |
| WO | WO-2015188197 A2 | 12/2015 |
| WO | WO-2018002719 A1 | 1/2018 |
| WO | WO-2019053661 A2 | 3/2019 |
| WO | WO-2019217527 A1 | 11/2019 |
| WO | WO-2021119019 A1 | 6/2021 |

OTHER PUBLICATIONS

ANGPTL4 siRNAs available for purchase from Thermo Fisher and other vendors. Santa Cruz Technology Inc. (2020).
Aryal et al., ANGPTL4 in metabolic and cardiovascular disease. Trends in Molecular Medicine 25(8):723-734 (2019).
Hsieh et al.: Epigenetic silencing of the dual-role signal mediator, ANGPTL4 in tumortissues and its overexpression in the urothelial carcinoma microenvironment. Oncogene 37(5):673-686 (2018) Epub 2017.
PCT/US2020/063824 International Invitation to Pay Additional Fees dated Mar. 15, 2021.
PCT/US2020/063824 International Search Report and Written Opinion dated May 6, 2021.

* cited by examiner

*Primary Examiner* — Tracy Vivlemore
(74) *Attorney, Agent, or Firm* — Wilson Sonsini Goodrich & Rosati

(57) ABSTRACT

Provided are compositions comprising an oligonucleotide that targets Angiopoietin-like 4 (ANGPTL4). The oligonucleotide may include a small interfering RNA (siRNA) or an antisense oligonucleotide (ASO). Also provided herein are methods of treating a metabolic or cardiovascular disorder by providing an oligonucleotide that targets ANGPTL4 to a subject in need thereof.

20 Claims, No Drawings

Specification includes a Sequence Listing.

OLIGONUCLEOTIDES FOR TREATMENT OF ANGIOPOIETIN LIKE 4 (ANGPTL4) RELATED DISEASES

CROSS-REFERENCE

The present application is a continuation of International Patent Application No. PCT/US2020/063824, filed Dec. 8, 2020, which claims the benefit of U.S. Provisional Application No. 62/945,732 filed Dec. 9, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 15, 2021, is named 54462-712_301_SL.txt and is 4,087,518 bytes in size.

BACKGROUND

Cardiovascular and metabolic disorders are becoming increasingly abundant, and may affect a wide variety of persons. Improved therapeutics are needed for treating these disorders.

SUMMARY

Disclosed herein, in some embodiments, are compositions comprising an oligonucleotide that targets Angiopoietin-like 4 (ANGPTL4) and when administered to a subject in an effective amount decreases circulating triglycerides, decreases circulating glucose, increases circulating high-density lipoproteins (HDL), or increases insulin sensitivity, wherein the oligonucleotide comprises a small interfering RNA (siRNA) comprising a sense strand and an antisense strand, the antisense strand being complementary with no more than 2 mismatches to a portion of a nucleic acid having the nucleoside sequence of SEQ ID NO: 13935, and each strand having 12 to 30 nucleotides. In some embodiments, the triglycerides, total cholesterol, or glucose is decreased by about 10% or more, or the HDL or insulin sensitivity is increased by about 10% or more, as compared to prior to administration. In some embodiments, the antisense strand is complementary with no more than 2 mismatches to a portion of a nucleic acid having the nucleoside sequence of SEQ ID NO: 13936. In some embodiments, the antisense strand comprises a nucleoside sequence at least 85% identical to an antisense strand sequence of an siRNA in Table 4. In some embodiments, the antisense strand comprises the nucleoside sequence of an antisense strand sequence of an siRNA in Table 4, or an antisense strand sequence thereof having 1 or 2 nucleoside substitutions, additions, or deletions. In some embodiments, the antisense strand comprises the nucleoside sequence of an antisense strand sequence of an siRNA in Table 4. In some embodiments, the sense strand comprises a nucleoside sequence at least 85% identical to the sense strand sequence of the siRNA in Table 4. In some embodiments, the sense strand comprises the nucleoside sequence of the sense strand sequence of the siRNA in Table 4, or a sense strand sequence thereof having 1 or 2 nucleoside substitutions, additions, or deletions. In some embodiments, the sense strand comprises the nucleoside sequence of the sense strand sequence of the siRNA in Table 4. In some embodiments, the antisense strand comprises a nucleoside sequence at least 85% identical to SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696. In some embodiments, the antisense strand comprises the nucleoside sequence of SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or an antisense strand sequence thereof having 1 or 2 nucleoside substitutions, additions, or deletions. In some embodiments, the antisense strand comprises the nucleoside sequence of SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696. In some embodiments, the sense strand comprises a nucleoside sequence at least 85% identical to SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842. In some embodiments, the sense strand comprises the nucleoside sequence of SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, or a sense strand sequence thereof having 1 or 2 nucleoside substitutions, additions, or deletions. In some embodiments, the sense strand comprises the nucleoside sequence of SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842. In some embodiments, the antisense strand comprises a nucleoside sequence at least 85% identical to any of SEQ ID NOS: 13978-13981. In some embodiments, the antisense strand comprises the nucleoside sequence of any of SEQ ID NOS: 13978-13981, or an antisense strand sequence thereof having 1 or 2 nucleoside substitutions, additions, or deletions. In some embodiments, the antisense strand comprises the nucleoside sequence of any of SEQ ID NOS: 13978-13981. In some embodiments, the sense strand comprises a nucleoside sequence at least 85% identical to any of SEQ ID NOS: 13970-13973. In some embodiments, the sense strand comprises the nucleoside sequence of any of SEQ ID NOS: 13970-13973, or a sense strand sequence thereof having 1 or 2 nucleoside substitutions, additions, or deletions. In some embodiments, the sense strand comprises the nucleoside sequence of any of SEQ ID NOS: 13970-13973. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises a phosphorothioate linkage. In some embodiments, the sense strand comprises 2-6 modified internucleoside linkages. In some embodiments, the antisense strand comprises 2-6 modified internucleoside linkages. In some embodiments, the oligonucleotide comprises a modified nucleoside. In some embodiments, the modified nucleoside comprise a locked nucleic acid (LNA), hexitol nucleic acid (HLA), cyclohexene nucleic acid (CeNA), a 2',4' constrained ethyl, 2'-methoxyethyl, 2'-O-alkyl, 2'-O-allyl, 2'-O-allyl, 2'-fluoro, 2'-deoxy, a 2' 0 methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, 2' ara-F, or a combination thereof. In some embodiments, the modified nucleoside comprises a 2' fluoro modified nucleoside. In some embodiments, the modified nucleoside comprises a 2' 0 methyl modified nucleoside. In some embodiments, the sense strand or antisense strand comprises 15-21 modified nucleosides. In some embodiments, the sense strand or the antisense strand comprises a 3' overhang of at least 2 nucleosides. In some embodiments, the oligonucleotide comprises a GalNAc ligand attached at a 3' or 5' terminus of the sense strand. In some embodiments, the oligonucleotide comprises a GalNAc ligand attached at a 3' or 5' terminus of the antisense strand In some embodiments, the sense strand comprises modification pattern 1S: 5' NfsnsNfnNfnNfNfNfnNfnNfnNfnNfnNfnNfsnsn-3' (SEQ ID NO: 13954), modification pattern 2S: 5' nsnsnnNfnNfNfN fnnnnnnnnnnnsnsn-3' (SEQ ID NO: 13955), modification pattern 3S: 5' nsnsnnNfnNfnNfnnnnnnnnnnnsnsn-3' (SEQ ID NO: 13956), modification pattern 4S: 5' NfsnsNfnNfnNfN fNfnNfnNfnNfnNfnNfsnsnN-3' (SEQ ID NO: 13957), modification pattern 5S: 5'-nsnsnnNfnNfNfN fnnnnnnnnnnnsnsnN-3' (SEQ ID NO: 13958); modification pattern 6S: 5' NfsnsNfnNfnNfnNfnNfnNfnNfnNfnNfsnsn 3' (SEQ ID NO: 13959); wherein "Nf" is a 2' fluoro-modified nucleoside, "n" is a 2' O-methyl modified nucleoside, "s" is a phosphorothioate linkage, and N comprises a nucleoside. In some embodiments, the antisense strand comprises modification pattern 1AS: 5' nsNfsnNfnNfnNfn NfnnnNfnNfnNfnsnsn-3' (SEQ ID NO: 13960), modification pattern 2AS: 5' nsNfsnnnNfnNfNfnnnnNfnNfnnnsnsn-3' (SEQ ID NO: 13961), modification pattern 3AS: 5' nsNfsnnnNfnnnnnnnNfnNfnnnsnsn-3' (SEQ ID NO: 13962), modification pattern 4AS: 5' nsNfsnNfnNf nnnnnnnNfnNfnnnsnsn 3' (SEQ ID NO: 13963), modification pattern 5AS: 5' nsNfsnnnNfnNfnnnnnNfnNfnnnsnsn 3' (SEQ ID NO: 13964), modification pattern 6AS: 5' nsNfsnNfnNfnNfnNfnNfnNfnNfnNfnsnsn 3' (SEQ ID NO: 13965), modification pattern 7AS: 5' nsNfsnNfnNfnNf NfnnnnNfnNfnnnsnsn 3' (SEQ ID NO: 13966), modification pattern 8AS: 5' nsNfsnnnnnnnnnnnNfnNfnnnsnsn 3' (SEQ ID NO: 13967), or modification pattern 9AS: 5' nsNfsnnnNfnnnnnnnnNfnNfnNfnsnsn 3' (SEQ ID NO: 13968); wherein "Nf" is a 2' fluoro-modified nucleoside, "n" is a 2' O-methyl modified nucleoside, and "s" is a phosphorothioate linkage. In some embodiments, the composition is a pharmaceutical composition comprising a pharmaceutically acceptable carrier. In some embodiments, the pharmaceutically acceptable carrier comprises water, a buffer, or a saline solution.

Disclosed herein, are methods of treating a metabolic or cardiovascular disorder in a subject in need thereof, the method comprising administering to the subject an effective amount of a composition comprising an oligonucleotide that targets ANGPTL4, wherein the oligonucleotide comprises a small interfering RNA (siRNA) comprising a sense strand and an antisense strand, the antisense strand being complementary with no more than 2 mismatches to a portion of a nucleic acid having the nucleoside sequence of SEQ ID NO: 13936, and each strand having 12 to 30 nucleotides. In some embodiments, the disorder comprises hyperlipidemia, hypertriglyceridemia, pancreatitis, familial chylomicronemia syndrome, diabetes, type 2 diabetes, heart disease, a myocardial infarction, angina pectoris, or atherosclerosis. In some embodiments, the effective amount of the composition decreases a triglyceride measurement, decreases a cholesterol measurement, decreases a glucose measurement, increases an HDL measurement, or increases an insulin sensitivity measurement in the subject by about 10% or more, relative to a baseline measurement. In some embodiments, the antisense strand is complementary with no more than 2 mismatches to a portion of a nucleic acid having the nucleoside sequence of SEQ ID NO: 13935. In some embodiments, the antisense strand comprises a nucleoside sequence at least 85% identical to SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696. In some embodiments, the antisense strand comprises the nucleoside sequence of SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or an antisense strand sequence thereof having 1 or 2 nucleoside substitutions, additions, or deletions. In some embodiments, the antisense strand comprises the nucleoside sequence of SEQ ID NO: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696. In some embodiments, the sense strand comprises a nucleoside sequence at least 85% identical to SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842. In some embodiments, the sense strand comprises the nucleoside sequence of SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, or a sense strand sequence thereof having 1 or 2 nucleoside substitutions, additions, or deletions. In some embodiments, the sense strand comprises the nucleoside sequence of SEQ ID NO: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842. In some embodiments, the antisense strand comprises a nucleoside sequence at least 85% identical to any of SEQ ID NOS: 13978-13981. In some embodiments, the antisense strand comprises the nucleoside sequence of any of SEQ ID NOS: 13978-13981, or an antisense strand sequence thereof having 1 or 2 nucleoside substitutions, additions, or deletions. In some embodiments, the antisense strand comprises the nucleoside sequence of any of SEQ ID NOS: 13978-13981. In some embodiments, the sense strand comprises a nucleoside sequence at least 85% identical to any of SEQ ID NOS: 13970-13973. In some embodiments, the sense strand comprises the nucleoside sequence of any of SEQ ID NOS: 13970-13973, or a sense strand sequence thereof having 1 or 2 nucleoside substitutions, additions, or deletions. In some embodiments, the sense strand comprises the nucleoside sequence of any of SEQ ID NOS: 13970-13973. In some embodiments, the oligonucleotide comprises a modified internucleoside linkage comprising: alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the oligonucleotide comprises a modified nucleoside comprising: a locked nucleic acid (LNA), hexitol nucleic acid (HLA), cyclohexene nucleic acid (CeNA), a 2',4' constrained ethyl, 2'-methoxyethyl, 2'-O-alkyl, 2'-O-allyl, 2'-O-allyl, 2'-fluoro, 2'-deoxy, a 2' 0 methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, 2' ara-F, or a combination thereof. In some embodiments, the sense strand or the antisense strand comprises a 3' overhang of at least 2 nucleosides. In some embodiments, the oligonucleotide comprises a GalNAc ligand attached at a 3' or 5' terminus of the sense strand. In some embodiments, the oligonucleotide comprises a GalNAc ligand attached at a 3' or 5' terminus of the antisense strand In some embodiments, the sense strand comprises modification pattern 1S: 5' NfsnsNfnNfnNfnNfnNfnNfnNfnNfnNfnNfsnsn-3' (SEQ ID NO: 13954), modification pattern 2S: 5' nsnsnnNfnNfNfNfnnnnnnnnnnsnsn-3' (SEQ ID NO: 13955), modification pattern 3S: 5' nsnsnnNfn NfnNfnnnnnnnnnsnsn-3' (SEQ ID NO: 13956), modification pattern 4S: 5' NfsnsNfnNfnNfNfNfnNfnNfn NfnNfnNfsnsnN-3' (SEQ ID NO: 13957), modification pattern 5S: 5'-nsnsnnNfnNfNfNfnnnnnnnnnsnsnN-3' (SEQ ID NO: 13958); modification pattern 6S: 5' NfsnsNfn NfnNfnNfnNfnNfnNfnNfnNfsnsn 3' (SEQ ID NO: 13959); wherein "Nf" is a 2' fluoro-modified nucleoside, "n" is a 2' O-methyl modified nucleoside, "s" is a phosphorothioate linkage, and N comprises a nucleoside. In some embodiments, the antisense strand comprises modification pattern 1AS: 5' nsNfsnNfnNfnNfnNfnNfnnnNfnNfnNfsnsn-3' (SEQ ID NO: 13960), modification pattern 2AS: 5' nsNfsnnnN fnNfNfnnnnNfnNfnnnsnsn-3' (SEQ ID NO: 13961), modification pattern 3AS: 5' nsNfsnnnNfnnnnnnnNfnNfnnnsnsn-3' (SEQ ID NO: 13962), modification pattern 4AS: 5' nsNfsnNfnNfnnnnnnnnNfnNfnnnsnsn 3' (SEQ ID NO: 13963), modification pattern 5AS: 5' nsNfsnnnNfn NfnnnnnNfnNfnnnsnsn 3' (SEQ ID NO: 13964), modification pattern 6AS: 5' nsNfsnNfnNfnNfnN fnNfnNfnNfnNfsnsn 3' (SEQ ID NO: 13965), modification pattern 7AS: 5' nsNfsnNfnNfnNfNfnnnnNfnNfnnnsnsn 3' (SEQ ID NO: 13966), modification pattern 8AS: 5' nsNfsnnnnnnnnnnnNfnnnnnsnsn 3' (SEQ ID NO: 13967), or modification pattern 9AS: 5' nsNfsnnnNfnnn nnnnNfnNfnNfsnsn 3' (SEQ ID NO: 13968); wherein "Nf" is a 2' fluoro-modified nucleoside, "n" is a 2' O-methyl modified nucleoside, and "s" is a phosphorothioate linkage.

Disclosed herein are compositions comprising an oligonucleotide that targets Angiopoietin-like 4 (ANGPTL4) and when administered to a subject in an effective amount decreases circulating triglycerides. In some embodiments, the triglycerides are decreased by about 10% or more, as compared to prior to administration. Also disclosed herein are compositions comprising an oligonucleotide that targets ANGPTL4 and when administered to a subject in an effective amount decreases circulating total cholesterol. In some embodiments, the total cholesterol is decreased by about 10% or more, as compared to prior to administration. Also disclosed herein are compositions comprising an oligonucleotide that targets ANGPTL4 and when administered to a subject in an effective amount increases circulating high-density lipoproteins (HDL). In some embodiments, the HDL are increased by about 10% or more, as compared to prior to administration. Also disclosed herein are compositions comprising an oligonucleotide that targets ANGPTL4 and when administered to a subject in an effective amount decreases circulating glucose. In some embodiments, the glucose is decreased by about 10% or more, as compared to prior to administration. Also disclosed herein are compositions comprising an oligonucleotide that targets ANGPTL4 and when administered to a subject in an effective amount increases insulin sensitivity. In some embodiments, the insulin sensitivity is increased by about 10% or more, as compared to prior to administration. In some embodiments, the oligonucleotide comprises a small interfering RNA (siRNA) comprising a sense strand and an antisense strand. In some embodiments, the sense strand is 14-30 nucleosides in length. In some embodiments, the antisense strand is 14-30 nucleosides in length. Also disclosed herein are compositions comprising an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13935. Also disclosed herein are compositions comprising an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13936. In some embodiments, the sense strand and the antisense strand form a double-stranded RNA duplex. In some embodiments, the first base pair of the double-stranded RNA duplex is an AU base pair. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions. In some embodiments, the sense strand comprises a nucleoside sequence comprising or consisting of the sequence of any one of SEQ ID NOs: 1-1854 or 13970-13977. In some embodiments, the sense strand further comprises a 3' overhang comprising 1, 2, or more nucleosides. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions. In some embodiments, the antisense strand comprises a nucleoside sequence comprising or consisting of the sequence of any one of SEQ ID NOs: 1855-3708 or 13978-13985. In some embodiments, the antisense strand further comprises a 3' overhang comprising 1, 2, or more nucleosides. In some embodiments, the siRNA binds with a 19mer in a human ANGPTL4 mRNA. In some embodiments, the siRNA binds with a 17mer in a non-human primate ANGPTL4 mRNA. In some embodiments, the siRNA binds with a 19mer in a human ANGPTL4 mRNA. In some embodiments, the siRNA binds with a human ANGPTL4 mRNA and less than or equal to 20 human off-targets, with no more than 2 mismatches in the antisense strand. In some embodiments, siRNA binds with a human ANGPTL4 mRNA target site that does not harbor an SNP, with a minor allele frequency (MAF) greater or equal to 1% (pos. 2-18). In some embodiments, the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside substitutions, additions, or deletions. In some embodiments, the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside substitutions, additions, or deletions. In some embodiments, the sense strand comprises the nucleoside sequence of any one of SEQ ID NO: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803. In some embodiments, the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657. In some embodiments, the sense strand comprises the nucleoside sequence of any one of SEQ ID NOs: 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, or 1787, or a nucleic acid sequence thereof having 1 or 2 nucleoside substitutions, additions, or deletions. In some embodiments, the antisense strand comprises the nucleoside sequence of any one of SEQ ID NOs: 1887, 1888, 1889, 1890, 1910, 1975, 2126, 2134, 2136, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2335, 2338, 2363, 2371, 2373, 2374, 2419, 2474, 2489, 2491, 2494, 2684, 2688, 2695, 2696, 2697, 2698, 2704, 2725, 2726, 2730, 2741, 2742, 2748, 2751, 2756, 2799, 2855, 2856, 2859, 2891, 2987, 2988, 2991, 3003, 3005, 3007, 3008, 3009, 3011, 3012, 3015, 3016, 3018, 3019, 3020, 3025, 3026, 3102, 3103, 3169, 3192, 3197, 3201, 3202, 3283, 3284, 3424, 3425, 3426, 3464, 3465, 3471, 3634, 3638, or 3641, or a nucleic acid sequence thereof having 1 or 2 nucleoside substitutions, additions, or deletions. In some embodiments, the sense strand comprises the nucleoside sequence of any one of SEQ ID NOs: 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, or 1803, or a nucleic acid sequence thereof having 1 or 2 nucleoside substitutions, additions, or deletions. In some embodiments, the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1966, 1970, 1971, 1972, 1973, 1974, 1979, 1980, 1981, 1982, 1983, 2003, 2004, 2006, 2007, 2011, 2012, 2013, 2015, 2018, 2019, 2020, 2021, 2022, 2023, 2026, 2028, 2029, 2050, 2053, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2234, 2236, 2240, 2242, 2245, 2246, 2247, 2248, 2251, 2252, 2253, 2256, 2258, 2259, 2265, 2266, 2267, 2268, 2269, 2274, 2275, 2276, 2277, 2278, 2279, 2280, 2281, 2282, 2283, 2284, 2285, 2289, 2338, 2371, 2373, 2374, 2419, 2424, 2425, 2426, 2461, 2462, 2464, 2465, 2466, 2470, 2471, 2474, 2489, 2491, 2494, 2526, 2527, 2528, 2529, 2530, 2531, 2532, 2533, 2535, 2536, 2537, 2538, 2540, 2541, 2543, 2546, 2549, 2684, 2695, 2696, 2697, 2698, 2704, 2705, 2706, 2707, 2708, 2710, 2711, 2720, 2722, 2725, 2726, 2730, 2741, 2742, 2744, 2746, 2747, 2748, 2756, 2765, 2766, 2767, 2768, 2769, 2770, 2771, 2772, 2773, 2774, 2775, 2776, 2799, 2855, 2856, 2859, 2860, 2863, 2864, 2865, 2867, 2882, 2886, 2906, 2907, 2908, 2909, 2911, 2912, 2966, 2976, 2978, 2980, 2981, 2987, 2988, 3001, 3002, 3003, 3005, 3007, 3008, 3009, 3011, 3012, 3015, 3016, 3018, 3019, 3020, 3029, 3036, 3038, 3106, 3107, 3113, 3130, 3139, 3164, 3169, 3197, 3201, 3202, 3203, 3204, 3205, 3259, 3261, 3267, 3268, 3269, 3270, 3271, 3272, 3283, 3284, 3302, 3373, 3377, 3410, 3415, 3417, 3418, 3419, 3425, 3426, 3434, 3435, 3443, 3451, 3455, 3456, 3457, 3458, 3459, 3460, 3465, 3467, 3468, 3547, 3553, 3555, 3556, 3557, 3576, 3594, 3595, 3596, 3599, 3601, 3602, 3603, 3605, 3608, 3609, 3633, 3634, 3638, 3642, 3652, 3653, 3655, 3656, or 3657, or a nucleic acid sequence thereof having 1 or 2 nucleoside substitutions, additions, or deletions. In some embodiments, the sense strand comprises the nucleoside sequence of any one of SEQ ID NOs: 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, or 1784, or a nucleic acid sequence thereof having 1 or 2 nucleoside substitutions, additions, or deletions. In some embodiments, the antisense strand comprises the nucleoside sequence of any one of SEQ ID NOs: 1887, 1888, 1889, 1890, 1910, 2126, 2134, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2338, 2371, 2373, 2374, 2419, 2474, 2489, 2491, 2494, 2684, 2695, 2696, 2697, 2698, 2704, 2725, 2726, 2730, 2741, 2742, 2748, 2756, 2799, 2855, 2856, 2859, 2987, 2988, 3003, 3005, 3007, 3008, 3009, 3011, 3012, 3015, 3016, 3018, 3019, 3020, 3169, 3197, 3201, 3202, 3283, 3284, 3425, 3426, 3465, 3634, or 3638, or a nucleic acid sequence thereof having 1 or 2 nucleoside substitutions, additions, or deletions. In some embodiments, the antisense strand comprises a seed region that is not identical to a seed region of a human miRNA. In some embodiments, the sense strand comprises the nucleoside sequence of any one of SEQ ID NOs: 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, or 1803, or 3638, or a nucleic acid sequence thereof having 1 or 2 nucleoside substitutions, additions, or deletions. In some embodiments, the antisense strand comprises the nucleoside sequence of any one of SEQ ID NOs: 1886, 1890, 1910, 1911, 1912, 1915, 1916, 1933, 1934, 1971, 1973, 1979, 1980, 1982, 2003, 2006, 2011, 2012, 2013, 2015, 2019, 2020, 2021, 2022, 2023, 2028, 2050, 2065, 2066, 2071, 2072, 2073, 2084, 2085, 2099, 2100, 2107, 2114, 2115, 2116, 2125, 2126, 2134, 2143, 2145, 2146, 2147, 2158, 2175, 2177, 2179, 2180, 2182, 2184, 2185, 2186, 2187, 2188, 2191, 2192, 2196, 2201, 2203, 2206, 2207, 2210, 2234, 2236, 2240, 2242, 2245, 2246, 2248, 2253, 2267, 2268, 2269, 2276, 2277, 2278, 2279, 2280, 2289, 2371, 2373, 2374, 2419, 2425, 2461, 2462, 2466, 2471, 2474, 2489, 2494, 2526, 2527, 2528, 2529, 2532, 2533, 2535, 2537, 2538, 2541, 2546, 2696, 2697, 2704, 2705, 2708, 2720, 2722, 2730, 2746, 2747, 2756, 2765, 2766, 2767, 2768, 2770, 2773, 2799, 2855, 2856, 2860, 2864, 2882, 2906, 2907, 2908, 2909, 2911, 2966, 2978, 2981, 3001, 3003, 3005, 3007, 3009, 3011, 3018, 3029, 3036, 3038, 3113, 3130, 3139, 3169, 3197, 3203, 3204, 3205, 3259, 3261, 3267, 3269, 3272, 3418, 3425, 3435, 3443, 3451, 3455, 3456, 3457, 3458, 3459, 3460, 3467, 3468, 3547, 3555, 3576, 3594, 3599, 3605, 3609, 3655, 3656, or 3657, or a nucleic acid sequence thereof having 1 or 2 nucleoside substitutions, additions, or deletions. In some embodiments, the sense strand comprises the nucleoside sequence of any one of SEQ ID 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, or 1571, or a nucleic acid sequence thereof having 1 or 2 nucleoside substitutions, additions, or deletions. In some embodiments, the antisense strand comprises the nucleoside sequence of any one of SEQ ID 1890, 1910, 2126, 2134, 2143, 2145, 2146, 2147, 2175, 2177, 2180, 2182, 2184, 2185, 2186, 2187, 2188, 2191, 2192, 2196, 2201, 2203, 2289, 2371, 2373, 2374, 2419, 2474, 2489, 2494, 2696, 2697, 2704, 2730, 2756, 2799, 2855, 2856, 3003, 3005, 3007, 3009, 3011, 3018, 3169, 3197, or 3425, or a nucleic acid sequence thereof having 1 or 2 nucleoside substitutions, additions, or deletions. In some embodiments, the sense strand comprises a seed region that is not identical to a seed region of a human miRNA. In some embodiments, the sense strand comprises the nucleoside sequence of any one of SEQ ID NOs: 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, or 1787, or a nucleic acid sequence thereof having 1 or 2 nucleoside substitutions, additions, or deletions. In some embodiments, the antisense strand comprises the nucleoside sequence of any one of SEQ ID NOs: 1886, 1890, 1910, 1912, 1915, 1916, 1934, 1971, 1973, 1980, 2006, 2008, 2011, 2012, 2013, 2015, 2020, 2023, 2028, 2031, 2050, 2065, 2066, 2071, 2072, 2084, 2085, 2099, 2107, 2114, 2115, 2125, 2126, 2134, 2143, 2147, 2158, 2182, 2184, 2185, 2186, 2187, 2188, 2191, 2196, 2201, 2203, 2207, 2210, 2240, 2242, 2245, 2246, 2248, 2268, 2269, 2276, 2277, 2278, 2280, 2289, 2374, 2425, 2462, 2466, 2471, 2507, 2526, 2532, 2533, 2535, 2537, 2546, 2696, 2697, 2705, 2708, 2713, 2730, 2746, 2754, 2767, 2768, 2773, 2822, 2855, 2856, 2908, 2911, 2918, 2966, 2978, 3011, 3018, 3036, 3038, 3102, 3113, 3197, 3205, 3206, 3269, 3272, 3418, 3435, 3456, 3468, 3547, 3555, 3576, 3594, 3605, 3609, or 3641, or a nucleic acid sequence thereof having 1 or 2 nucleoside substitutions, additions, or deletions. In some embodiments, the sense strand comprises the nucleoside sequence of any one of SEQ ID NOs: 36, 56, 272, 280, 289, 293, 328, 330, 331, 332, 333, 334, 337, 342, 347, 349, 435, 520, 842, 843, 876, 1001, 1002, 1157, 1164, or 1343, or a nucleic acid sequence thereof having 1 or 2 nucleoside substitutions, additions, or deletions. In some embodiments, the antisense strand comprises the nucleoside sequence of any one of SEQ ID NOs: 1890, 1910, 2126, 2134, 2143, 2147, 2182, 2184, 2185, 2186, 2187, 2188, 2191, 2196, 2201, 2203, 2289, 2374, 2696, 2697, 2730, 2855, 2856, 3011, 3018, or 3197, or a nucleic acid sequence thereof having 1 or 2 nucleoside substitutions, additions, or deletions. In some embodiments, the sense strand and/or the antisense strand further comprise a 3' overhang comprising 1, 2, or more nucleosides. In some embodiments, the 3' overhang comprises 2 nucleosides. In some embodiments, (i) the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. In some embodiments, the oligonucleotide comprises 1, 2, 3, 4, 5, 6, 7, 8, 9, 10, 11, 12, 13, 14, 15, 16, 17, 18, 19, or 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages. In some embodiments, the oligonucleotide comprises the modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises one or more 2'fluoro modified nucleosides. In some embodiments, the modified nucleoside comprises a 2' O-alkyl modified nucleoside. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof. In some embodiments, the oligonucleotide comprises an N-acetylgalactosamine (GalNAc) ligand for hepatocyte targeting. In some embodiments, the oligonucleotide comprises 1, 2, 3, 4, 5, 6, 7, 8, 9, 10, 11, 12, 13, 14, 15, 16, 17, 18, 19, 20, or 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides. In some embodiments, the sense strand comprises modification pattern 1S. In some embodiments, the sense strand comprises modification pattern 2S. In some embodiments, the sense strand comprises modification pattern 3S. In some embodiments, the sense strand comprises modification pattern 4S. In some embodiments, the sense strand comprises modification pattern 5S. In some embodiments, the sense strand comprises modification pattern 6S. In some Any of modification patterns 1S-6S may include a GalNAc ligand at the 5' or 3' end. In some embodiments, the antisense strand comprises modification pattern 1AS. In some embodiments, the antisense strand comprises modification pattern 2AS. In some embodiments, the antisense strand comprises modification pattern 3AS. In some embodiments, the antisense strand comprises modification pattern 4AS. In some embodiments, the antisense strand comprises modification pattern 5AS. In some embodiments, the antisense strand comprises modification pattern 6AS. In some embodiments, the antisense strand comprises modification pattern 7AS. In some embodiments, the antisense strand comprises modification pattern 8AS. In some embodiments, the antisense strand comprises modification pattern 9AS. Any of modification patterns 1AS-9AS may include a GalNAc ligand at the 5' or 3' end. In some embodiments, the sense strand comprises modification pattern 1S and the antisense strand comprises modification pattern 1AS, 2AS, 3AS, 4AS, 5AS, 6AS, 7AS, 8AS, or 9AS. In some embodiments, the sense strand comprises modification pattern 2S and the antisense strand comprises modification pattern 1AS, 2AS, 3AS, 4AS, 5AS, 6AS, 7AS, 8AS, or 9AS. In some embodiments, the sense strand comprises modification pattern 3S and the antisense strand comprises modification pattern 1AS, 2AS, 3AS, 4AS, 5AS, 6AS, 7AS, 8AS, or 9AS. In some embodiments, the sense strand comprises modification pattern 4S and the antisense strand comprises modification pattern 1AS, 2AS, 3AS, 4AS, 5AS, 6AS, 7AS, 8AS, or 9AS. In some embodiments, the sense strand comprises modification pattern 5S and the antisense strand comprises modification pattern 1AS, 2AS, 3AS, 4AS, 5AS, 6AS, 7AS, 8AS, or 9AS. In some embodiments, the sense strand comprises modification pattern 6S and the antisense strand comprises modification pattern 1AS, 2AS, 3AS, 4AS, 5AS, 6AS, 7AS, 8AS, or 9AS. In some embodiments, the sense strand comprises a nucleoside sequence comprising or consisting the sequence of any one of SEQ ID NOs: 1-1854 or 13970-13977, or a nucleic acid sequence thereof having 1 or 2 nucleoside substitutions, additions, or deletions, and modification pattern 1S. In some embodiments, the sense strand comprises a nucleoside sequence comprising or consisting of the sequence of any one of SEQ ID NOs: 1-1854 or 13970-13977, and modification pattern 1S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2S. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 1AS. In some embodiments, the antisense strand comprises a nucleoside sequence comprising or consisting of the sequence of any one of SEQ ID NOs: 1855-3708 or 13978-13985, and modification pattern 1AS. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 3AS. In some embodiments, the antisense strand comprises a nucleoside sequence comprising or consisting of the sequence of any one of SEQ ID NOs: 1855-3708 or 13978-13985, and modification pattern 3AS. In some embodiments, the oligonucleotide comprises an ASO. In some embodiments, the ASO is 12-30 nucleosides in length. Also disclosed herein are compositions comprising an oligonucleotide that inhibits the expression of ANGPTL4, wherein the oligonucleotide comprises an antisense oligonucleotide (ASO) about 12-30 nucleosides in length and comprising a nucleoside sequence complementary to about 12-30 contiguous nucleosides of SEQ ID NO: 13935; wherein (i) the oligonucleotide comprises a modification comprising a modified nucleoside and/or a modified internucleoside linkage, and/or (ii) the composition comprises a pharmaceutically acceptable carrier. Also disclosed herein are compositions comprising an oligonucleotide that inhibits the expression of ANGPTL4, wherein the oligonucleotide comprises an ASO about 12-30 nucleosides in length and comprising a nucleoside sequence complementary to about 12-30 contiguous nucleosides of SEQ ID NO: 13936; wherein (i) the oligonucleotide comprises a modification comprising a modified nucleoside and/or a modified internucleoside linkage, and/or (ii) the composition comprises a pharmaceutically acceptable carrier. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 3709-13934. In some embodiments, the ASO comprises modification pattern: 5'-nsnsnsnsnsdNsdNsdNsdNsdNsdNsdNsdNsdNsnsn-snsnsn-3' where "dN" is any deoxynucleotide, "n" is a 2'O-methyl or 2'O-methoxyethyl-modified nucleoside, and "s" is a phosphorothioate linkage. In some embodiments, the ASO comprises one or more of a locked nucleic acid (LNA) or a 2',4' constrained ethyl nucleic acid. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions, and modification pattern ASO1. In some embodiments, the ASO comprises a nucleoside sequence comprising or consisting of the sequence of any one of SEQ ID NOs: 3709-13934, and modification pattern ASO1. In some embodiments, the composition is a pharmaceutical composition. In some embodiments, the composition is sterile. Some embodiments comprise a pharmaceutically acceptable carrier. In some embodiments, the pharmaceutically acceptable carrier comprises water, a buffer, or a saline solution.

Disclosed herein are methods of treating a cardiometabolic disorder in a subject in need thereof, the method comprising administering to the subject a composition comprising an oligonucleotide that targets ANGPTL4. In some embodiments, the cardiometabolic disorder comprises a cardiovascular disorder. In some embodiments, the cardiometabolic disorder comprises a metabolic disorder. Also disclosed herein are methods of treating a metabolic disorder in a subject in need thereof, the method comprising administering to the subject a composition comprising an oligonucleotide that targets ANGPTL4. In some embodiments, the metabolic disorder comprises hyperlipidemia. In some embodiments, the metabolic disorder comprises hypertriglyceridemia. In some embodiments, the metabolic disorder comprises diabetes. In some embodiments, the metabolic disorder comprises type 2 diabetes. Also disclosed herein are methods of treating a cardiovascular disorder in a subject in need thereof, the method comprising administering to the subject a composition comprising an oligonucleotide that targets ANGPTL4. In some embodiments, the cardiovascular disorder comprises heart disease. In some embodiments, the cardiovascular disorder comprises myocardial infarction. In some embodiments, the cardiovascular disorder comprises angina pectoris. In some embodiments, the cardiovascular disorder comprises atherosclerosis. In some embodiments, the subject is an animal, a mammal, a dog, a cat, cattle, a rodent, a mouse, a rat, a primate, or a monkey. In some embodiments, the subject is a human. In some embodiments, the subject is ≥40 years of age. In some embodiments, the subject is ≤85 years of age. In some embodiments, the subject is ≥40 and ≤85 years of age. In some embodiments, a baseline measurement is obtained in a sample obtained from the subject prior to administering the composition to the subject. In some embodiments, the baseline measurement is a baseline triglyceride measurement. In some embodiments, the baseline measurement is a baseline cholesterol measurement. In some embodiments, the baseline measurement is a baseline HDL measurement. In some embodiments, the baseline measurement is a baseline glucose measurement. In some embodiments, the baseline measurement is a baseline insulin measurement. In some embodiments, the baseline measurement is a baseline ANGPTL4 protein measurement. In some embodiments, the sample is a blood, plasma, or serum sample. In some embodiments, the sample is a serum sample. In some embodiments, the baseline measurement is obtained by an immunoassay, a colorimetric assay, or a fluorescence assay. In some embodiments, the baseline measurement is a baseline ANGPTL4 mRNA measurement. In some embodiments, the sample is a tissue sample. In some embodiments, the tissue sample comprises liver, adipose, small intestine, mesenteric lymph node, or cardiac tissue. In some embodiments, the tissue sample is a liver sample. In some embodiments, the baseline measurement is obtained by PCR. In some embodiments, the sample is obtained from the subject after an overnight fasting period. In some embodiments, the sample is obtained from the subject in a fed state. In some embodiments, the composition reduces circulating triglycerides relative to the baseline triglyceride measurement. In some embodiments, the reduced triglycerides are measured in a second sample obtained from the subject after administering the composition to the subject. In some embodiments, the composition reduces circulating cholesterol relative to the baseline cholesterol measurement. In some embodiments, the reduced cholesterol is measured in a second sample obtained from the subject after administering the composition to the subject. In some embodiments, the composition increases circulating HDL relative to the baseline HDL measurement. In some embodiments, the increased HDL is measured in a second sample obtained from the subject after administering the composition to the subject. In some embodiments, the composition reduces circulating glucose relative to the baseline glucose measurement. In some embodiments, the reduced glucose is measured in a second sample obtained from the subject after administering the composition to the subject. In some embodiments, the composition reduces circulating ANGPTL4 protein levels relative to the baseline ANGPTL4 protein measurement. In some embodiments, the reduced ANGPTL4 protein levels are measured in a second sample obtained from the subject after administering the composition to the subject. In some embodiments, the composition reduces ANGPTL4 mRNA levels relative to the baseline ANGPTL4 mRNA measurement. In some embodiments, the reduced ANGPTL4 mRNA levels are measured in a second sample obtained from the subject after administering the composition to the subject. In some embodiments, the oligonucleotide comprises an siRNA comprising a sense strand and an antisense strand. In some embodiments, the sense strand is 14-30 nucleosides in length. In some embodiments, the antisense strand is 14-30 nucleosides in length. In some embodiments, the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13935. In some embodiments, the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13936. In some embodiments, the sense strand and the antisense strand form a double-stranded RNA duplex. In some embodiments, the first base pair of the double-stranded RNA duplex is an AU base pair. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions. In some embodiments, the sense strand comprises a nucleoside sequence comprising or consisting of the sequence of any one of SEQ ID NOs: 1-1854 or 13970-13977. In some embodiments, the sense strand further comprises a 3' overhang comprising 1, 2, or more nucleosides. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions. In some embodiments, the antisense strand comprises a nucleoside sequence comprising or consisting of the sequence of any one of SEQ ID NOs: 1855-3708 or 13978-13985. In some embodiments, the antisense strand further comprises a 3' overhang comprising 1, 2, or more nucleosides. In some embodiments, the siRNA binds with a 19mer in a human ANGPTL4 mRNA. In some embodiments, the siRNA binds with a 17mer in a non-human primate ANGPTL4 mRNA. In some embodiments, the siRNA binds with a 19mer in a human ANGPTL4 mRNA. In some embodiments, the siRNA binds with a human ANGPTL4 mRNA and less than or equal to 20 human off-targets, with no more than 2 mismatches in the antisense strand. In some embodiments, siRNA binds with a human ANGPTL4 mRNA target site that does not harbor an SNP, with a minor allele frequency (MAF) greater or equal to 1% (pos. 2-18). In some embodiments, the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside substitutions, additions, or deletions; and/or the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside substitutions, additions, or deletions. In some embodiments, the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803; and/or the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657. In some embodiments, the sense strand comprises the nucleoside sequence of any one of SEQ ID NOs: 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, or 1787, or a nucleic acid sequence thereof having 1 or 2 nucleoside substitutions, additions, or deletions. In some embodiments, the antisense strand comprises the nucleoside sequence of any one of SEQ ID NOs: 1887, 1888, 1889, 1890, 1910, 1975, 2126, 2134, 2136, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2335, 2338, 2363, 2371, 2373, 2374, 2419, 2474, 2489, 2491, 2494, 2684, 2688, 2695, 2696, 2697, 2698, 2704, 2725, 2726, 2730, 2741, 2742, 2748, 2751, 2756, 2799, 2855, 2856, 2859, 2891, 2987, 2988, 2991, 3003, 3005, 3007, 3008, 3009, 3011, 3012, 3015, 3016, 3018, 3019, 3020, 3025, 3026, 3102, 3103, 3169, 3192, 3197, 3201, 3202, 3283, 3284, 3424, 3425, 3426, 3464, 3465, 3471, 3634, 3638, or 3641, or a nucleic acid sequence thereof having 1 or 2 nucleoside substitutions, additions, or deletions. In some embodiments, the sense strand comprises the nucleoside sequence of any one of SEQ ID NOs: 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, or 1803, or a nucleic acid sequence thereof having 1 or 2 nucleoside substitutions, additions, or deletions. In some embodiments, the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1966, 1970, 1971, 1972, 1973, 1974, 1979, 1980, 1981, 1982, 1983, 2003, 2004, 2006, 2007, 2011, 2012, 2013, 2015, 2018, 2019, 2020, 2021, 2022, 2023, 2026, 2028, 2029, 2050, 2053, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2234, 2236, 2240, 2242, 2245, 2246, 2247, 2248, 2251, 2252, 2253, 2256, 2258, 2259, 2265, 2266, 2267, 2268, 2269, 2274, 2275, 2276, 2277, 2278, 2279, 2280, 2281, 2282, 2283, 2284, 2285, 2289, 2338, 2371, 2373, 2374, 2419, 2424, 2425, 2426, 2461, 2462, 2464, 2465, 2466, 2470, 2471, 2474, 2489, 2491, 2494, 2526, 2527, 2528, 2529, 2530, 2531, 2532, 2533, 2535, 2536, 2537, 2538, 2540, 2541, 2543, 2546, 2549, 2684, 2695, 2696, 2697, 2698, 2704, 2705, 2706, 2707, 2708, 2710, 2711, 2720, 2722, 2725, 2726, 2730, 2741, 2742, 2744, 2746, 2747, 2748, 2756, 2765, 2766, 2767, 2768, 2769, 2770, 2771, 2772, 2773, 2774, 2775, 2776, 2799, 2855, 2856, 2859, 2860, 2863, 2864, 2865, 2867, 2882, 2886, 2906, 2907, 2908, 2909, 2911, 2912, 2966, 2976, 2978, 2980, 2981, 2987, 2988, 3001, 3002, 3003, 3005, 3007, 3008, 3009, 3011, 3012, 3015, 3016, 3018, 3019, 3020, 3029, 3036, 3038, 3106, 3107, 3113, 3130, 3139, 3164, 3169, 3197, 3201, 3202, 3203, 3204, 3205, 3259, 3261, 3267, 3268, 3269, 3270, 3271, 3272, 3283, 3284, 3302, 3373, 3377, 3410, 3415, 3417, 3418, 3419, 3425, 3426, 3434, 3435, 3443, 3451, 3455, 3456, 3457, 3458, 3459, 3460, 3465, 3467, 3468, 3547, 3553, 3555, 3556, 3557, 3576, 3594, 3595, 3596, 3599, 3601, 3602, 3603, 3605, 3608, 3609, 3633, 3634, 3638, 3642, 3652, 3653, 3655, 3656, or 3657, or a nucleic acid sequence thereof having 1 or 2 nucleoside substitutions, additions, or deletions. In some embodiments, the sense strand comprises the nucleoside sequence of any one of SEQ ID NOs: 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, or 1784, or a nucleic acid sequence thereof having 1 or 2 nucleoside substitutions, additions, or deletions. In some embodiments, the antisense strand comprises the nucleoside sequence of any one of SEQ ID NOs: 1887, 1888, 1889, 1890, 1910, 2126, 2134, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2338, 2371, 2373, 2374, 2419, 2474, 2489, 2491, 2494, 2684, 2695, 2696, 2697, 2698, 2704, 2725, 2726, 2730, 2741, 2742, 2748, 2756, 2799, 2855, 2856, 2859, 2987, 2988, 3003, 3005, 3007, 3008, 3009, 3011, 3012, 3015, 3016, 3018, 3019, 3020, 3169, 3197, 3201, 3202, 3283, 3284, 3425, 3426, 3465, 3634, or 3638. In some embodiments, the antisense strand comprises a seed region that is not identical to a seed region of a human miRNA. In some embodiments, the sense strand comprises the nucleoside sequence of any one of SEQ ID NOs: 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, or 1803, or 3638, or a nucleic acid sequence thereof having 1 or 2 nucleoside substitutions, additions, or deletions. In some embodiments, the antisense strand comprises the nucleoside sequence of any one of SEQ ID NOs: 1886, 1890, 1910, 1911, 1912, 1915, 1916, 1933, 1934, 1971, 1973, 1979, 1980, 1982, 2003, 2006, 2011, 2012, 2013, 2015, 2019, 2020, 2021, 2022, 2023, 2028, 2050, 2065, 2066, 2071, 2072, 2073, 2084, 2085, 2099, 2100, 2107, 2114, 2115, 2116, 2125, 2126, 2134, 2143, 2145, 2146, 2147, 2158, 2175, 2177, 2179, 2180, 2182, 2184, 2185, 2186, 2187, 2188, 2191, 2192, 2196, 2201, 2203, 2206, 2207, 2210, 2234, 2236, 2240, 2242, 2245, 2246, 2248, 2253, 2267, 2268, 2269, 2276, 2277, 2278, 2279, 2280, 2289, 2371, 2373, 2374, 2419, 2425, 2461, 2462, 2466, 2471, 2474, 2489, 2494, 2526, 2527, 2528, 2529, 2532, 2533, 2535, 2537, 2538, 2541, 2546, 2696, 2697, 2704, 2705, 2708, 2720, 2722, 2730, 2746, 2747, 2756, 2765, 2766, 2767, 2768, 2770, 2773, 2799, 2855, 2856, 2860, 2864, 2882, 2906, 2907, 2908, 2909, 2911, 2966, 2978, 2981, 3001, 3003, 3005, 3007, 3009, 3011, 3018, 3029, 3036, 3038, 3113, 3130, 3139, 3169, 3197, 3203, 3204, 3205, 3259, 3261, 3267, 3269, 3272, 3418, 3425, 3435, 3443, 3451, 3455, 3456, 3457, 3458, 3459, 3460, 3467, 3468, 3547, 3555, 3576, 3594, 3599, 3605, 3609, 3655, 3656, or 3657, or a nucleic acid sequence thereof having 1 or 2 nucleoside substitutions, additions, or deletions. In some embodiments, the sense strand comprises the nucleoside sequence of any one of SEQ ID 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, or 1571, or a nucleic acid sequence thereof having 1 or 2 nucleoside substitutions, additions, or deletions. In some embodiments, the antisense strand comprises the nucleoside sequence of any one of SEQ ID 1890, 1910, 2126, 2134, 2143, 2145, 2146, 2147, 2175, 2177, 2180, 2182, 2184, 2185, 2186, 2187, 2188, 2191, 2192, 2196, 2201, 2203, 2289, 2371, 2373, 2374, 2419, 2474, 2489, 2494, 2696, 2697, 2704, 2730, 2756, 2799, 2855, 2856, 3003, 3005, 3007, 3009, 3011, 3018, 3169, 3197, or 3425, or a nucleic acid sequence thereof having 1 or 2 nucleoside substitutions, additions, or deletions. In some embodiments, the sense strand comprises a seed region that is not identical to a seed region of a human miRNA. In some embodiments, the sense strand comprises the nucleoside sequence of any one of SEQ ID NOs: 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, or 1787, or a nucleic acid sequence thereof having 1 or 2 nucleoside substitutions, additions, or deletions. In some embodiments, the antisense strand comprises the nucleoside sequence of any one of SEQ ID NOs: 1886, 1890, 1910, 1912, 1915, 1916, 1934, 1971, 1973, 1980, 2006, 2008, 2011, 2012, 2013, 2015, 2020, 2023, 2028, 2031, 2050, 2065, 2066, 2071, 2072, 2084, 2085, 2099, 2107, 2114, 2115, 2125, 2126, 2134, 2143, 2147, 2158, 2182, 2184, 2185, 2186, 2187, 2188, 2191, 2196, 2201, 2203, 2207, 2210, 2240, 2242, 2245, 2246, 2248, 2268, 2269, 2276, 2277, 2278, 2280, 2289, 2374, 2425, 2462, 2466, 2471, 2507, 2526, 2532, 2533, 2535, 2537, 2546, 2696, 2697, 2705, 2708, 2713, 2730, 2746, 2754, 2767, 2768, 2773, 2822, 2855, 2856, 2908, 2911, 2918, 2966, 2978, 3011, 3018, 3036, 3038, 3102, 3113, 3197, 3205, 3206, 3269, 3272, 3418, 3435, 3456, 3468, 3547, 3555, 3576, 3594, 3605, 3609, or 3641, or a nucleic acid sequence thereof having 1 or 2 nucleoside substitutions, additions, or deletions. In some embodiments, the sense strand comprises the nucleoside sequence of any one of SEQ ID NOs: 36, 56, 272, 280, 289, 293, 328, 330, 331, 332, 333, 334, 337, 342, 347, 349, 435, 520, 842, 843, 876, 1001, 1002, 1157, 1164, or 1343, or a nucleic acid sequence thereof having 1 or 2 nucleoside substitutions, additions, or deletions. In some embodiments, the antisense strand comprises the nucleoside sequence of any one of SEQ ID NOs: 1890, 1910, 2126, 2134, 2143, 2147, 2182, 2184, 2185, 2186, 2187, 2188, 2191, 2196, 2201, 2203, 2289, 2374, 2696, 2697, 2730, 2855, 2856, 3011, 3018, or 3197, or a nucleic acid sequence thereof having 1 or 2 nucleoside substitutions, additions, or deletions. In some embodiments, the sense strand and/or the antisense strand further comprise a 3' overhang comprising 1, 2, or more nucleosides. In some embodiments, the 3' overhang comprises 2 nucleosides. In some embodiments, (i) the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. In some embodiments, the oligonucleotide comprises 1, 2, 3, 4, 5, 6, 7, 8, 9, 10, 11, 12, 13, 14, 15, 16, 17, 18, 19, or 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages. In some embodiments, the oligonucleotide comprises the modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises one or more 2'fluoro modified nucleosides. In some embodiments, the modified nucleoside comprises a 2' O-alkyl modified nucleoside. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof. In some embodiments, the oligonucleotide comprises an N-acetylgalactosamine (GalNAc) ligand for hepatocyte targeting. In some embodiments, the oligonucleotide comprises 1, 2, 3, 4, 5, 6, 7, 8, 9, 10, 11, 12, 13, 14, 15, 16, 17, 18, 19, 20, or 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides. In some embodiments, the sense strand comprises modification pattern 1S. In some embodiments, the sense strand comprises modification pattern 2S. In some embodiments, the sense strand comprises modification pattern 3S. In some embodiments, the sense strand comprises modification pattern 4S. In some embodiments, the sense strand comprises modification pattern 5S. In some embodiments, the sense strand comprises modification pattern 6S. In some Any of modification patterns 1S-6S may include a GalNAc ligand at the 5' or 3' end. In some embodiments, the antisense strand comprises modification pattern 1AS. In some embodiments, the antisense strand comprises modification pattern 2AS. In some embodiments, the antisense strand comprises modification pattern 3AS. In some embodiments, the antisense strand comprises modification pattern 4AS. In some embodiments, the antisense strand comprises modification pattern 5AS. In some embodiments, the antisense strand comprises modification pattern 6AS. In some embodiments, the antisense strand comprises modification pattern 7AS. In some embodiments, the antisense strand comprises modification pattern 8AS. In some embodiments, the antisense strand comprises modification pattern 9AS. Any of modification patterns 1AS-9AS may include a GalNAc ligand at the 5' or 3' end. In some embodiments, the sense strand comprises modification pattern 15 and the antisense strand comprises modification pattern 1AS, 2AS, 3AS, 4AS, 5AS, 6AS, 7AS, 8AS, or 9AS. In some embodiments, the sense strand comprises modification pattern 2S and the antisense strand comprises modification pattern 1AS, 2AS, 3AS, 4AS, 5AS, 6AS, 7AS, 8AS, or 9AS. In some embodiments, the sense strand comprises modification pattern 3S and the antisense strand comprises modification pattern 1AS, 2AS, 3AS, 4AS, 5AS, 6AS, 7AS, 8AS, or 9AS. In some embodiments, the sense strand comprises modification pattern 4S and the antisense strand comprises modification pattern 1AS, 2AS, 3AS, 4AS, 5AS, 6AS, 7AS, 8AS, or 9AS. In some embodiments, the sense strand comprises modification pattern 5S and the antisense strand comprises modification pattern 1AS, 2AS, 3AS, 4AS, 5AS, 6AS, 7AS, 8AS, or 9AS. In some embodiments, the sense strand comprises modification pattern 6S and the antisense strand comprises modification pattern 1AS, 2AS, 3AS, 4AS, 5AS, 6AS, 7AS, 8AS, or 9AS. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 1S. In some embodiments, the sense strand comprises a nucleoside sequence comprising or consisting of the sequence of any one of SEQ ID NOs: 1-1854 or 13970-13977, and modification pattern 15. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2S. In some embodiments, the sense strand comprises a nucleoside sequence comprising or consisting of the sequence of any one of SEQ ID NOs: 1-1854 or 13970-13977, and modification pattern 2S. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 1AS. In some embodiments, the antisense strand comprises a nucleoside sequence comprising or consisting of the sequence of any one of SEQ ID NOs: 1855-3708 or 13978-13985, and modification pattern 1AS. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 3AS. In some embodiments, the antisense strand comprises a nucleoside sequence comprising or consisting of the sequence of any one of SEQ ID NOs: 1855-3708 or 13978-13985, and modification pattern 3AS. In some embodiments, the oligonucleotide comprises an ASO. In some embodiments, the ASO is 12-30 nucleosides in length. In some embodiments, the oligonucleotide comprises an antisense oligonucleotide (ASO) about 12-30 nucleosides in length and comprising a nucleoside sequence complementary to about 12-30 contiguous nucleosides of SEQ ID NO: 13935; wherein (i) the oligonucleotide comprises a modification comprising a modified nucleoside and/or a modified internucleoside linkage, and/or (ii) the composition comprises a pharmaceutically acceptable carrier. In some embodiments, the oligonucleotide comprises an ASO about 12-30 nucleosides in length and comprising a nucleoside sequence complementary to about 12-30 contiguous nucleosides of SEQ ID NO: 13936; wherein (i) the oligonucleotide comprises a modification comprising a modified nucleoside and/or a modified internucleoside linkage, and/or (ii) the composition comprises a pharmaceutically acceptable carrier. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 3709-13934. In some embodiments, the ASO comprises modification pattern: 5'-nsnsnsnsnsdNsdNsdNsdNsdNsdNsdNsdNsdNsdNsnsn-snsnsn-3' where "dN" is any deoxynucleotide, "n" is a 2'O-methyl or 2'O-methoxyethyl-modified nucleoside, and "s" is a phosphorothioate linkage. In some embodiments, the ASO comprises one or more of a locked nucleic acid (LNA) or a 2',4' constrained ethyl nucleic acid. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions, and modification pattern ASO1. In some embodiments, the ASO comprises a nucleoside sequence comprising or consisting of the sequence of any one of SEQ ID NOs: 3709-13934, and modification pattern ASO1. In some embodiments, the composition is a pharmaceutical composition. In some embodiments, the composition is sterile. In some embodiments, the composition comprises a pharmaceutically acceptable carrier. In some embodiments, the pharmaceutically acceptable carrier comprises water, a buffer, or a saline solution.

DETAILED DESCRIPTION

Large-scale human genetic data can improve the success rate of pharmaceutical discovery and development. A Genome Wide Association Study (GWAS) may detect associations between genetic variants and traits in a population sample. A GWAS may enable better understanding of the biology of disease, and provide applicable treatments. A GWAS can utilize genotyping and/or sequencing data, and often involves an evaluation of millions of genetic variants that are relatively evenly distributed across the genome. The most common GWAS design is the case-control study, which involves comparing variant frequencies in cases versus controls. If a variant has a significantly different frequency in cases versus controls, that variant is said to be associated with disease. Association statistics that may be used in a GWAS are p-values, as a measure of statistical significance; odds ratios (OR), as a measure of effect size; or beta coefficients (beta), as a measure of effect size. Researchers often assume an additive genetic model and calculate an allelic odds ratio, which is the increased (or decreased) risk of disease conferred by each additional copy of an allele (compared to carrying no copies of that allele). An additional concept in design and interpretation of GWAS is that of linkage disequilibrium, which is the non-random association of alleles. The presence of linkage disequilibrium can obfuscate which variant is "causal."

Functional annotation of variants and/or wet lab experimentation can identify the causal genetic variant identified via GWAS, and in many cases may lead to the identification of disease-causing genes. In particular, understanding the functional effect of a causal genetic variant (for example, loss of protein function, gain of protein function, increase in gene expression, or decrease in gene expression) may allow that variant to be used as a proxy for therapeutic modulation of the target gene, or to gain insight into potential therapeutic efficacy and safety of a therapeutic that modulates that target.

Identification of such gene-disease associations has provided insights into disease biology and may be used to identify novel therapeutic targets for the pharmaceutical industry. In order to translate the therapeutic insights derived from human genetics, disease biology in patients may be exogenously 'programmed' into replicating the observation from human genetics. There are several potential options for therapeutic modalities that may be brought to bear in translating therapeutic targets identified via human genetics into novel medicines. These may include well established therapeutic modalities such as small molecules and monoclonal antibodies, maturing modalities such as oligonucleotides, and emerging modalities such as gene therapy and gene editing. The choice of therapeutic modality can depend on several factors including the location of a target (for example, intracellular, extracellular, or secreted), a relevant tissue (for example, liver) and a relevant indication.

Cardiovascular and metabolic diseases are leading causes of death, accounting for about one-third of all deaths globally. Angiopoietin-like proteins (ANGPTLs) are regulators of lipoprotein metabolism and may serve as therapeutic targets for modulation of lipid levels and cardiometabolic disease risk. ANGPTLs are a family of eight proteins with some functional similarities to angiopoietins. They typically have a characteristic structure that includes an N-terminal coiled-coil domain that mediates homo-oligomerization and a C-terminal fibrinogen domain involved in signaling.

Angiopoietin-like 4 (ANGPTL4; UniProt ID Q9BY76) is an endogenous inhibitor of lipoprotein lipase (LPL), an enzyme that hydrolyzes triglycerides contained in triglyceride-rich lipoproteins (TRLs) such as chylomicrons and very low-density lipoproteins. ANGPTL4 is a secreted protein that in humans is often most highly expressed in the liver and adipose tissue. After cellular secretion, ANGPTL4 is often cleaved to 37 kD C-terminal and 15 kD N-terminal fragment, and these oligomerized N-terminal fragments inhibit LPL. In some embodiments, ANGPTL4 is glycosylated. In some embodiments, ANGPTL4 has a coiled-coil N-terminal domain. In some embodiments, ANGPTL4 has a fibrinogen-like C-terminal domain.

Circulating triglycerides are strong and independent positive predictors of cardiovascular disease risk and all-cause mortality, and are also positively correlated with plasma glucose levels, risk of diabetes, metabolic syndrome, and pancreatitis. Additionally, mutations in TRL genes may cause hereditary disorders including familial chylomicronemia syndrome and familial hypertriglyceridemia. Here, it is shown that genetic variants that cause inactivation of ANGPTL4 in humans are associated with decreased triglycerides, increased HDL and decreased risk of diabetes and cardiovascular disease. Therefore, inhibition of ANGPTL4 may serve as a therapeutic strategy for treatment of a range of cardiometabolic diseases.

Disclosed herein are compositions comprising an oligonucleotide that targets Angiopoietin-like 4 (ANGPTL4). The oligonucleotide may include a small interfering RNA (siRNA) or an antisense oligonucleotide (ASO). Also provided herein are methods of treating a metabolic or cardiovascular disorder by providing an oligonucleotide that targets ANGPTL4 to a subject in need thereof.

I. Compositions

Disclosed herein, in some embodiments, are compositions comprising an oligonucleotide. In some embodiments, the composition comprises an oligonucleotide that targets Angiopoietin-like 4 (ANGPTL4). In some embodiments, the composition consists of an oligonucleotide that targets ANGPTL4. In some embodiments, a composition described herein is used in a method of treating a disorder in a subject in need thereof. Some embodiments relate to a composition comprising an oligonucleotide for use in a method of treating a disorder as described herein. Some embodiments relate to use of a composition comprising an oligonucleotide, in a method of treating a disorder as described herein.

In some embodiments, the composition comprises an oligonucleotide that targets ANGPTL4 and when administered to a subject in an effective amount decreases ANGPTL4 mRNA levels in a cell or tissue. In some embodiments, the cell is a hepatocyte. In some embodiments, the tissue is liver or adipose tissue. In some embodiments, the ANGPTL4 mRNA levels are decreased by about 2.5% or more, about 5% or more, or about 7.5% or more, as compared to prior to administration. In some embodiments, the ANGPTL4 mRNA levels are decreased by about 10% or more, as compared to prior to administration. In some embodiments, the ANGPTL4 mRNA levels are decreased by about 20% or more, about 30% or more, about 40% or more, about 50% or more, about 60% or more, about 70% or more, about 80% or more, about 90% or more, or about 100%, as compared to prior to administration. In some embodiments, the ANGPTL4 mRNA levels are decreased by no more than about 2.5%, no more than about 5%, or no more than about 7.5%, as compared to prior to administration. In some embodiments, the ANGPTL4 mRNA levels are decreased by no more than about 10%, as compared to prior to administration. In some embodiments, the ANGPTL4 mRNA levels are decreased by no more than about 20%, no more than about 30%, no more than about 40%, no more than about 50%, no more than about 60%, no more than about 70%, no more than about 80%, or no more than about 90%, as compared to prior to administration. In some embodiments, the ANGPTL4 mRNA levels are decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition comprises an oligonucleotide that targets ANGPTL4 and when administered to a subject in an effective amount decreases circulating ANGPTL4 protein levels in a cell or tissue. In some embodiments, the composition comprises an oligonucleotide that targets ANGPTL4 and when administered to a subject in an effective amount decreases ANGPTL4 protein levels in a fluid such as blood, serum or plasma. In some embodiments, the ANGPTL4 protein levels are decreased by about 2.5% or more, about 5% or more, or about 7.5% or more, as compared to prior to administration. In some embodiments, the ANGPTL4 protein levels are decreased by about 10% or more, as compared to prior to administration. In some embodiments, the ANGPTL4 protein levels are decreased by about 20% or more, about 30% or more, about 40% or more, about 50% or more, about 60% or more, about 70% or more, about 80% or more, about 90% or more, or about 100%, as compared to prior to administration. In some embodiments, the ANGPTL4 protein levels are decreased by no more than about 2.5%, no more than about 5%, or no more than about 7.5%, as compared to prior to administration. In some embodiments, the ANGPTL4 protein levels are decreased by no more than about 10%, as compared to prior to administration. In some embodiments, the ANGPTL4 protein levels are decreased by no more than about 20%, no more than about 30%, no more than about 40%, no more than about 50%, no more than about 60%, no more than about 70%, no more than about 80%, or no more than about 90%, as compared to prior to administration. In some embodiments, the ANGPTL4 protein levels are decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition comprises an oligonucleotide that targets ANGPTL4 and when administered to a subject in an effective amount decreases circulating triglycerides. In some embodiments, the triglycerides are decreased by about 2.5% or more, about 5% or more, or about 7.5% or more, as compared to prior to administration. In some embodiments, the triglycerides are decreased by about 10% or more, as compared to prior to administration. In some embodiments, the triglycerides are decreased by about 20% or more, about 30% or more, about 40% or more, about 50% or more, about 60% or more, about 70% or more, about 80% or more, about 90% or more, or about 100%, as compared to prior to administration. In some embodiments, the triglycerides are decreased by no more than about 2.5%, no more than about 5%, or no more than about 7.5%, as compared to prior to administration. In some embodiments, the triglycerides are decreased by no more than about 10%, as compared to prior to administration. In some embodiments, the triglycerides are decreased by no more than about 20%, no more than about 30%, no more than about 40%, no more than about 50%, no more than about 60%, no more than about 70%, no more than about 80%, or no more than about 90%, as compared to prior to administration. In some embodiments, the triglycerides are decreased by 2.5%, 5%, 7.5%, 10%, 20%, 30%, 40%, 50%, 60%, 70%, 80%, 90%, or 100%, or by a range defined by any of the two aforementioned percentages.

In some embodiments the composition comprises an oligonucleotide that targets ANGPTL4 and when administered to a subject in an effective amount decreases circulating cholesterol. In some embodiments, the circulating cholesterol comprises circulating total cholesterol. In some embodiments, the circulating cholesterol is decreased by about 2.5% or more, about 5% or more, or about 7.5% or more, as compared to prior to administration. In some embodiments, the circulating cholesterol is decreased by about 10% or more, as compared to prior to administration. In some embodiments, the circulating cholesterol is decreased by about 20% or more, about 30% or more, about 40% or more, about 50% or more, about 60% or more, about 70% or more, about 80% or more, about 90% or more, or about 100%, as compared to prior to administration. In some embodiments, the cholesterol is decreased by no more than about 2.5%, no more than about 5%, or no more than about 7.5%, as compared to prior to administration. In some embodiments, the cholesterol is decreased by no more than about 10%, as compared to prior to administration. In some embodiments, the cholesterol is decreased by no more than about 20%, no more than about 30%, no more than about 40%, no more than about 50%, no more than about 60%, no more than about 70%, no more than about 80%, or no more than about 90%, as compared to prior to administration. In some embodiments, the circulating cholesterol is decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition comprises an oligonucleotide that targets ANGPTL4 and when administered to a subject in an effective amount increases circulating high-density lipoproteins (HDL). In some embodiments, the circulating HDL are increased by about 2.5% or more, about 5% or more, or about 7.5% or more, as compared to prior to administration. In some embodiments, the circulating HDL are increased by about 10% or more, as compared to prior to administration. In some embodiments, the circulating HDL are increased by about 20% or more, about 30% or more, about 40% or more, about 50% or more, about 60% or more, about 70% or more, about 80% or more, about 90% or more, or about 100% or more as compared to prior to administration. In some embodiments, the circulating HDL are increased by about 200% or more, about 300% or more, about 400% or more, about 500% or more, about 600% or more, about 700% or more, about 800% or more, about 900% or more, or about 1000% or more, as compared to prior to administration. In some embodiments, the HDL is decreased by no more than about 2.5%, no more than about 5%, or no more than about 7.5%, as compared to prior to administration. In some embodiments, the HDL is decreased by no more than about 10%, as compared to prior to administration. In some embodiments, the HDL is decreased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the HDL is decreased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the circulating HDL are increased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the composition comprises an oligonucleotide that targets ANGPTL4 and when administered to a subject in an effective amount decreases circulating glucose. In some embodiments, the circulating glucose is decreased by about 2.5% or more, about 5% or more, or about 7.5% or more, as compared to prior to administration. In some embodiments, the circulating glucose is decreased by about 10% or more, as compared to prior to administration. In some embodiments, the circulating glucose is decreased by about 20% or more, about 30% or more, about 40% or more, about 50% or more, about 60% or more, about 70% or more, about 80% or more, about 90% or more, or about 100%, as compared to prior to administration. In some embodiments, the glucose is decreased by no more than about 2.5%, no more than about 5%, or no more than about 7.5%, as compared to prior to administration. In some embodiments, the glucose is decreased by no more than about 10%, as compared to prior to administration. In some embodiments, the glucose is decreased by no more than about 20%, no more than about 30%, no more than about 40%, no more than about 50%, no more than about 60%, no more than about 70%, no more than about 80%, or no more than about 90%, as compared to prior to administration. In some embodiments, the circulating glucose is decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition comprises an oligonucleotide that targets ANGPTL4 and when administered to a subject in an effective amount increases insulin sensitivity. In some embodiments, the insulin sensitivity is increased by about 2.5% or more, about 5% or more, or about 7.5% or more, as compared to prior to administration. In some embodiments, the insulin sensitivity is increased by about 10% or more, as compared to prior to administration. In some embodiments, the insulin sensitivity is increased by about 20% or more, about 30% or more, about 40% or more, about 50% or more, about 60% or more, about 70% or more, about 80% or more, about 90% or more, or about 100%, or more as compared to prior to administration. In some embodiments, the insulin sensitivity is increased by about 200% or more, about 300% or more, about 400% or more, about 500% or more, about 600% or more, about 700% or more, about 800% or more, about 900% or more, or about 1000% or more, as compared to prior to administration. In some embodiments, the insulin sensitivity is increased by no more than about 2.5%, no more than about 5%, or no more than about 7.5%, as compared to prior to administration. In some embodiments, the insulin sensitivity is increased by no more than about 10%, as compared to prior to administration. In some embodiments, the insulin sensitivity is increased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the insulin sensitivity is increased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the insulin sensitivity is increased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the composition comprises an oligonucleotide that targets ANGPTL4 and when administered to a subject in an effective amount decreases circulating insulin. In some embodiments, the circulating insulin is decreased by about 2.5% or more, about 5% or more, or about 7.5% or more, as compared to prior to administration. In some embodiments, the circulating insulin is decreased by about 10% or more, as compared to prior to administration. In some embodiments, the circulating insulin is decreased by about 20% or more, about 30% or more, about 40% or more, about 50% or more, about 60% or more, about 70% or more, about 80% or more, about 90% or more, or about 100%, as compared to prior to administration. In some embodiments, the insulin is decreased by no more than about 2.5%, no more than about 5%, or no more than about 7.5%, as compared to prior to administration. In some embodiments, the insulin is decreased by no more than about 10%, as compared to prior to administration. In some embodiments, the insulin is decreased by no more than about 20%, no more than about 30%, no more than about 40%, no more than about 50%, no more than about 60%, no more than about 70%, no more than about 80%, or no more than about 90%, as compared to prior to administration. In some embodiments, the circulating insulin is decreased by 2.5%, 5%, 7.5%, 10%, 20%, 30%, 40%, 50%, 60%, 70%, 80%, 90%, or 100%, or by a range defined by any of the two aforementioned percentages.

A. siRNAs

In some embodiments, the composition comprises an oligonucleotide that targets Angiopoietin-like 4 (ANGPTL4), wherein the oligonucleotide comprises a small interfering RNA (siRNA). In some embodiments, the composition comprises an oligonucleotide that targets Angiopoietin-like 4 (ANGPTL4), wherein the oligonucleotide comprises a small interfering RNA (siRNA) comprising a sense strand and an antisense strand. In some embodiments, the sense strand comprises RNA. In some embodiments, the antisense strand comprises RNA.

In some embodiments, the siRNA comprises a sense strand and an antisense strand, the antisense strand being complementary with no more than 2 mismatches to a portion of a nucleic acid having the nucleoside sequence of SEQ ID NO: 13936, and each strand having 12 to 30 nucleotides. In some embodiments, the siRNA comprises a sense strand and an antisense strand, the antisense strand being complementary with no more than 2 mismatches to a portion of a nucleic acid having the nucleoside sequence of SEQ ID NO: 13935, and each strand having 12 to 30 nucleotides.

In some embodiments, the siRNA comprises a sense strand and an antisense strand, the antisense strand being 100% complementary to a portion of a nucleic acid having the nucleoside sequence of SEQ ID NO: 13936, and each strand having 12 to 30 nucleotides. In some embodiments, the siRNA comprises a sense strand and an antisense strand, the antisense strand being 100% complementary to a portion of a nucleic acid having the nucleoside sequence of SEQ ID NO: 13935, and each strand having 12 to 30 nucleotides.

In some embodiments, the composition comprises an oligonucleotide that inhibits the expression of ANGPTL4, wherein the oligonucleotide comprises an siRNA comprising a sense strand and an antisense strand, wherein the sense strand is 14-30 nucleosides in length. In some embodiments, the composition comprises a sense strange that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the composition comprises an antisense strand is 14-30 nucleosides in length. In some embodiments, the composition comprises an antisense strange that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers.

In some embodiments, the composition comprises an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of a full-length human ANGPTL4 mRNA sequence such as SEQ ID NO: 13935. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 13935.

In some embodiments, the composition comprises an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of a full-length human ANGPTL4 pre-mRNA sequence SEQ ID NO: 13936. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 13936.

In some embodiments, the composition comprises an oligonucleotide that inhibits the expression of ANGPTL4, wherein the oligonucleotide comprises an siRNA comprising a sense strand and an antisense strand, wherein the sense strand and the antisense strand form a double-stranded RNA duplex. In some embodiments, the first base pair of the double-stranded RNA duplex is an AU base pair.

In some embodiments, the composition comprises an oligonucleotide that inhibits the expression of ANGPTL4, wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions. In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside additions at the 3' end. The sequence of any one of SEQ ID NOs: 1-1854 or 13970-13977 may include sequence of any one of SEQ ID NOs: 1-1854. The sequence of any one of SEQ ID NOs: 1-1854 or 13970-13977 may include sequence of any one of SEQ ID NOs: 13970-13977.

In some embodiments, the composition comprises an oligonucleotide that inhibits the expression of ANGPTL4, wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977.

In some embodiments, the composition comprises an oligonucleotide that inhibits the expression of ANGPTL4, wherein the oligonucleotide comprises an siRNA comprising a sense strand and an antisense strand, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions. In some embodiments, the antisense strand sequence comprises a nucleoside sequence comprising or consisting of the sequence of any one of SEQ ID NOs: 1855-3708 or 13978-13985, or a nucleic acid sequence thereof having 3 or 4 nucleoside substitutions, additions, or deletions. In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides. In some embodiments, the antisense strand comprises a nucleoside sequence comprising or consisting of the sequence of any one of SEQ ID NOs: 1855-3708 or 13978-13985, or a nucleic acid sequence thereof having 1 or 2 nucleoside additions at the 3' end. The sequence of any one of SEQ ID NOs: 1855-3708 or 13978-13985 may include sequence of any one of SEQ ID NOs: 1855-3708. The sequence of any one of SEQ ID NOs: 1855-3708 or 13978-13985 may include sequence of any one of SEQ ID NOs: 13978-13985.

In some embodiments, the composition comprises an oligonucleotide that inhibits the expression of ANGPTL4, wherein the oligonucleotide comprises an siRNA comprising a sense strand and an antisense strand, wherein the antisense strand comprises a nucleoside sequence comprising or consisting of the sequence of any one of SEQ ID NOs: 1855-3708 or 13978-13985.

In some embodiments, the composition comprises an oligonucleotide that inhibits the expression of ANGPTL4, wherein the oligonucleotide comprises an siRNA comprising a sense strand and an antisense strand, wherein the siRNA binds with a 19mer in a human ANGPTL4 mRNA. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a human ANGPTL4 mRNA.

In some embodiments, the composition comprises an oligonucleotide that inhibits the expression of ANGPTL4, wherein the oligonucleotide comprises an siRNA comprising a sense strand and an antisense strand, wherein the siRNA binds with a 17mer in a non-human primate ANGPTL4 mRNA. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a non-human primate ANGPTL4 mRNA.

In some embodiments, the composition comprises an oligonucleotide that inhibits the expression of ANGPTL4, wherein the oligonucleotide comprises an siRNA comprising a sense strand and an antisense strand, wherein the siRNA binds with a 19mer in a human ANGPTL4 mRNA, or a combination thereof. In some embodiments, the siRNA binds with a 12mer, a 13mer, a 14mer, a 15mer, a 16mer, a 17mer, and 18mer, a 19mer, a 20mer, a 21mer, a 22mer, a 23mer, a 24mer, or a 25mer in a human ANGPTL4 mRNA.

In some embodiments, the composition comprises an oligonucleotide that inhibits the expression of ANGPTL4, wherein the oligonucleotide comprises an siRNA comprising a sense strand and an antisense strand, wherein the siRNA binds with a human ANGPTL4 mRNA and less than or equal to 20 human off-targets, with no more than 2 mismatches in the antisense strand. In some embodiments, the siRNA binds with a human ANGPTL4 mRNA and less than or equal to 10 human off-targets, with no more than 2 mismatches in the antisense strand. In some embodiments, the siRNA binds with a human ANGPTL4 mRNA and less than or equal to 30 human off-targets, with no more than 2 mismatches in the antisense strand. In some embodiments, the siRNA binds with a human ANGPTL4 mRNA and less than or equal to 40 human off-targets, with no more than 2 mismatches in the antisense strand. In some embodiments, the siRNA binds with a human ANGPTL4 mRNA and less than or equal to 50 human off-targets, with no more than 2 mismatches in the antisense strand. In some embodiments, the siRNA binds with a human ANGPTL4 mRNA and less than or equal to 10 human off-targets, with no more than 3 mismatches in the antisense strand. In some embodiments, the siRNA binds with a human ANGPTL4 mRNA and less than or equal to 20 human off-targets, with no more than 3 mismatches in the antisense strand. In some embodiments, the siRNA binds with a human ANGPTL4 mRNA and less than or equal to 30 human off-targets, with no more than 3 mismatches in the antisense strand. In some embodiments, the siRNA binds with a human ANGPTL4 mRNA and less than or equal to 40 human off-targets, with no more than 3 mismatches in the antisense strand. In some embodiments, the siRNA binds with a human ANGPTL4 mRNA and less than or equal to 50 human off-targets, with no more than 3 mismatches in the antisense strand.

In some embodiments, the composition comprises an oligonucleotide that inhibits the expression of ANGPTL4, wherein the oligonucleotide comprises an siRNA comprising a sense strand and an antisense strand, siRNA binds with a human ANGPTL4 mRNA target site that does not harbor an SNP, with a minor allele frequency (MAF) greater or equal to 1% (pos. 2-18). In some embodiments, the MAF is greater or equal to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside substitutions, additions, or deletions; and/or the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside substitutions, additions, or deletions.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803; and/or the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657.

In some embodiments, the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside additions at the 3' end. In some embodiments, the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside additions at the 3' end. For example, the nucleic acid sequence may have 2 uracil nucleoside additions at the 3' end. The nucleic acid sequence may have 1 uracil nucleoside addition at the 3' end. The nucleic acid sequence may have more than 2 nucleoside additions at the 3' end.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, or 1787; and/or the antisense strand comprises the nucleoside sequence of any one of SEQ ID NOs: 1887, 1888, 1889, 1890, 1910, 1975, 2126, 2134, 2136, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2335, 2338, 2363, 2371, 2373, 2374, 2419, 2474, 2489, 2491, 2494, 2684, 2688, 2695, 2696, 2697, 2698, 2704, 2725, 2726, 2730, 2741, 2742, 2748, 2751, 2756, 2799, 2855, 2856, 2859, 2891, 2987, 2988, 2991, 3003, 3005, 3007, 3008, 3009, 3011, 3012, 3015, 3016, 3018, 3019, 3020, 3025, 3026, 3102, 3103, 3169, 3192, 3197, 3201, 3202, 3283, 3284, 3424, 3425, 3426, 3464, 3465, 3471, 3634, 3638, or 3641.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, or 1803; and/or the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1966, 1970, 1971, 1972, 1973, 1974, 1979, 1980, 1981, 1982, 1983, 2003, 2004, 2006, 2007, 2011, 2012, 2013, 2015, 2018, 2019, 2020, 2021, 2022, 2023, 2026, 2028, 2029, 2050, 2053, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2234, 2236, 2240, 2242, 2245, 2246, 2247, 2248, 2251, 2252, 2253, 2256, 2258, 2259, 2265, 2266, 2267, 2268, 2269, 2274, 2275, 2276, 2277, 2278, 2279, 2280, 2281, 2282, 2283, 2284, 2285, 2289, 2338, 2371, 2373, 2374, 2419, 2424, 2425, 2426, 2461, 2462, 2464, 2465, 2466, 2470, 2471, 2474, 2489, 2491, 2494, 2526, 2527, 2528, 2529, 2530, 2531, 2532, 2533, 2535, 2536, 2537, 2538, 2540, 2541, 2543, 2546, 2549, 2684, 2695, 2696, 2697, 2698, 2704, 2705, 2706, 2707, 2708, 2710, 2711, 2720, 2722, 2725, 2726, 2730, 2741, 2742, 2744, 2746, 2747, 2748, 2756, 2765, 2766, 2767, 2768, 2769, 2770, 2771, 2772, 2773, 2774, 2775, 2776, 2799, 2855, 2856, 2859, 2860, 2863, 2864, 2865, 2867, 2882, 2886, 2906, 2907, 2908, 2909, 2911, 2912, 2966, 2976, 2978, 2980, 2981, 2987, 2988, 3001, 3002, 3003, 3005, 3007, 3008, 3009, 3011, 3012, 3015, 3016, 3018, 3019, 3020, 3029, 3036, 3038, 3106, 3107, 3113, 3130, 3139, 3164, 3169, 3197, 3201, 3202, 3203, 3204, 3205, 3259, 3261, 3267, 3268, 3269, 3270, 3271, 3272, 3283, 3284, 3302, 3373, 3377, 3410, 3415, 3417, 3418, 3419, 3425, 3426, 3434, 3435, 3443, 3451, 3455, 3456, 3457, 3458, 3459, 3460, 3465, 3467, 3468, 3547, 3553, 3555, 3556, 3557, 3576, 3594, 3595, 3596, 3599, 3601, 3602, 3603, 3605, 3608, 3609, 3633, 3634, 3638, 3642, 3652, 3653, 3655, 3656, or 3657.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, or 1784; and/or the antisense strand comprises the nucleoside sequence of any one of SEQ ID NOs: 1887, 1888, 1889, 1890, 1910, 2126, 2134, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2338, 2371, 2373, 2374, 2419, 2474, 2489, 2491, 2494, 2684, 2695, 2696, 2697, 2698, 2704, 2725, 2726, 2730, 2741, 2742, 2748, 2756, 2799, 2855, 2856, 2859, 2987, 2988, 3003, 3005, 3007, 3008, 3009, 3011, 3012, 3015, 3016, 3018, 3019, 3020, 3169, 3197, 3201, 3202, 3283, 3284, 3425, 3426, 3465, 3634, or 3638.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, or 1803, or 3638; and/or the antisense strand comprises the nucleoside sequence of any one of SEQ ID NOs: 1886, 1890, 1910, 1911, 1912, 1915, 1916, 1933, 1934, 1971, 1973, 1979, 1980, 1982, 2003, 2006, 2011, 2012, 2013, 2015, 2019, 2020, 2021, 2022, 2023, 2028, 2050, 2065, 2066, 2071, 2072, 2073, 2084, 2085, 2099, 2100, 2107, 2114, 2115, 2116, 2125, 2126, 2134, 2143, 2145, 2146, 2147, 2158, 2175, 2177, 2179, 2180, 2182, 2184, 2185, 2186, 2187, 2188, 2191, 2192, 2196, 2201, 2203, 2206, 2207, 2210, 2234, 2236, 2240, 2242, 2245, 2246, 2248, 2253, 2267, 2268, 2269, 2276, 2277, 2278, 2279, 2280, 2289, 2371, 2373, 2374, 2419, 2425, 2461, 2462, 2466, 2471, 2474, 2489, 2494, 2526, 2527, 2528, 2529, 2532, 2533, 2535, 2537, 2538, 2541, 2546, 2696, 2697, 2704, 2705, 2708, 2720, 2722, 2730, 2746, 2747, 2756, 2765, 2766, 2767, 2768, 2770, 2773, 2799, 2855, 2856, 2860, 2864, 2882, 2906, 2907, 2908, 2909, 2911, 2966, 2978, 2981, 3001, 3003, 3005, 3007, 3009, 3011, 3018, 3029, 3036, 3038, 3113, 3130, 3139, 3169, 3197, 3203, 3204, 3205, 3259, 3261, 3267, 3269, 3272, 3418, 3425, 3435, 3443, 3451, 3455, 3456, 3457, 3458, 3459, 3460, 3467, 3468, 3547, 3555, 3576, 3594, 3599, 3605, 3609, 3655, 3656, or 3657.

In some embodiments, the composition comprises an oligonucleotide that inhibits the expression of ANGPTL4, wherein the oligonucleotide comprises an siRNA comprising a sense strand and an antisense strand, the sense strand comprises the nucleoside sequence of any one of SEQ ID 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, or 1571; and/or the antisense strand comprises the nucleoside sequence of any one of SEQ ID 1890, 1910, 2126, 2134, 2143, 2145, 2146, 2147, 2175, 2177, 2180, 2182, 2184, 2185, 2186, 2187, 2188, 2191, 2192, 2196, 2201, 2203, 2289, 2371, 2373, 2374, 2419, 2474, 2489, 2494, 2696, 2697, 2704, 2730, 2756, 2799, 2855, 2856, 3003, 3005, 3007, 3009, 3011, 3018, 3169, 3197, or 3425.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, or 1787; and/or the antisense strand comprises the nucleoside sequence of any one of SEQ ID NOs: 1886, 1890, 1910, 1912, 1915, 1916, 1934, 1971, 1973, 1980, 2006, 2008, 2011, 2012, 2013, 2015, 2020, 2023, 2028, 2031, 2050, 2065, 2066, 2071, 2072, 2084, 2085, 2099, 2107, 2114, 2115, 2125, 2126, 2134, 2143, 2147, 2158, 2182, 2184, 2185, 2186, 2187, 2188, 2191, 2196, 2201, 2203, 2207, 2210, 2240, 2242, 2245, 2246, 2248, 2268, 2269, 2276, 2277, 2278, 2280, 2289, 2374, 2425, 2462, 2466, 2471, 2507, 2526, 2532, 2533, 2535, 2537, 2546, 2696, 2697, 2705, 2708, 2713, 2730, 2746, 2754, 2767, 2768, 2773, 2822, 2855, 2856, 2908, 2911, 2918, 2966, 2978, 3011, 3018, 3036, 3038, 3102, 3113, 3197, 3205, 3206, 3269, 3272, 3418, 3435, 3456, 3468, 3547, 3555, 3576, 3594, 3605, 3609, or 3641.

In some embodiments, the composition comprises an oligonucleotide that inhibits the expression of ANGPTL4, wherein the oligonucleotide comprises an siRNA comprising a sense strand and an antisense strand, wherein the sense strand comprises the nucleoside sequence of any one of SEQ ID NOs: 36, 56, 272, 280, 289, 293, 328, 330, 331, 332, 333, 334, 337, 342, 347, 349, 435, 520, 842, 843, 876, 1001, 1002, 1157, 1164, or 1343; and/or the antisense strand comprises the nucleoside sequence of any one of SEQ ID NOs: 1890, 1910, 2126, 2134, 2143, 2147, 2182, 2184, 2185, 2186, 2187, 2188, 2191, 2196, 2201, 2203, 2289, 2374, 2696, 2697, 2730, 2855, 2856, 3011, 3018, or 3197.

In some embodiments, the siRNA comprises the sense strand and/or the antisense strand sequence of an siRNA of subset A, or a nucleic acid sequence thereof having 3 or 4 nucleoside substitutions, additions, or deletions. In some embodiments, the siRNA comprises the sense strand and/or the antisense strand sequence of an siRNA of subset A, or a nucleic acid sequence thereof having 1 or 2 nucleoside substitutions, additions, or deletions. In some embodiments, the siRNA comprises the sense strand and/or the antisense strand sequence of an siRNA of subset A. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA in Table 4, or a nucleic acid sequence thereof having 3 or 4 nucleoside substitutions, additions, or deletions. In some embodiments, the siRNA comprises the sense strand and/or the antisense strand sequence of an siRNA in Table 4, or a nucleic acid sequence thereof having 1 or 2 nucleoside substitutions, additions, or deletions. In some embodiments, the siRNA comprises the sense strand and/or the antisense strand sequence of an siRNA in Table 4. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset B, or a nucleic acid sequence thereof having 3 or 4 nucleoside substitutions, additions, or deletions. In some embodiments, the siRNA comprises the sense strand and/or the antisense strand sequence of an siRNA of subset B, or a nucleic acid sequence thereof having 1 or 2 nucleoside substitutions, additions, or deletions. In some embodiments, the siRNA comprises the sense strand and/or the antisense strand sequence of an siRNA of subset B. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset C, or a nucleic acid sequence thereof having 3 or 4 nucleoside substitutions, additions, or deletions. In some embodiments, the siRNA comprises the sense strand and/or the antisense strand sequence of an siRNA of subset C, or a nucleic acid sequence thereof having 1 or 2 nucleoside substitutions, additions, or deletions. In some embodiments, the siRNA comprises the sense strand and/or the antisense strand sequence of an siRNA of subset C. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset D, or a nucleic acid sequence thereof having 3 or 4 nucleoside substitutions, additions, or deletions. In some embodiments, the siRNA comprises the sense strand and/or the antisense strand sequence of an siRNA of subset D, or a nucleic acid sequence thereof having 1 or 2 nucleoside substitutions, additions, or deletions. In some embodiments, the siRNA comprises the sense strand and/or the antisense strand sequence of an siRNA of subset D. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset E, or a nucleic acid sequence thereof having 3 or 4 nucleoside substitutions, additions, or deletions. In some embodiments, the siRNA comprises the sense strand and/or the antisense strand sequence of an siRNA of subset E, or a nucleic acid sequence thereof having 1 or 2 nucleoside substitutions, additions, or deletions. In some embodiments, the siRNA comprises the sense strand and/or the antisense strand sequence of an siRNA of subset E. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset F, or a nucleic acid sequence thereof having 3 or 4 nucleoside substitutions, additions, or deletions. In some embodiments, the siRNA comprises the sense strand and/or the antisense strand sequence of an siRNA of subset F, or a nucleic acid sequence thereof having 1 or 2 nucleoside substitutions, additions, or deletions. In some embodiments, the siRNA comprises the sense strand and/or the antisense strand sequence of an siRNA of subset F. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA of subset G, or a nucleic acid sequence thereof having 3 or 4 nucleoside substitutions, additions, or deletions. In some embodiments, the siRNA comprises the sense strand and/or the antisense strand sequence of an siRNA of subset G, or a nucleic acid sequence thereof having 1 or 2 nucleoside substitutions, additions, or deletions. In some embodiments, the siRNA comprises the sense strand and/or the antisense strand sequence of an siRNA of subset G. In some embodiments, the siRNA is cross-reactive with a non-human primate (NHP) ANGPTL4 mRNA. The siRNA may include one or more internucleoside linkages and/or one or more nucleoside modifications.

In some embodiments, the siRNA comprises the sense strand and/or the antisense strand sequence of an siRNA in Table 5, or a nucleic acid sequence thereof having 3 or 4 nucleoside substitutions, additions, or deletions. In some embodiments, the siRNA comprises the sense strand and/or the antisense strand sequence of an siRNA in Table 5, or a nucleic acid sequence thereof having 1 or 2 nucleoside substitutions, additions, or deletions. In some embodiments, the siRNA comprises the sense strand and/or the antisense strand sequence of an siRNA in Table 5. In some embodiments, the siRNA comprises one or more of the internucleoside linkages and/or nucleoside modifications of the siRNA in Table 5. In some embodiments, the siRNA comprises the internucleoside linkages and/or nucleoside modifications of the siRNA in Table 5. In some embodiments, the siRNA is unmodified. In some embodiments, the sense strand sequence of an siRNA in Table 5 comprises modification pattern 1S. In some embodiments, the sense strand sequence of an siRNA in Table 5 comprises modification pattern 3S or 6S. In some embodiments, the sense strand sequence of an siRNA in Table 5 comprises modification pattern 1AS. In some embodiments, the sense strand sequence of an siRNA in Table 5 comprises modification pattern 4AS, 5AS, 7AS, or 8AS.

In some embodiments, the siRNA reduces an ANGPTL mRNA measurement by 10% or more, 20% or more, 30% or more, 40% or more, 50% or more, 60% or more, 70% or more, 80% or more, or 90% or more, relative to a control. In some embodiments, the siRNA reduces an ANGPTL mRNA measurement by 10% or less, 20% or less, 30% or less, 40% or less, 50% or less, 60% or less, 70% or less, 80% or less, or 90% or less, relative to a control. In some embodiments, the reduction is in a cell line such as U-138 MG cells. In some embodiments, the reduction is in response to 1 nM of the siRNA. In some embodiments, the reduction is in response to 10 nM of the siRNA.

Some siRNAs in Table 5 reduced an ANGPTL mRNA measurement by 10% or more, relative to a control. In some embodiments, the siRNA comprises the sense strand and/or the antisense strand sequence of ETD00646, ETD00648, ETD00649, ETD00651, ETD00653, ETD00654, ETD00655, ETD00656, ETD00658, ETD00660, ETD00661, ETD00662, ETD00667, ETD00669, ETD00683, ETD00684, ETD00686, ETD00688, ETD00689, ETD00691, ETD00692, ETD00694, ETD00702, ETD00709, ETD00713, ETD00714, ETD00715, ETD00716, ETD00717, ETD00719, ETD00721, ETD00726, ETD00727, ETD00728, ETD00729, ETD00730, ETD00731, ETD00733, ETD00736, ETD00738, or ETD00743, or a nucleic acid sequence thereof having 3 or 4 nucleoside substitutions, additions, or deletions. In some embodiments, the siRNA comprises the sense strand and/or the antisense strand sequence of ETD00646, ETD00648, ETD00649, ETD00651, ETD00653, ETD00654, ETD00655, ETD00656, ETD00658, ETD00660, ETD00661, ETD00662, ETD00667, ETD00669, ETD00683, ETD00684, ETD00686, ETD00688, ETD00689, ETD00691, ETD00692, ETD00694, ETD00702, ETD00709, ETD00713, ETD00714, ETD00715, ETD00716, ETD00717, ETD00719, ETD00721, ETD00726, ETD00727, ETD00728, ETD00729, ETD00730, ETD00731, ETD00733, ETD00736, ETD00738, or ETD00743, or a nucleic acid sequence thereof having 1 or 2 nucleoside substitutions, additions, or deletions. In some embodiments, the siRNA comprises the sense strand and/or the antisense strand sequence of ETD00646, ETD00648, ETD00649, ETD00651, ETD00653, ETD00654, ETD00655, ETD00656, ETD00658, ETD00660, ETD00661, ETD00662, ETD00667, ETD00669, ETD00683, ETD00684, ETD00686, ETD00688, ETD00689, ETD00691, ETD00692, ETD00694, ETD00702, ETD00709, ETD00713, ETD00714, ETD00715, ETD00716, ETD00717, ETD00719, ETD00721, ETD00726, ETD00727, ETD00728, ETD00729, ETD00730, ETD00731, ETD00733, ETD00736, ETD00738, or ETD00743. In some embodiments, the siRNA comprises one or more of the internucleoside linkages and/or nucleoside modifications of ETD00646, ETD00648, ETD00649, ETD00651, ETD00653, ETD00654, ETD00655, ETD00656, ETD00658, ETD00660, ETD00661, ETD00662, ETD00667, ETD00669, ETD00683, ETD00684, ETD00686, ETD00688, ETD00689, ETD00691, ETD00692, ETD00694, ETD00702, ETD00709, ETD00713, ETD00714, ETD00715, ETD00716, ETD00717, ETD00719, ETD00721, ETD00726, ETD00727, ETD00728, ETD00729, ETD00730, ETD00731, ETD00733, ETD00736, ETD00738, or ETD00743. In some embodiments, the siRNA comprises the internucleoside linkages and/or nucleoside modifications of ETD00646, ETD00648, ETD00649, ETD00651, ETD00653, ETD00654, ETD00655, ETD00656, ETD00658, ETD00660, ETD00661, ETD00662, ETD00667, ETD00669, ETD00683, ETD00684, ETD00686, ETD00688, ETD00689, ETD00691, ETD00692, ETD00694, ETD00702, ETD00709, ETD00713, ETD00714, ETD00715, ETD00716, ETD00717, ETD00719, ETD00721, ETD00726, ETD00727, ETD00728, ETD00729, ETD00730, ETD00731, ETD00733, ETD00736, ETD00738, or ETD00743. In some embodiments, the siRNA is unmodified.

The siRNA may comprise an unmodified version of a sense strand sequence of an siRNA listed in Table 5. In some embodiments, the siRNA of listed in Table 5 comprises any sense strand sequence of a subset A siRNA that is cross-reactive with a NHP ANGPTL4 mRNA. The siRNA may comprise an unmodified version of an antisense strand sequence of an siRNA listed in Table 5. In some embodiments, the siRNA of listed in Table 5 comprises any antisense strand sequence of a subset A siRNA that is cross-reactive with a NHP ANGPTL4 mRNA.

In some embodiments, the siRNA comprises the sense strand and/or the antisense strand sequence of an siRNA in Table 6, or a nucleic acid sequence thereof having 3 or 4 nucleoside substitutions, additions, or deletions. In some embodiments, the siRNA comprises the sense strand and/or the antisense strand sequence of an siRNA in Table 6, or a nucleic acid sequence thereof having 1 or 2 nucleoside substitutions, additions, or deletions. In some embodiments, the siRNA comprises the sense strand and/or the antisense strand sequence of an siRNA in Table 6. In some embodiments, the siRNA comprises one or more of the internucleoside linkages and/or nucleoside modifications of the siRNA in Table 6. In some embodiments, the siRNA comprises the internucleoside linkages and/or nucleoside modifications of the siRNA in Table 6. In some embodiments, the siRNA is unmodified.

The siRNA may comprise an unmodified version of an antisense strand sequence of an siRNA listed in Table 6. In some embodiments, the siRNA comprises the sense strand sequence of SEQ ID NO: 32, 570, 571, 572, 589, 607, 759, 801, 1276, 1285, 1489, 1490, 1564, 1580, 1581, 1589, 1597, 1702, 1840, or 1842, or a nucleic acid sequence thereof having 3 or 4 nucleoside substitutions, additions, or deletions. In some embodiments, the siRNA comprises the sense strand sequence of SEQ ID NO: 32, 570, 571, 572, 589, 607, 759, 801, 1276, 1285, 1489, 1490, 1564, 1580, 1581, 1589, 1597, 1702, 1840, or 1842, or a nucleic acid sequence thereof having 1 or 2 nucleoside substitutions, additions, or deletions. In some embodiments, the siRNA comprises the sense strand sequence of SEQ ID NO: 32, 570, 571, 572, 589, 607, 759, 801, 1276, 1285, 1489, 1490, 1564, 1580, 1581, 1589, 1597, 1702, 1840, or 1842. The siRNA may include the sense strand sequence of SEQ ID NO: 32, 570, 571, 572, 589, 607, 759, 801, 1276, 1285, 1489, 1490, 1564, 1580, 1581, 1589, 1597, 1702, 1840, or 1842, and one or more internucleoside linkages and/or one or more nucleoside modifications. The siRNA may include the sense strand sequence of SEQ ID NO: 32, 570, 571, 572, 589, 607, 759, 801, 1276, 1285, 1489, 1490, 1564, 1580, 1581, 1589, 1597, 1702, 1840, or 1842, and a modification pattern described herein. For example, any of the sense strands comprising the sequence of SEQ ID NO: 32, 570, 571, 572, 589, 607, 759, 801, 1276, 1285, 1489, 1490, 1564, 1580, 1581, 1589, 1597, 1702, 1840, or 1842 may in some cases comprise modification pattern 1S, 2S, 3S, or 6S.

The siRNA may comprise an unmodified version of an antisense strand sequence of an siRNA listed in Table 6. In some embodiments, the siRNA comprises the antisense strand sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696, or a nucleic acid sequence thereof having 3 or 4 nucleoside substitutions, additions, or deletions. In some embodiments, the siRNA comprises the antisense strand sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696, or a nucleic acid sequence thereof having 1 or 2 nucleoside substitutions, additions, or deletions. In some embodiments, the siRNA comprises the antisense strand sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696. The siRNA may include the antisense strand sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696, and one or more internucleoside linkages and/or one or more nucleoside modifications. The siRNA may include the antisense strand sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696, and a modification pattern described herein. For example, any of the antisense strands comprising the sequence of SEQ ID NO: 1886, 2424, 2425, 2426, 2443, 2461, 2613, 2655, 3130, 3139, 3343, 3344, 3418, 3434, 3435, 3443, 3451, 3556, 3694, or 3696 may comprise modification pattern 1AS, 3AS, 4AS, 5AS, 7AS, or 8AS.

Some siRNAs in Table 6 reduced an ANGPTL mRNA measurement by 10% or more, relative to a control. In some embodiments, the siRNA comprises the sense strand and/or the antisense strand sequence of ETD00915, ETD00916, ETD00917, ETD00921, ETD00924, ETD00925, ETD00926, ETD00927, ETD00928, ETD00929, ETD00930, ETD00931, ETD00932, ETD00933, or ETD00934, or a nucleic acid sequence thereof having 3 or 4 nucleoside substitutions, additions, or deletions. In some embodiments, the siRNA comprises the sense strand and/or the antisense strand sequence of ETD00915, ETD00916, ETD00917, ETD00921, ETD00924, ETD00925, ETD00926, ETD00927, ETD00928, ETD00929, ETD00930, ETD00931, ETD00932, ETD00933, or ETD00934, or a nucleic acid sequence thereof having 1 or 2 nucleoside substitutions, additions, or deletions. In some embodiments, the siRNA comprises the sense strand and/or the antisense strand sequence of ETD00915, ETD00916, ETD00917, ETD00921, ETD00924, ETD00925, ETD00926, ETD00927, ETD00928, ETD00929, ETD00930, ETD00931, ETD00932, ETD00933, or ETD00934. In some embodiments, the siRNA comprises one or more of the internucleoside linkages and/or nucleoside modifications of ETD00915, ETD00916, ETD00917, ETD00921, ETD00924, ETD00925, ETD00926, ETD00927, ETD00928, ETD00929, ETD00930, ETD00931, ETD00932, ETD00933, or ETD00934. In some embodiments, the siRNA comprises the internucleoside linkages and/or nucleoside modifications of ETD00915, ETD00916, ETD00917, ETD00921, ETD00924, ETD00925, ETD00926, ETD00927, ETD00928, ETD00929, ETD00930, ETD00931, ETD00932, ETD00933, or ETD00934. In some embodiments, the siRNA is unmodified.

The siRNA may comprise a sense strand sequence of an siRNA that reduced an ANGPTL mRNA measurement by 10% or more, relative to a control, in Table 5 or Table 6. In some embodiments, the siRNA comprises the sense strand sequence of any one of SEQ ID NOS: 14012, 14014, 14015, 14017, 14019, 14020, 14021, 14022, 14024, 14026, 14027, 14028, 14033, 14035, 14049, 14050, 14052, 14054, 14055, 14057, 14058, 14060, 14068, 14075, 14079, 14080, 14081, 14082, 14083, 14085, 14087, 14092, 14093, 14094, 14095, 14096, 14097, 14099, 14102, 14104, 14109, 14114, 14115, 14116, 14120, 14123, 14124, 14125, 14126, 14127, 14128, 14129, 14130, 14131, 14132, or 14133, or a nucleic acid sequence thereof having 3 or 4 nucleoside substitutions, additions, or deletions. In some embodiments, the siRNA comprises the sense strand sequence of any one of SEQ ID NOS: 14012, 14014, 14015, 14017, 14019, 14020, 14021, 14022, 14024, 14026, 14027, 14028, 14033, 14035, 14049, 14050, 14052, 14054, 14055, 14057, 14058, 14060, 14068, 14075, 14079, 14080, 14081, 14082, 14083, 14085, 14087, 14092, 14093, 14094, 14095, 14096, 14097, 14099, 14102, 14104, 14109, 14114, 14115, 14116, 14120, 14123, 14124, 14125, 14126, 14127, 14128, 14129, 14130, 14131, 14132, or 14133, ora nucleic acid sequence thereof having 1 or 2 nucleoside substitutions, additions, or deletions. In some embodiments, the siRNA comprises the sense strand sequence of any one of SEQ ID NOS: 14012, 14014, 14015, 14017, 14019, 14020, 14021, 14022, 14024, 14026, 14027, 14028, 14033, 14035, 14049, 14050, 14052, 14054, 14055, 14057, 14058, 14060, 14068, 14075, 14079, 14080, 14081, 14082, 14083, 14085, 14087, 14092, 14093, 14094, 14095, 14096, 14097, 14099, 14102, 14104, 14109, 14114, 14115, 14116, 14120, 14123, 14124, 14125, 14126, 14127, 14128, 14129, 14130, 14131, 14132, or 14133. In some embodiments, the siRNA comprises one or more of the internucleoside linkages and/or nucleoside modifications of the sense strand of 14012, 14014, 14015, 14017, 14019, 14020, 14021, 14022, 14024, 14026, 14027, 14028, 14033, 14035, 14049, 14050, 14052, 14054, 14055, 14057, 14058, 14060, 14068, 14075, 14079, 14080, 14081, 14082, 14083, 14085, 14087, 14092, 14093, 14094, 14095, 14096, 14097, 14099, 14102, 14104, 14109, 14114, 14115, 14116, 14120, 14123, 14124, 14125, 14126, 14127, 14128, 14129, 14130, 14131, 14132, or 14133. In some embodiments, the siRNA comprises the internucleoside linkages and/or nucleoside modifications of the sense strand of 14012, 14014, 14015, 14017, 14019, 14020, 14021, 14022, 14024, 14026, 14027, 14028, 14033, 14035, 14049, 14050, 14052, 14054, 14055, 14057, 14058, 14060, 14068, 14075, 14079, 14080, 14081, 14082, 14083, 14085, 14087, 14092, 14093, 14094, 14095, 14096, 14097, 14099, 14102, 14104, 14109, 14114, 14115, 14116, 14120, 14123, 14124, 14125, 14126, 14127, 14128, 14129, 14130, 14131, 14132, or 14133. In some embodiments, the siRNA is unmodified.

The siRNA may comprise an antisense strand sequence of an siRNA that reduced an ANGPTL mRNA measurement by 10% or more, relative to a control, in Table 5 or Table 6. In some embodiments, the siRNA comprises the antisense strand sequence of any one of SEQ ID NOS: 14167, 14169, 14170, 14172, 14174, 14175, 14176, 14177, 14179, 14181, 14182, 14183, 14188, 14190, 14204, 14205, 14207, 14209, 14210, 14212, 14213, 14215, 14223, 14230, 14234, 14235, 14236, 14237, 14238, 14240, 14242, 14247, 14248, 14249, 14250, 14251, 14252, 14254, 14257, 14259, 14264, 14269, 14270, 14271, 14275, 14278, 14279, 14280, 14281, 14282, 14283, 14284, 14285, 14286, 14287, or 14288, or a nucleic acid sequence thereof having 3 or 4 nucleoside substitutions, additions, or deletions. In some embodiments, the siRNA comprises the antisense strand sequence of any one of SEQ ID NOS: 14167, 14169, 14170, 14172, 14174, 14175, 14176, 14177, 14179, 14181, 14182, 14183, 14188, 14190, 14204, 14205, 14207, 14209, 14210, 14212, 14213, 14215, 14223, 14230, 14234, 14235, 14236, 14237, 14238, 14240, 14242, 14247, 14248, 14249, 14250, 14251, 14252, 14254, 14257, 14259, 14264, 14269, 14270, 14271, 14275, 14278, 14279, 14280, 14281, 14282, 14283, 14284, 14285, 14286, 14287, or 14288, or a nucleic acid sequence thereof having 1 or 2 nucleoside substitutions, additions, or deletions. In some embodiments, the siRNA comprises the antisense strand sequence of any one of SEQ ID NOS: 14167, 14169, 14170, 14172, 14174, 14175, 14176, 14177, 14179, 14181, 14182, 14183, 14188, 14190, 14204, 14205, 14207, 14209, 14210, 14212, 14213, 14215, 14223, 14230, 14234, 14235, 14236, 14237, 14238, 14240, 14242, 14247, 14248, 14249, 14250, 14251, 14252, 14254, 14257, 14259, 14264, 14269, 14270, 14271, 14275, 14278, 14279, 14280, 14281, 14282, 14283, 14284, 14285, 14286, 14287, or 14288. In some embodiments, the siRNA comprises one or more of the internucleoside linkages and/or nucleoside modifications of the antisense strand of 14167, 14169, 14170, 14172, 14174, 14175, 14176, 14177, 14179, 14181, 14182, 14183, 14188, 14190, 14204, 14205, 14207, 14209, 14210, 14212, 14213, 14215, 14223, 14230, 14234, 14235, 14236, 14237, 14238, 14240, 14242, 14247, 14248, 14249, 14250, 14251, 14252, 14254, 14257, 14259, 14264, 14269, 14270, 14271, 14275, 14278, 14279, 14280, 14281, 14282, 14283, 14284, 14285, 14286, 14287, or 14288. In some embodiments, the siRNA comprises the internucleoside linkages and/or nucleoside modifications of the antisense strand of 14167, 14169, 14170, 14172, 14174, 14175, 14176, 14177, 14179, 14181, 14182, 14183, 14188, 14190, 14204, 14205, 14207, 14209, 14210, 14212, 14213, 14215, 14223, 14230, 14234, 14235, 14236, 14237, 14238, 14240, 14242, 14247, 14248, 14249, 14250, 14251, 14252, 14254, 14257, 14259, 14264, 14269, 14270, 14271, 14275, 14278, 14279, 14280, 14281, 14282, 14283, 14284, 14285, 14286, 14287, or 14288. In some embodiments, the siRNA is unmodified.

The siRNA may comprise an unmodified version of a sense strand sequence of an siRNA that reduced an ANGPTL mRNA measurement by 10% or more, relative to a control, in Table 5 or Table 6. In some embodiments, the siRNA comprises the sense strand sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, or a nucleic acid sequence thereof having 3 or 4 nucleoside substitutions, additions, or deletions. In some embodiments, the siRNA comprises the sense strand sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, or a nucleic acid sequence thereof having 1 or 2 nucleoside substitutions, additions, or deletions. In some embodiments, the siRNA comprises the sense strand sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842. The siRNA may include the sense strand sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, and one or more internucleoside linkages and/or one or more nucleoside modifications. The siRNA may include the sense strand sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, and a modification pattern described herein (e.g. modification pattern 1S, 2S, 3S, 4S, 5S, or 6S).

The siRNA may comprise an unmodified version of an antisense strand sequence of an siRNA that reduced an ANGPTL mRNA measurement by 10% or more, relative to a control, in Table 5 or Table 6. In some embodiments, the siRNA comprises the antisense strand sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or a nucleic acid sequence thereof having 3 or 4 nucleoside substitutions, additions, or deletions. In some embodiments, the siRNA comprises the antisense strand sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or a nucleic acid sequence thereof having 1 or 2 nucleoside substitutions, additions, or deletions. In some embodiments, the siRNA comprises the antisense strand sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696. The siRNA may include the antisense strand sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, and one or more internucleoside linkages and/or one or more nucleoside modifications. The siRNA may include the antisense strand sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, and a modification pattern described herein (e.g. modification pattern 1AS, 2AS, 3AS, 4AS, 5AS, 6AS, 7AS, 8AS, or 9AS).

In some embodiments, the siRNA comprises the sense strand and/or the antisense strand sequence of an siRNA in Table 7, or a nucleic acid sequence thereof having 3 or 4 nucleoside substitutions, additions, or deletions. In some embodiments, the siRNA comprises the sense strand and/or the antisense strand sequence of an siRNA in Table 7, or a nucleic acid sequence thereof having 1 or 2 nucleoside substitutions, additions, or deletions. In some embodiments, the siRNA comprises the sense strand and/or the antisense strand sequence of an siRNA in Table 7. In some embodiments, the siRNA comprises one or more of the internucleoside linkages and/or nucleoside modifications of the siRNA in Table 7. In some embodiments, the siRNA comprises the internucleoside linkages and/or nucleoside modifications of the siRNA in Table 7. In some embodiments, the siRNA is unmodified.

In some embodiments, the siRNA comprises the sense strand and/or the antisense strand sequence of an siRNA in Table 8, or a nucleic acid sequence thereof having 3 or 4 nucleoside substitutions, additions, or deletions. In some embodiments, the siRNA comprises the sense strand and/or the antisense strand sequence of an siRNA in Table 8, or a nucleic acid sequence thereof having 1 or 2 nucleoside substitutions, additions, or deletions. In some embodiments, the siRNA comprises the sense strand and/or the antisense strand sequence of an siRNA in Table 8. In some embodiments, the siRNA comprises one or more of the internucleoside linkages and/or nucleoside modifications of the siRNA in Table 8. In some embodiments, the siRNA comprises the internucleoside linkages and/or nucleoside modifications of the siRNA in Table 8. In some embodiments, the siRNA is unmodified.

In some embodiments, the siRNA comprises the sense strand and/or the antisense strand sequence of an siRNA in Table 10, or a nucleic acid sequence thereof having 3 or 4 nucleoside substitutions, additions, or deletions. In some embodiments, the siRNA comprises the sense strand and/or the antisense strand sequence of an siRNA in Table 10, or a nucleic acid sequence thereof having 1 or 2 nucleoside substitutions, additions, or deletions. In some embodiments, the siRNA comprises the sense strand and/or the antisense strand sequence of an siRNA in Table 10. In some embodiments, the siRNA comprises one or more of the internucleoside linkages and/or nucleoside modifications of the siRNA in Table 10. In some embodiments, the siRNA comprises the internucleoside linkages and/or nucleoside modifications of the siRNA in Table 10. In some embodiments, the siRNA is unmodified.

In some embodiments, the siRNA comprises the sense strand and/or the antisense strand sequence of an siRNA in Table 15, or a nucleic acid sequence thereof having 3 or 4 nucleoside substitutions, additions, or deletions. In some embodiments, the siRNA comprises the sense strand and/or the antisense strand sequence of an siRNA in Table 15, or a nucleic acid sequence thereof having 1 or 2 nucleoside substitutions, additions, or deletions. In some embodiments, the siRNA comprises the sense strand and/or the antisense strand sequence of an siRNA in Table 15. In some embodiments, the siRNA comprises one or more of the internucleoside linkages and/or nucleoside modifications of the siRNA in Table 15. In some embodiments, the siRNA comprises the internucleoside linkages and/or nucleoside modifications of the siRNA in Table 15. In some embodiments, the siRNA is unmodified.

In some embodiments, the siRNA comprises the sense strand and/or the antisense strand sequence of an siRNA in Table 16, or a nucleic acid sequence thereof having 3 or 4 nucleoside substitutions, additions, or deletions. In some embodiments, the siRNA comprises the sense strand and/or the antisense strand sequence of an siRNA in Table 16, or a nucleic acid sequence thereof having 1 or 2 nucleoside substitutions, additions, or deletions. In some embodiments, the siRNA comprises the sense strand and/or the antisense strand sequence of an siRNA in Table 16. In some embodiments, the siRNA comprises one or more of the internucleoside linkages and/or nucleoside modifications of the siRNA in Table 16. In some embodiments, the siRNA comprises the internucleoside linkages and/or nucleoside modifications of the siRNA in Table 16. In some embodiments, the siRNA is unmodified.

In some embodiments, the sense strand comprises a nucleoside sequence at least 85% identical to any one of SEQ ID NOS: 13970-13973. In some embodiments, the sense strand comprises the nucleoside sequence of any one of SEQ ID NOS: 13970-13973, or a sense strand sequence thereof having 1 or 2 nucleoside substitutions, additions, or deletions. In some embodiments, the sense strand comprises the nucleoside sequence of any one of SEQ ID NOS: 13970-13973. The siRNA may include the sense strand sequence of any one of SEQ ID NOS: 13970-13973, and one or more internucleoside linkages and/or one or more nucleoside modifications. The siRNA may include the sense strand sequence of any one of SEQ ID NOS: 13970-13973, and a modification pattern described herein (e.g. modification pattern 1S, 2S, 3S, 4S, 5S, or 6S). The sense strand may include an overhang (e.g. a 2 nucleotide overhang such as 2 uracil nucleotides).

In some embodiments, the antisense strand comprises a nucleoside sequence at least 85% identical to any one of SEQ ID NOS: 13978-13981. In some embodiments, the antisense strand comprises the nucleoside sequence of any one of SEQ ID NOS: 13978-13981, or an antisense strand sequence thereof having 1 or 2 nucleoside substitutions, additions, or deletions. In some embodiments, the antisense strand comprises the nucleoside sequence of any one of SEQ ID NOS: 13978-13981. The siRNA may include the sense strand sequence of any one of SEQ ID NOS: 13978-13981, and one or more internucleoside linkages and/or one or more nucleoside modifications. The siRNA may include the sense strand sequence of any one of SEQ ID NOS: 13978-13981, and a modification pattern described herein (e.g. modification pattern 1AS, 2AS, 3AS, 4AS, 5AS, 6AS, 7AS, 8AS, or 9AS). The antisense strand may include an overhang (e.g. a 2 nucleotide overhang such as 2 uracil nucleotides).

In some embodiments, the sense strand comprises a nucleoside sequence at least 85% identical to any one of SEQ ID NOS: 13974-13977. In some embodiments, the sense strand comprises the nucleoside sequence of any one of SEQ ID NOS: 13974-13977, or a sense strand sequence thereof having 1 or 2 nucleoside substitutions, additions, or deletions. In some embodiments, the sense strand comprises the nucleoside sequence of any one of SEQ ID NOS: 13974-13977. The siRNA may include the sense strand sequence of any one of SEQ ID NOS: 13974-13977, and one or more internucleoside linkages and/or one or more nucleoside modifications. The siRNA may include the sense strand sequence of any one of SEQ ID NOS: 13974-13977, and a modification pattern described herein (e.g. modification pattern 1S, 2S, 3S, 4S, 5S, or 6S). The sense strand may include an overhang.

In some embodiments, the antisense strand comprises a nucleoside sequence at least 85% identical to any one of SEQ ID NOS: 13982-13985. In some embodiments, the antisense strand comprises the nucleoside sequence of any one of SEQ ID NOS: 13982-13985, or an antisense strand sequence thereof having 1 or 2 nucleoside substitutions, additions, or deletions. In some embodiments, the antisense strand comprises the nucleoside sequence of any one of SEQ ID NOS: 13982-13985. The siRNA may include the sense strand sequence of any one of SEQ ID NOS: 13982-13985, and one or more internucleoside linkages and/or one or more nucleoside modifications. The siRNA may include the sense strand sequence of any one of SEQ ID NOS: 13982-13985, and a modification pattern described herein (e.g. modification pattern 1AS, 2AS, 3AS, 4AS, 5AS, 6AS, 7AS, 8AS, or 9AS). The antisense strand may include an overhang.

In some embodiments, the sense strand and/or antisense strand comprises a nucleoside sequence at least 85% identical to the sense strand and/or antisense strand of any one of EDT01062 to ETD01065, EDT01062.1 to ETD01065.1, EDT01062.2 to ETD01065.2, EDT01062.3 to ETD01065.3, EDT01062.4 to ETD01065.4, EDT01062.5 to ETD01065.5, EDT01062.6 to ETD01065.6, EDT01062.7 to ETD01065.7, or EDT01062.8 to ETD01065.8. In some embodiments, the sense strand and/or antisense strand comprises the sense strand and/or antisense strand of any one of EDT01062 to ETD01065, EDT01062.1 to ETD01065.1, EDT01062.2 to ETD01065.2, EDT01062.3 to ETD01065.3, EDT01062.4 to ETD01065.4, EDT01062.5 to ETD01065.5, EDT01062.6 to ETD01065.6, EDT01062.7 to ETD01065.7, or EDT01062.8 to ETD01065.8, or a sense strand and/or antisense strand sequence thereof having 1 or 2 nucleoside substitutions, additions, or deletions. In some embodiments, the sense strand and/or antisense strand comprises the sense strand and/or antisense strand of any one of EDT01062 to ETD01065, EDT01062.1 to ETD01065.1, EDT01062.2 to ETD01065.2, EDT01062.3 to ETD01065.3, EDT01062.4 to ETD01065.4, EDT01062.5 to ETD01065.5, EDT01062.6 to ETD01065.6, EDT01062.7 to ETD01065.7, or EDT01062.8 to ETD01065.8. The sense strand and/or antisense strand may comprise a GalNAc ligand. The sense strand and/or antisense strand may exclude any GalNAc ligand.

The sense strand may comprise the nucleoside sequence of SEQ ID NO: 13973, or a derivative thereof. In some embodiments, the sense strand comprises a nucleoside sequence at least 85% identical to SEQ ID NO: 13973. The sense strand comprising the nucleoside sequence of SEQ ID NO: 13973, or derivative thereof, may include the sense strand comprising a nucleoside sequence at least 85% identical to SEQ ID NO: 13973. In some embodiments, the sense strand comprises the nucleoside sequence of SEQ ID NO: 13973, or a sense strand sequence thereof having 1 or 2 nucleoside substitutions, additions, or deletions. The sense strand comprising the nucleoside sequence of SEQ ID NO: 13973 derivative may include the sense strand comprising a nucleoside sequence having 1 or 2 nucleoside substitutions, additions, or deletions. In some embodiments, the sense strand comprises the nucleoside sequence of SEQ ID NO: 13973. The sense strand sequence may consist of the nucleotide sequence of SEQ ID NO: 13973. The sense strand comprising the nucleoside sequence of SEQ ID NO: 13973, or derivative thereof, may include a GalNAc ligand (e.g. attached to a 3' or 5' end). The sense strand comprising the nucleoside sequence of SEQ ID NO: 13973, or derivative thereof, may include a 2 nucleotide overhang. The sense strand comprising the nucleoside sequence of SEQ ID NO: 13973, or derivative thereof, may include modification pattern 1S. The sense strand comprising the nucleoside sequence of SEQ ID NO: 13973, or derivative thereof, may include modification pattern 2S. The sense strand comprising the nucleoside sequence of SEQ ID NO: 13973, or derivative thereof, may include modification pattern 3S. The sense strand comprising the nucleoside sequence of SEQ ID NO: 13973, or derivative thereof, may include modification pattern 4S. The sense strand comprising the nucleoside sequence of SEQ ID NO: 13973, or derivative thereof, may include modification pattern 5S. The sense strand comprising the nucleoside sequence of SEQ ID NO: 13973, or derivative thereof, may include modification pattern 6S.

The sense strand may comprise the nucleoside sequence of SEQ ID NO: 13977, or a derivative thereof. In some embodiments, the sense strand comprises a nucleoside sequence at least 85% identical to SEQ ID NO: 13977. The sense strand comprising the nucleoside sequence of SEQ ID NO: 13977, or derivative thereof, may include the sense strand comprising a nucleoside sequence at least 85% identical to SEQ ID NO: 13977. In some embodiments, the sense strand comprises the nucleoside sequence of SEQ ID NO: 13977, or a sense strand sequence thereof having 1 or 2 nucleoside substitutions, additions, or deletions. The sense strand comprising the nucleoside sequence of SEQ ID NO: 13977 derivative may include the sense strand comprising a nucleoside sequence having 1 or 2 nucleoside substitutions, additions, or deletions. In some embodiments, the sense strand comprises the nucleoside sequence of SEQ ID NO: 13977. The sense strand sequence may consist of the nucleotide sequence of SEQ ID NO: 13977. The sense strand comprising the nucleoside sequence of SEQ ID NO: 13977, or derivative thereof, may include a GalNAc ligand (e.g. attached to a 3' or 5' end). The sense strand comprising the nucleoside sequence of SEQ ID NO: 13977, or derivative thereof, may include a 2 nucleotide overhang. The sense strand comprising the nucleoside sequence of SEQ ID NO: 13977, or derivative thereof, may include modification pattern 1S. The sense strand comprising the nucleoside sequence of SEQ ID NO: 13977, or derivative thereof, may include modification pattern 2S. The sense strand comprising the nucleoside sequence of SEQ ID NO: 13977, or derivative thereof, may include modification pattern 3S. The sense strand comprising the nucleoside sequence of SEQ ID NO: 13977, or derivative thereof, may include modification pattern 4S. The sense strand comprising the nucleoside sequence of SEQ ID NO: 13977, or derivative thereof, may include modification pattern 5S. The sense strand comprising the nucleoside sequence of SEQ ID NO: 13977, or derivative thereof, may include modification pattern 6S.

The antisense strand may comprise the nucleoside sequence of SEQ ID NO: 13981, or a derivative thereof. In some embodiments, the antisense strand comprises a nucleoside sequence at least 85% identical to SEQ ID NO: 13981. The antisense strand comprising the nucleoside sequence of SEQ ID NO: 13981, or derivative thereof, may include the antisense strand comprising a nucleoside sequence at least 85% identical to SEQ ID NO: 13981. In some embodiments, the antisense strand comprises the nucleoside sequence of SEQ ID NO: 13981, or an antisense strand sequence thereof having 1 or 2 nucleoside substitutions, additions, or deletions. The antisense strand comprising the nucleoside sequence of SEQ ID NO: 13981 derivative may include the antisense strand comprising a nucleoside sequence having 1 or 2 nucleoside substitutions, additions, or deletions. In some embodiments, the antisense strand comprises the nucleoside sequence of SEQ ID NO: 13981. The antisense strand sequence may consist of the nucleotide sequence of SEQ ID NO: 13981. The antisense strand comprising the nucleoside sequence of SEQ ID NO: 13981, or derivative thereof, may include a GalNAc ligand (e.g. attached to a 3' or 5' end). The antisense strand comprising the nucleoside sequence of SEQ ID NO: 13981, or derivative thereof, may include a 2 nucleotide overhang. The antisense strand comprising the nucleoside sequence of SEQ ID NO: 13981, or derivative thereof, may include modification pattern 1AS. The antisense strand comprising the nucleoside sequence of SEQ ID NO: 13981, or derivative thereof, may include modification pattern 2AS. The antisense strand comprising the nucleoside sequence of SEQ ID NO: 13981, or derivative thereof, may include modification pattern 3AS. The antisense strand comprising the nucleoside sequence of SEQ ID NO: 13981, or derivative thereof, may include modification pattern 4AS. The antisense strand comprising the nucleoside sequence of SEQ ID NO: 13981, or derivative thereof, may include modification pattern 5AS. The antisense strand comprising the nucleoside sequence of SEQ ID NO: 13981, or derivative thereof, may include modification pattern 6AS. The antisense strand comprising the nucleoside sequence of SEQ ID NO: 13981, or derivative thereof, may include modification pattern 7AS. The antisense strand comprising the nucleoside sequence of SEQ ID NO: 13981, or derivative thereof, may include modification pattern 8AS. The antisense strand comprising the nucleoside sequence of SEQ ID NO: 13981, or derivative thereof, may include modification pattern 9AS.

The antisense strand may comprise the nucleoside sequence of SEQ ID NO: 13985, or a derivative thereof. In some embodiments, the antisense strand comprises a nucleoside sequence at least 85% identical to SEQ ID NO: 13985. The antisense strand comprising the nucleoside sequence of SEQ ID NO: 13985, or derivative thereof, may include the antisense strand comprising a nucleoside sequence at least 85% identical to SEQ ID NO: 13985. In some embodiments, the antisense strand comprises the nucleoside sequence of SEQ ID NO: 13985, or an antisense strand sequence thereof having 1 or 2 nucleoside substitutions, additions, or deletions. The antisense strand comprising the nucleoside sequence of SEQ ID NO: 13985 derivative may include the antisense strand comprising a nucleoside sequence having 1 or 2 nucleoside substitutions, additions, or deletions. In some embodiments, the antisense strand comprises the nucleoside sequence of SEQ ID NO: 13985. The antisense strand sequence may consist of the nucleotide sequence of SEQ ID NO: 13985. The antisense strand comprising the nucleoside sequence of SEQ ID NO: 13985, or derivative thereof, may include a GalNAc ligand (e.g. attached to a 3' or 5' end). The antisense strand comprising the nucleoside sequence of SEQ ID NO: 13985, or derivative thereof, may include a 2 nucleotide overhang. The antisense strand comprising the nucleoside sequence of SEQ ID NO: 13985, or derivative thereof, may include modification pattern 1AS. The antisense strand comprising the nucleoside sequence of SEQ ID NO: 13985, or derivative thereof, may include modification pattern 2AS. The antisense strand comprising the nucleoside sequence of SEQ ID NO: 13985, or derivative thereof, may include modification pattern 3AS. The antisense strand comprising the nucleoside sequence of SEQ ID NO: 13985, or derivative thereof, may include modification pattern 4AS. The antisense strand comprising the nucleoside sequence of SEQ ID NO: 13985, or derivative thereof, may include modification pattern 5AS. The antisense strand comprising the nucleoside sequence of SEQ ID NO: 13985, or derivative thereof, may include modification pattern 6AS. The antisense strand comprising the nucleoside sequence of SEQ ID NO: 13985, or derivative thereof, may include modification pattern 7AS. The antisense strand comprising the nucleoside sequence of SEQ ID NO: 13985, or derivative thereof, may include modification pattern 8AS. The antisense strand comprising the nucleoside sequence of SEQ ID NO: 13985, or derivative thereof, may include modification pattern 9AS.

In some embodiments, the sense strand comprises a nucleoside sequence at least 85% identical to any one of SEQ ID NOS: 14006-14011. In some embodiments, the sense strand comprises the nucleoside sequence of any one of SEQ ID NOS: 14006-14011, or a sense strand sequence thereof having 1 or 2 nucleoside substitutions, additions, or deletions. In some embodiments, the sense strand comprises the nucleoside sequence of any one of SEQ ID NOS: 14006-14011. The sense strand may comprise a GalNAc ligand. In some embodiments, the antisense strand comprises a nucleoside sequence at least 85% identical to any one of SEQ ID NOS: 14158-14166. In some embodiments, the antisense strand comprises the nucleoside sequence of any one of SEQ ID NOS: 14158-14166, or an antisense strand sequence thereof having 1 or 2 nucleoside substitutions, additions, or deletions. In some embodiments, the antisense strand comprises the nucleoside sequence of any one of SEQ ID NOS: 14158-14166. The antisense strand may comprise a GalNAc ligand.

In some embodiments, the siRNA a sense strand comprising the sequence of SEQ ID NO: 13970, or a nucleic acid sequence thereof having 3 or 4 nucleoside substitutions, additions, or deletions. In some embodiments, the siRNA a sense strand comprising the sequence of SEQ ID NO: 13970, or a nucleic acid sequence thereof having 1 or 2 nucleoside substitutions, additions, or deletions. In some embodiments, the siRNA a sense strand comprising the sequence of SEQ ID NO: 13970. In some embodiments, the sense strand comprises one or more internucleoside linkages and/or nucleoside modifications. In some embodiments, the siRNA an antisense strand comprising the sequence of SEQ ID NO: 13978, or a nucleic acid sequence thereof having 3 or 4 nucleoside substitutions, additions, or deletions. In some embodiments, the siRNA an antisense strand comprising the sequence of SEQ ID NO: 13978, or a nucleic acid sequence thereof having 1 or 2 nucleoside substitutions, additions, or deletions. In some embodiments, the siRNA an antisense strand comprising the sequence of SEQ ID NO: 13978. In some embodiments, the antisense strand comprises one or more internucleoside linkages and/or nucleoside modifications.

In some embodiments, the siRNA a sense strand comprising the sequence of SEQ ID NO: 13971, or a nucleic acid sequence thereof having 3 or 4 nucleoside substitutions, additions, or deletions. In some embodiments, the siRNA a sense strand comprising the sequence of SEQ ID NO: 13971, or a nucleic acid sequence thereof having 1 or 2 nucleoside substitutions, additions, or deletions. In some embodiments, the siRNA a sense strand comprising the sequence of SEQ ID NO: 13971. In some embodiments, the sense strand comprises one or more internucleoside linkages and/or nucleoside modifications. In some embodiments, the siRNA an antisense strand comprising the sequence of SEQ ID NO: 13979, or a nucleic acid sequence thereof having 3 or 4 nucleoside substitutions, additions, or deletions. In some embodiments, the siRNA an antisense strand comprising the sequence of SEQ ID NO: 13979, or a nucleic acid sequence thereof having 1 or 2 nucleoside substitutions, additions, or deletions. In some embodiments, the siRNA an antisense strand comprising the sequence of SEQ ID NO: 13979. In some embodiments, the antisense strand comprises one or more internucleoside linkages and/or nucleoside modifications.

In some embodiments, the siRNA a sense strand comprising the sequence of SEQ ID NO: 13972, or a nucleic acid sequence thereof having 3 or 4 nucleoside substitutions, additions, or deletions. In some embodiments, the siRNA a sense strand comprising the sequence of SEQ ID NO: 13972, or a nucleic acid sequence thereof having 1 or 2 nucleoside substitutions, additions, or deletions. In some embodiments, the siRNA a sense strand comprising the sequence of SEQ ID NO: 13972. In some embodiments, the sense strand comprises one or more internucleoside linkages and/or nucleoside modifications. In some embodiments, the siRNA an antisense strand comprising the sequence of SEQ ID NO: 13980, or a nucleic acid sequence thereof having 3 or 4 nucleoside substitutions, additions, or deletions. In some embodiments, the siRNA an antisense strand comprising the sequence of SEQ ID NO: 13980, or a nucleic acid sequence thereof having 1 or 2 nucleoside substitutions, additions, or deletions. In some embodiments, the siRNA an antisense strand comprising the sequence of SEQ ID NO: 13980. In some embodiments, the antisense strand comprises one or more internucleoside linkages and/or nucleoside modifications.

In some embodiments, the siRNA a sense strand comprising the sequence of SEQ ID NO: 13973, or a nucleic acid sequence thereof having 3 or 4 nucleoside substitutions, additions, or deletions. In some embodiments, the siRNA a sense strand comprising the sequence of SEQ ID NO: 13973, or a nucleic acid sequence thereof having 1 or 2 nucleoside substitutions, additions, or deletions. In some embodiments, the siRNA a sense strand comprising the sequence of SEQ ID NO: 13973. In some embodiments, the sense strand comprises one or more internucleoside linkages and/or nucleoside modifications. In some embodiments, the siRNA an antisense strand comprising the sequence of SEQ ID NO: 13981, or a nucleic acid sequence thereof having 3 or 4 nucleoside substitutions, additions, or deletions. In some embodiments, the siRNA an antisense strand comprising the sequence of SEQ ID NO: 13981, or a nucleic acid sequence thereof having 1 or 2 nucleoside substitutions, additions, or deletions. In some embodiments, the siRNA an antisense strand comprising the sequence of SEQ ID NO: 13981. In some embodiments, the antisense strand comprises one or more internucleoside linkages and/or nucleoside modifications.

In some embodiments, the siRNA a sense strand comprising the sequence of SEQ ID NO: 1285, or a nucleic acid sequence thereof having 3 or 4 nucleoside substitutions, additions, or deletions. In some embodiments, the siRNA a sense strand comprising the sequence of SEQ ID NO: 1285, or a nucleic acid sequence thereof having 1 or 2 nucleoside substitutions, additions, or deletions. In some embodiments, the siRNA a sense strand comprising the sequence of SEQ ID NO: 1285. In some embodiments, the sense strand comprises one or more internucleoside linkages and/or nucleoside modifications. In some embodiments, the siRNA an antisense strand comprising the sequence of SEQ ID NO: 3139, or a nucleic acid sequence thereof having 3 or 4 nucleoside substitutions, additions, or deletions. In some embodiments, the siRNA an antisense strand comprising the sequence of SEQ ID NO: 3139, or a nucleic acid sequence thereof having 1 or 2 nucleoside substitutions, additions, or deletions. In some embodiments, the siRNA an antisense strand comprising the sequence of SEQ ID NO: 3139. In some embodiments, the antisense strand comprises one or more internucleoside linkages and/or nucleoside modifications.

In some embodiments, the siRNA a sense strand comprising the sequence of SEQ ID NO: 1580, or a nucleic acid sequence thereof having 3 or 4 nucleoside substitutions, additions, or deletions. In some embodiments, the siRNA a sense strand comprising the sequence of SEQ ID NO: 1580, or a nucleic acid sequence thereof having 1 or 2 nucleoside substitutions, additions, or deletions. In some embodiments, the siRNA a sense strand comprising the sequence of SEQ ID NO: 1580. In some embodiments, the sense strand comprises one or more internucleoside linkages and/or nucleoside modifications. In some embodiments, the siRNA an antisense strand comprising the sequence of SEQ ID NO: 3434, or a nucleic acid sequence thereof having 3 or 4 nucleoside substitutions, additions, or deletions. In some embodiments, the siRNA an antisense strand comprising the sequence of SEQ ID NO: 3434, or a nucleic acid sequence thereof having 1 or 2 nucleoside substitutions, additions, or deletions. In some embodiments, the siRNA an antisense strand comprising the sequence of SEQ ID NO: 3434. In some embodiments, the antisense strand comprises one or more internucleoside linkages and/or nucleoside modifications.

In some embodiments, the siRNA a sense strand comprising the sequence of SEQ ID NO: 13974, or a nucleic acid sequence thereof having 3 or 4 nucleoside substitutions, additions, or deletions. In some embodiments, the siRNA a sense strand comprising the sequence of SEQ ID NO: 13974, or a nucleic acid sequence thereof having 1 or 2 nucleoside substitutions, additions, or deletions. In some embodiments, the siRNA a sense strand comprising the sequence of SEQ ID NO: 13974. In some embodiments, the sense strand comprises one or more internucleoside linkages and/or nucleoside modifications. In some embodiments, the siRNA an antisense strand comprising the sequence of SEQ ID NO: 13982, or a nucleic acid sequence thereof having 3 or 4 nucleoside substitutions, additions, or deletions. In some embodiments, the siRNA an antisense strand comprising the sequence of SEQ ID NO: 13982, or a nucleic acid sequence thereof having 1 or 2 nucleoside substitutions, additions, or deletions. In some embodiments, the siRNA an antisense strand comprising the sequence of SEQ ID NO: 13982. In some embodiments, the antisense strand comprises one or more internucleoside linkages and/or nucleoside modifications.

In some embodiments, the siRNA a sense strand comprising the sequence of SEQ ID NO: 13975, or a nucleic acid sequence thereof having 3 or 4 nucleoside substitutions, additions, or deletions. In some embodiments, the siRNA a sense strand comprising the sequence of SEQ ID NO:

13975, or a nucleic acid sequence thereof having 1 or 2 nucleoside substitutions, additions, or deletions. In some embodiments, the siRNA a sense strand comprising the sequence of SEQ ID NO: 13975. In some embodiments, the sense strand comprises one or more internucleoside linkages and/or nucleoside modifications. In some embodiments, the siRNA an antisense strand comprising the sequence of SEQ ID NO: 13983, or a nucleic acid sequence thereof having 3 or 4 nucleoside substitutions, additions, or deletions. In some embodiments, the siRNA an antisense strand comprising the sequence of SEQ ID NO: 13983, or a nucleic acid sequence thereof having 1 or 2 nucleoside substitutions, additions, or deletions. In some embodiments, the siRNA an antisense strand comprising the sequence of SEQ ID NO: 13983. In some embodiments, the antisense strand comprises one or more internucleoside linkages and/or nucleoside modifications.

In some embodiments, the siRNA a sense strand comprising the sequence of SEQ ID NO: 13976, or a nucleic acid sequence thereof having 3 or 4 nucleoside substitutions, additions, or deletions. In some embodiments, the siRNA a sense strand comprising the sequence of SEQ ID NO: 13976, or a nucleic acid sequence thereof having 1 or 2 nucleoside substitutions, additions, or deletions. In some embodiments, the siRNA a sense strand comprising the sequence of SEQ ID NO: 13976. In some embodiments, the sense strand comprises one or more internucleoside linkages and/or nucleoside modifications. In some embodiments, the siRNA an antisense strand comprising the sequence of SEQ ID NO: 13984, or a nucleic acid sequence thereof having 3 or 4 nucleoside substitutions, additions, or deletions. In some embodiments, the siRNA an antisense strand comprising the sequence of SEQ ID NO: 13984, or a nucleic acid sequence thereof having 1 or 2 nucleoside substitutions, additions, or deletions. In some embodiments, the siRNA an antisense strand comprising the sequence of SEQ ID NO: 13984. In some embodiments, the antisense strand comprises one or more internucleoside linkages and/or nucleoside modifications.

In some embodiments, the siRNA a sense strand comprising the sequence of SEQ ID NO: 13977, or a nucleic acid sequence thereof having 3 or 4 nucleoside substitutions, additions, or deletions. In some embodiments, the siRNA a sense strand comprising the sequence of SEQ ID NO: 13977, or a nucleic acid sequence thereof having 1 or 2 nucleoside substitutions, additions, or deletions. In some embodiments, the siRNA a sense strand comprising the sequence of SEQ ID NO: 13977. In some embodiments, the sense strand comprises one or more internucleoside linkages and/or nucleoside modifications. In some embodiments, the siRNA an antisense strand comprising the sequence of SEQ ID NO: 13985, or a nucleic acid sequence thereof having 3 or 4 nucleoside substitutions, additions, or deletions. In some embodiments, the siRNA an antisense strand comprising the sequence of SEQ ID NO: 13985, or a nucleic acid sequence thereof having 1 or 2 nucleoside substitutions, additions, or deletions. In some embodiments, the siRNA an antisense strand comprising the sequence of SEQ ID NO: 13985. In some embodiments, the antisense strand comprises one or more internucleoside linkages and/or nucleoside modifications.

In some embodiments, the composition comprises an oligonucleotide that inhibits the expression of ANGPTL4, wherein the oligonucleotide comprises an siRNA comprising a sense strand and an antisense strand, wherein the antisense strand comprises a seed region that is not identical to a seed region of a human miRNA. In some embodiments, the composition comprises an oligonucleotide that inhibits the expression of ANGPTL4, wherein the oligonucleotide comprises an siRNA comprising a sense strand and an antisense strand, wherein the sense strand comprises a seed region that is not identical to a seed region of a human miRNA. In some embodiments, the siRNA is cross-reactive with a non-human primate (NHP) ANGPTL4 mRNA. For example, the antisense strand may bind to, or be complementary with, the NHP ANGPTL4 mRNA.

B. ASOs

In some embodiments, the composition comprises an oligonucleotide that inhibits the expression of ANGPTL4, wherein the oligonucleotide comprises an antisense oligonucleotide (ASO). In some embodiments, the ASO is 12-30 nucleosides in length. In some embodiments, the ASO is 14-30 nucleosides in length. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length.

In some embodiments, the composition comprises an oligonucleotide that inhibits the expression of ANGPTL4, wherein the oligonucleotide comprises an antisense oligonucleotide (ASO) about 12-30 nucleosides in length and comprising a nucleoside sequence complementary to about 12-30 contiguous nucleosides of a full-length human ANGPTL4 mRNA sequence such as SEQ ID NO: 13935; wherein (i) the oligonucleotide comprises a modification comprising a modified nucleoside and/or a modified internucleoside linkage, and/or (ii) the composition comprises a pharmaceutically acceptable carrier.

In some embodiments, the composition comprises an oligonucleotide that inhibits the expression of ANGPTL4, wherein the oligonucleotide comprises an ASO about 12-30 nucleosides in length and comprising a nucleoside sequence complementary to about 12-30 contiguous nucleosides of a full-length human ANGPTL4 mRNA sequence such as SEQ ID NO: 13936; wherein (i) the oligonucleotide comprises a modification comprising a modified nucleoside and/or a modified internucleoside linkage, and/or (ii) the composition comprises a pharmaceutically acceptable carrier.

In some embodiments, the composition comprises an oligonucleotide that inhibits the expression of ANGPTL4, wherein the oligonucleotide comprises an ASO that comprises a nucleoside sequence comprising or consisting of the sequence of any one of SEQ ID NOs: 3709-13934. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions. In some embodiments, the ASO comprises a nucleoside sequence comprising or consisting of the sequence of any one of SEQ ID NOs: 3709-13934, or a nucleic acid sequence thereof having 3 or 4 nucleoside substitutions, additions, or deletions.

C. Modification Patterns

In some embodiments, the composition comprises an oligonucleotide that inhibits the expression of ANGPTL4, wherein the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. Benefits of the modified internucleoside linkage may include decreased toxicity or improved pharmacokinetics.

In some embodiments, the composition comprises an oligonucleotide that inhibits the expression of ANGPTL4, wherein the oligonucleotide comprises a modified internucleoside linkage, wherein the oligonucleotide comprises 1, 2, 3, 4, 5, 6, 7, 8, 9, 10, 11, 12, 13, 14, 15, 16, 17, 18, 19, or 20 modified internucleoside linkages, or a range of modified internucleoside linkages defined by any two of the aforementioned numbers. In some embodiments, the oligonucleotide comprises no more than 18 modified internucleoside linkages. In some embodiments, the oligonucleotide comprises no more than 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

In some embodiments, the composition comprises an oligonucleotide that inhibits the expression of ANGPTL4, wherein the oligonucleotide comprises the modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises HLA. In some embodiments, the modified nucleoside comprises CeNA. In some embodiments, the modified nucleoside comprises a 2'-methoxyethyl group. In some embodiments, the modified nucleoside comprises a 2'-O-alkyl group. In some embodiments, the modified nucleoside comprises a 2'-O-allyl group. In some embodiments, the modified nucleoside comprises a 2'-fluoro group. In some embodiments, the modified nucleoside comprises a 2'-deoxy group. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises a 2'-O-methyl nucleoside. In some embodiments, the modified nucleoside comprises a 2'-deoxyfluoro nucleoside. In some embodiments, the modified nucleoside comprises a 2'-O-NMA nucleoside. In some embodiments, the modified nucleoside comprises a 2'-O-DMAEOE nucleoside. In some embodiments, the modified nucleoside comprises a 2'-O-aminopropyl (2'-O-AP) nucleoside. In some embodiments, the modified nucleoside comprises 2'-ara-F. In some embodiments, the modified nucleoside comprises one or more 2'fluoro modified nucleosides. In some embodiments, the modified nucleoside comprises a 2' O-alkyl modified nucleoside. Benefits of the modified nucleoside may include decreased toxicity or improved pharmacokinetics.

In some embodiments, the oligonucleotide comprises 1, 2, 3, 4, 5, 6, 7, 8, 9, 10, 11, 12, 13, 14, 15, 16, 17, 18, 19, 20, or 21 modified nucleosides, or a range of nucleosides defined by any two of the aforementioned numbers. In some embodiments, the oligonucleotide comprises no more than 19 modified nucleosides. In some embodiments, the oligonucleotide comprises no more than 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

In some embodiments, the composition comprises an oligonucleotide that inhibits the expression of ANGPTL4, wherein the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof.

In some embodiments, the composition comprises an oligonucleotide that inhibits the expression of ANGPTL4, wherein the oligonucleotide comprises an N-acetylgalactosamine (GalNAc) ligand for hepatocyte targeting. A "GalNAc ligand" may be refer to a ligand for an asialoglycoprotein receptor (e.g. on a hepatocyte) that comprises one or more GalNAc moieties. The GalNAc ligand may bind an asialoglycoprotein receptor (e.g. on a hepatocyte). The GalNAc ligand may comprise one or more GalNAc moieties. An example of a GalNAc moiety includes GalNAc attached to a linker. The GalNAc ligand may comprise 3 GalNAc moieties. The GalNAc ligand may comprise 1, 2, 3, 4, 5, 6, 7, 8, 9, or 10, or more GalNAc moieties.

The GalNAc ligand may be conjugated to the oligonucleotide. The GalNAc ligand may be conjugated to a 5' end of the oligonucleotide. The GalNAc ligand may be conjugated to a 3' end of the oligonucleotide. A first GalNAc ligand may be conjugated to a 5' end of the oligonucleotide, and a second GalNAc ligand may be conjugated to 3' end of the oligonucleotide. The GalNAc ligand may be conjugated to a 3' or 5' end of an ASO. The GalNAc ligand may be conjugated to a 3' or 5' end of a sense strand of an siRNA. The GalNAc ligand may be conjugated to a 3' end of a sense strand of an siRNA. The GalNAc ligand may be conjugated to a 5' end of a sense strand of an siRNA. The GalNAc ligand may be conjugated to a 3' or 5' end of an antisense strand of an siRNA. The GalNAc ligand may be conjugated to a 3' end of an antisense strand of an siRNA. The GalNAc ligand may be conjugated to a 5' end of an antisense strand of an siRNA.

A first GalNAc ligand may be conjugated to a sense strand of an siRNA, and a second GalNAc ligand may be conjugated to an antisense strand of the siRNA.

1. siRNA Modification Patterns

In some embodiments, the sense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, or 29 modified internucleoside linkages, or a range of modified internucleoside linkages defined by any two of the aforementioned integers. In some embodiments, the sense strand comprises 1-11 modified internucleoside linkages. In some embodiments, the sense strand comprises 2-6 modified internucleoside linkages. In some embodiments, the sense strand comprises 5 modified internucleoside linkages. In some embodiments, the sense strand comprises 4 modified internucleoside linkages.

In some embodiments, the antisense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, or 29 modified internucleoside linkages, or a range of modified internucleoside linkages defined by any two of the aforementioned integers. In some embodiments, the antisense strand comprises 1-11 modified internucleoside linkages. In some embodiments, the antisense strand comprises 2-6 modified internucleoside linkages. In some embodiments, the antisense strand comprises 5 modified internucleoside linkages. In some embodiments, the antisense strand comprises 4 modified internucleoside linkages.

In some embodiments, the sense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 modified nucleosides, or a range of modified nucleosides defined by any two of the aforementioned integers. In some embodiments, the sense strand comprises 12-19 modified nucleosides. In some embodiments, the sense strand comprises 12-21 modified nucleosides. In some embodiments, the sense strand comprises 19 modified nucleosides. In some embodiments, the sense strand comprises 21 modified nucleosides.

In some embodiments, the antisense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 modified nucleosides, or a range of modified nucleosides defined by any two of the aforementioned integers. In some embodiments, the antisense strand comprises 12-19 modified nucleosides. In some embodiments, the antisense strand comprises 12-21 modified nucleosides. In some embodiments, the antisense strand comprises 19 modified nucleosides. In some embodiments, the antisense strand comprises 21 modified nucleosides.

In some embodiments, the sense strand or the antisense strand further comprises at least 2 additional nucleosides attached to a 3' terminus of the sense strand or the antisense strand. In some embodiments, the sense strand or the antisense strand comprises 2 additional nucleosides attached to a 3' terminus of the sense strand or the antisense strand. As part of the sense strand, the additional nucleosides may or may not be complementary to an ANGPTL4 mRNA. The additional nucleosides of the antisense strand may include a uracil. The 2 additional nucleosides of the antisense strand may both include uracil.

In some embodiments, the sense strand or the sense strand further comprises at least 2 additional nucleosides attached to a 3' terminus of the sense strand or the sense strand. In some embodiments, the sense strand or the sense strand comprises 2 additional nucleosides attached to a 3' terminus of the sense strand or the sense strand. The additional nucleosides of the sense strand may include a uracil. The 2 additional nucleosides of the sense strand may both include uracil.

In some embodiments, the composition comprises an oligonucleotide that inhibits the expression of ANGPTL4 wherein the oligonucleotide comprises an siRNA comprising a sense strand and an antisense strand, wherein the sense strand comprises modification pattern 1S: 5'-NfsnsNfnNfnNfNfNfnNfnNfnNfnNfnNfsnsn-3' (SEQ ID NO: 13954), wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5'-nsnsnnNfnNffNfnnnnnnnnnnsnsn-3' (SEQ ID NO: 13955), wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5'-nsnsnnNfnNfnNfnnnnnnnnnsnsn-3' (SEQ ID NO: 13956), wherein "Nf" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfnNfnNfNfnNfnNfnNfnNfsnsnN-3' (SEQ ID NO: 13957), wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 5S: 5'-nsnsnnNfnNfNfNfnnnnnnnnnsnsnN-3' (SEQ ID NO: 13958), wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 6S: 5'-NfsnsNfnNfnNfnNfnNfnNfnNfnNfsnsn-3' (SEQ ID NO: 13959), wherein "Nf" is a 2' fluoro-modified nucleoside, "n" is a 2' O-methyl modified nucleoside, "s" is a phosphorothioate linkage, and N comprises one or more nucleosides. Any one of modification patterns 1S-6S may include a GalNAc ligand attached to the 3' end. Any one of modification patterns 1S-6S may include a GalNAc ligand attached to the 5' end.

In some embodiments, the composition comprises an oligonucleotide that inhibits the expression of ANGPTL4 wherein the oligonucleotide comprises an siRNA comprising a sense strand and an antisense strand, wherein the antisense strand comprises modification pattern 1AS: 5'-nsNfsnNfnNfnNfnNfnNfrmnNfnNfnNfsnsn-3' (SEQ ID NO: 13960), wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnnnNfnNfNfnnnnNfnNfnnnsnsn-3' (SEQ ID NO: 13961), wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsNfsnnnNfnnnnnnnNfnNfnnnsnsn-3' (SEQ ID NO: 13962), wherein "Nf" is a 2' fluoro-modified nucleoside, "n" is a 2' O-methyl modified nucleoside, and "s" is a phosphorothioate linkage. In some embodiments, the antisense strand comprises modification pattern 4AS: 5'-nsNfsnNfnNfnnnnnnnNfnNfnnnsnsn-3' (SEQ ID NO: 13963), wherein "Nf" is a 2' fluoro-modified nucleoside, "n" is a 2' O-methyl modified nucleoside, and "s" is a phosphorothioate linkage. In some embodiments, the antisense strand comprises modification pattern 5AS: 5'-nsNfsnnnNfnNfnNfnnnnnNfnNfnnnsnsn-3' (SEQ ID NO: 13964), wherein "Nf" is a 2' fluoro-modified nucleoside, "n" is a 2' O-methyl modified nucleoside, and "s" is a phosphorothioate linkage. In some embodiments, the antisense strand comprises modification pattern 6AS: 5'-nsNfsnNfnNfnNfnNfnNfnNfnNfnNfnsnsn-3' (SEQ ID NO: 13965), wherein "Nf" is a 2' fluoro-modified nucleoside, "n" is a 2' O-methyl modified nucleoside, and "s" is a phosphorothioate linkage. In some embodiments, the antisense strand comprises modification pattern 7AS: 5'-nsNfsnNfnNfnNfnNfNfnnnnNfnNfnnnsnsn-3' (SEQ ID NO: 13966), wherein "Nf" is a 2' fluoro-modified nucleoside, "n" is a 2' O-methyl modified nucleoside, and "s" is a phosphorothioate linkage. In some embodiments, the antisense strand comprises modification pattern 8AS: 5'-nsNfsnnnnnnnnnnnnNfnrmnnsnsn-3' (SEQ ID NO: 13967), wherein "Nf" is a 2' fluoro-modified nucleoside, "n" is a 2' O-methyl modified nucleoside, and "s" is a phosphorothioate linkage. In some embodiments, the antisense strand comprises modification pattern 9AS: 5'-nsNfsnnnNfnnnnnnnnNfnNfnNfnsnsn-3' (SEQ ID NO: 13968), wherein "Nf" is a 2' fluoro-modified nucleoside, "n" is a 2' O-methyl modified nucleoside, and "s" is a phosphorothioate linkage. Any one of modification patterns 1AS-9AS may include a GalNAc ligand attached to the 3' end. Any one of modification patterns 1AS-9AS may include a GalNAc ligand attached to the 5' end.

In some embodiments, the composition comprises an oligonucleotide that inhibits the expression of ANGPTL4 wherein the oligonucleotide comprises an siRNA comprising a sense strand and an antisense strand, wherein the sense strand comprises modification pattern 1S and the antisense strand comprises modification pattern 1AS, 2AS, 3AS, 4AS, 5AS, 6AS, 7AS, 8AS, or 9AS. In some embodiments, the sense strand comprises modification pattern 2S and the antisense strand comprises modification pattern 1AS, 2AS, 3AS, 4AS, 5AS, 6AS, 7AS, 8AS, or 9AS. In some embodiments, the sense strand comprises modification pattern 3S and the antisense strand comprises modification pattern 1AS, 2AS, 3AS, 4AS, 5AS, 6AS, 7AS, 8AS, or 9AS. In some embodiments, the sense strand comprises modification pattern 4S and the antisense strand comprises modification pattern 1AS, 2AS, 3AS, 4AS, 5AS, 6AS, 7AS, 8AS, or 9AS. In some embodiments, the sense strand comprises modification pattern 5S and the antisense strand comprises modification pattern 1AS, 2AS, 3AS, 4AS, 5AS, 6AS, 7AS, 8AS, or 9AS. In some embodiments, the sense strand comprises modification pattern 6S and the antisense strand comprises modification pattern 1AS, 2AS, 3AS, 4AS, 5AS, 6AS, 7AS, 8AS, or 9AS. In some embodiments, the sense strand comprises modification pattern 1AS, 2AS, 3AS, 4AS, 5AS, 6AS, 7AS, 8AS, or 9AS. In some embodiments, the antisense strand comprises modification pattern 1AS, 2AS, 3AS, 4AS, 5AS, 6AS, 7AS, 8AS, or 9AS. In some embodiments, the sense strand or the antisense strand comprises modification pattern ASO1.

Any combination of sense and antisense modification patterns may be used. In some embodiments, the sense strand comprises modification pattern 1S, and the antisense strand comprises modification pattern 1AS. In some embodiments, the sense strand comprises modification pattern 2S, and the antisense strand comprises modification pattern 2AS. In some embodiments, the sense strand comprises modification pattern 2S, and the antisense strand comprises modification pattern 3AS. In some embodiments, the sense strand comprises modification pattern 3S, and the antisense strand comprises modification pattern 1AS. In some embodiments, the sense strand comprises modification pattern 3S, and the antisense strand comprises modification pattern 4AS. In some embodiments, the sense strand comprises modification pattern 3S, and the antisense strand comprises modification pattern 5AS. In some embodiments, the sense strand comprises modification pattern 3S, and the antisense strand comprises modification pattern 6AS. In some embodiments, the sense strand comprises modification pattern 3S, and the antisense strand comprises modification pattern 7AS. In some embodiments, the sense strand comprises modification pattern 3S, and the antisense strand comprises modification pattern 8AS. In some embodiments, the sense strand comprises modification pattern 6S, and the antisense strand comprises modification pattern 1AS. In some embodiments, the sense strand comprises modification pattern 6S, and the antisense strand comprises modification pattern 4AS. In some embodiments, the sense strand comprises modification pattern 6S, and the antisense strand comprises modification pattern 5AS. In some embodiments, the sense strand comprises modification pattern 6S, and the antisense strand comprises modification pattern 6AS. In some embodiments, the sense strand comprises modification pattern 6S, and the antisense strand comprises modification pattern 7AS. In some embodiments, the sense strand comprises modification pattern 6S, and the antisense strand comprises modification pattern 8AS.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 1S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 1S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 1S.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 2S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 2S.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 3S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 3S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 3S.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 4S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 4S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 4S.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 5S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 5S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 5S.

In some embodiments, the composition comprises an oligonucleotide that inhibits the expression of ANGPTL4 wherein the oligonucleotide comprises an siRNA comprising a sense strand and an antisense strand, wherein the sense strand comprises a nucleoside sequence comprising or consisting of the sequence of any one of SEQ ID NOs: 1-1854 or 13970-13977, and modification pattern 6S. In some embodiments, the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 6S. In some embodiments, the sense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 6S.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 1AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 1AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 1AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 2AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 2AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 3AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 3AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 3AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 4AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 4AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 4AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 5AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 5AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 5AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 6AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 6AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 6AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 7AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 7AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 7AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 8AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 8AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 8AS.

In some embodiments, the composition comprises an oligonucleotide that inhibits the expression of ANGPTL4 wherein the oligonucleotide comprises an siRNA comprising a sense strand and an antisense strand, wherein the antisense strand comprises a nucleoside sequence comprising or consisting of the sequence of any one of SEQ ID NOs: 1-1854 or 13970-13977, and modification pattern 9AS. In some embodiments, the antisense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 9AS. In some embodiments, the antisense strand comprises a nucleoside sequence comprising or consisting of the sequence of any one of SEQ ID NOs: 1-1854 or 13970-13977, or a nucleic acid sequence thereof having 3 or 4 nucleoside substitutions, additions, or deletions, and modification pattern 9AS.

In some embodiments, the sense strand comprises a nucleoside sequence comprising or consisting the sequence of any one of SEQ ID NOs: 1-1854 or 13970-13977, an overhang (such as a 2 base 3' overhang), and modification pattern 1S. In some embodiments, the sense strand comprises a nucleoside sequence comprising or consisting the sequence of any one of SEQ ID NOs: 1-1854 or 13970-13977, an overhang (such as a 2 base 3' overhang), and modification pattern 2S. In some embodiments, the sense strand comprises a nucleoside sequence comprising or consisting the sequence of any one of SEQ ID NOs: 1-1854 or 13970-13977, an overhang (such as a 2 base 3' overhang), and modification pattern 3S. In some embodiments, the sense strand comprises a nucleoside sequence comprising or consisting the sequence of any one of SEQ ID NOs: 1-1854 or 13970-13977, an overhang (such as a 2 base 3' overhang), and modification pattern 4S. In some embodiments, the sense strand comprises a nucleoside sequence comprising or consisting the sequence of any one of SEQ ID NOs: 1-1854 or 13970-13977, an overhang (such as a 2 base 3' overhang), and modification pattern 5S. In some embodiments, the sense strand comprises a nucleoside sequence comprising or consisting the sequence of any one of SEQ ID NOs: 1-1854 or 13970-13977, an overhang (such as a 2 base 3' overhang), and modification pattern 6S. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 1AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 2AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 3AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 4AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 5AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 6AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 7AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 8AS. In some embodiments, the antisense strand comprises a nucleoside sequence comprising or consisting of the sequence of any one of SEQ ID NOs: 1855-3708 or 13978-13985, and an overhang (such as a 2 base 3' overhang), and modification pattern 9AS. In some embodiments, the overhang comprises one or more uracil nucleosides. In some embodiments, the one or more uracil nucleosides of the overhang are connected at the 3' end to another nucleoside via a phosphorothioate linkage. In some embodiments, the overhang comprises one uracil nucleoside. In some embodiments, the overhang comprises two uracil nucleoside.

Some embodiments include a composition comprising an oligonucleotide that targets Angiopoietin like 4 (ANGPTL4) and when administered to a cell decreases expression of ANGPTL4, wherein the oligonucleotide comprises a small interfering RNA (siRNA) comprising a sense strand and an antisense strand, wherein the sense strand comprises an oligonucleotide sequence of SEQ ID NOs: 759, 1285, 1580, or 1840 in which at least one internucleoside linkage is modified and at least one base is modified, or an oligonucleotide sequence comprising 1 or 2 nucleoside, substitutions, additions, or deletions of SEQ ID NOs: 759, 1285, 1580, or 1840 in which at least one internucleoside linkage is modified and at least one base is modified, and wherein the antisense strand comprises an oligonucleotide sequence of SEQ ID NOs: 2613, 3139, 3434, or 3694 in which at least one internucleoside linkage is modified and at least one base is modified, or an oligonucleotide sequence comprising 1 or 2 nucleoside, substitutions, additions, or deletions of SEQ ID NOs: 2613, 3139, 3434, or 3694 in which at least one internucleoside linkage is modified and at least one base is modified.

Some embodiments include a composition comprising an oligonucleotide that targets Angiopoietin like 4 (ANGPTL4) and when administered to a cell decreases expression of ANGPTL4, wherein the oligonucleotide comprises a small interfering RNA (siRNA) comprising a sense strand and an antisense strand, wherein the sense strand comprises an oligonucleotide sequence of any one of SEQ ID NOs: 13970-13973 in which at least one internucleoside linkage is modified and at least one base is modified, or an oligonucleotide sequence comprising 1 or 2 nucleoside, substitutions, additions, or deletions of any one of SEQ ID NOs: 13970-13973 in which at least one internucleoside linkage is modified and at least one base is modified, and wherein the antisense strand comprises an oligonucleotide sequence of any one of SEQ ID NOs: 13978-13981 in which at least one internucleoside linkage is modified and at least one base is modified, or an oligonucleotide sequence comprising 1 or 2 nucleoside, substitutions, additions, or deletions of any one of SEQ ID NOs: 13978-13981 in which at least one internucleoside linkage is modified and at least one base is modified.

Some embodiments include a composition comprising an oligonucleotide that targets Angiopoietin like 4 (ANGPTL4) and when administered to a cell decreases expression of ANGPTL4, wherein the oligonucleotide comprises a small interfering RNA (siRNA) comprising a sense strand and an antisense strand, wherein the sense strand comprises an oligonucleotide sequence of any one of SEQ ID NOs: 13974-13977 in which at least one internucleoside linkage is modified and at least one base is modified, or an oligonucleotide sequence comprising 1 or 2 nucleoside, substitutions, additions, or deletions of any one of SEQ ID NOs: 13974-13977 in which at least one internucleoside linkage is modified and at least one base is modified, and wherein the antisense strand comprises an oligonucleotide sequence of any one of SEQ ID NOs: 13982-13985 in which at least one internucleoside linkage is modified and at least one base is modified, or an oligonucleotide sequence comprising 1 or 2 nucleoside, substitutions, additions, or deletions of any one of SEQ ID NOs: 13982-13985 in which at least one internucleoside linkage is modified and at least one base is modified.

Some embodiments include a composition comprising an oligonucleotide that targets Angiopoietin like 4 (ANGPTL4) and when administered to a cell decreases expression of ANGPTL4, wherein the oligonucleotide comprises a small interfering RNA (siRNA) comprising a sense strand and an antisense strand, wherein the sense strand comprises an oligonucleotide sequence of any one of SEQ ID NOs: 13990-14005 in which at least one internucleoside linkage is modified and at least one base is modified, or an oligonucleotide sequence comprising 1 or 2 nucleoside, substitutions, additions, or deletions of any one of SEQ ID NOs: 13990-14005 in which at least one internucleoside linkage is modified and at least one base is modified, and wherein the antisense strand comprises an oligonucleotide sequence of any one of SEQ ID NOs: 14134-14157 in which at least one internucleoside linkage is modified and at least one base is modified, or an oligonucleotide sequence comprising 1 or 2 nucleoside, substitutions, additions, or deletions of any one of SEQ ID NOs: 14134-14157 in which at least one internucleoside linkage is modified and at least one base is modified.

Some embodiments include a composition comprising an oligonucleotide that targets Angiopoietin like 4 (ANGPTL4) and when administered to a cell decreases expression of ANGPTL4, wherein the oligonucleotide comprises a small interfering RNA (siRNA) comprising a sense strand and an antisense strand, wherein the sense strand comprises an oligonucleotide sequence of any one of SEQ ID NOs: 1-1854 in which at least one internucleoside linkage is modified and at least one base is modified, or an oligonucleotide sequence comprising 1 or 2 nucleoside, substitutions, additions, or deletions of any one of SEQ ID NOs: 1-1854 in which at least one internucleoside linkage is modified and at least one base is modified, and wherein the antisense strand comprises an oligonucleotide sequence of any one of SEQ ID NOs: 1855-3708 in which at least one internucleoside linkage is modified and at least one base is modified, or an oligonucleotide sequence comprising 1 or 2 nucleoside, substitutions, additions, or deletions of any one of SEQ ID NOs: 1855-3708 in which at least one internucleoside linkage is modified and at least one base is modified.

2. ASO Modification Patterns

In some embodiments, the composition comprises an oligonucleotide that inhibits the expression of ANGPTL4, wherein the oligonucleotide comprises an antisense oligonucleotide (ASO). In some embodiments, the ASO comprises modification pattern ASO1: 5'-nsnsnsnsnsdNsdNsdNsdNsdNsdNsdNsdNsdNsnsnsnsnsn-3', wherein "dN" is any deoxynucleotide, "n" is a 2'O-methyl or 2'O-methoxyethyl-modified nucleoside, and "s" is a phosphorothioate linkage. In some embodiments, the ASO comprises modification pattern 1S, 2S, 3S, 4S, 5S, 6S, 1AS, 2AS, 3AS, 4AS, 5AS, 6AS, 7AS, 8AS, or 9AS. In some embodiments, the ASO comprises DNA.

In some embodiments, the composition comprises an oligonucleotide that inhibits the expression of ANGPTL4, wherein the oligonucleotide comprises an antisense oligonucleotide (ASO). In some embodiments, the ASO comprises a nucleoside sequence comprising or consisting of the sequence of any one of SEQ ID NOs: 3709-13934, and modification pattern ASO1. In some embodiments, the ASO comprises a nucleoside sequence comprising or consisting of the sequence of any one of SEQ ID NOs: 3709-13934, or a nucleic acid sequence thereof having 1 or 2 nucleoside substitutions, additions, or deletions, and modification pattern ASO1. In some embodiments, the ASO comprises a nucleoside sequence comprising or consisting of the sequence of any one of SEQ ID NOs: 3709-13934, or a nucleic acid sequence thereof having 3 or 4 nucleoside substitutions, additions, or deletions, and modification pattern ASO1.

ASO1 modification pattern ASO1 may include a GalNAc ligand attached to the 3' end. ASO1 modification pattern ASO1 may include a GalNAc ligand attached to the 5' end.

D. Formulations

In some embodiments, the composition is a pharmaceutical composition. In some embodiments, the composition is sterile. In some embodiments, the composition further comprises a pharmaceutically acceptable carrier.

In some embodiments, the pharmaceutically acceptable carrier comprises water. In some embodiments, the pharmaceutically acceptable carrier comprises a buffer. In some embodiments, the pharmaceutically acceptable carrier comprises a saline solution. In some embodiments, the pharmaceutically acceptable carrier comprises water, a buffer, or a saline solution. In some embodiments, the composition comprises a liposome. In some embodiments, the pharmaceutically acceptable carrier comprises liposomes, lipids, nanoparticles, proteins, protein-antibody complexes, peptides, cellulose, nanogel, or a combination thereof.

II. Methods and Uses

Disclosed herein, in some embodiments, are methods of administering a composition described herein to a subject. Some embodiments relate to use a composition described herein, such as administering the composition to a subject.

Some embodiments relate to a method of treating a disorder in a subject in need thereof. Some embodiments relate to use of a composition described herein in the method of treatment. Some embodiments include administering a composition described herein to a subject with the disorder. In some embodiments, the administration treats the disorder in the subject. In some embodiments, the composition treats the disorder in the subject.

In some embodiments, the treatment comprises prevention, inhibition, or reversion of the disorder in the subject. Some embodiments relate to use of a composition described herein in the method of preventing, inhibiting, or reversing the disorder. Some embodiments relate to a method of preventing, inhibiting, or reversing a disorder a disorder in a subject in need thereof. Some embodiments include administering a composition described herein to a subject with the disorder. In some embodiments, the administration prevents, inhibits, or reverses the disorder in the subject. In some embodiments, the composition prevents, inhibits, or reverses the disorder in the subject.

Some embodiments relate to a method of preventing a disorder a disorder in a subject in need thereof. Some embodiments relate to use of a composition described herein in the method of preventing the disorder. Some embodiments include administering a composition described herein to a subject with the disorder. In some embodiments, the administration prevents the disorder in the subject. In some embodiments, the composition prevents the disorder in the subject.

Some embodiments relate to a method of inhibiting a disorder a disorder in a subject in need thereof. Some embodiments relate to use of a composition described herein in the method of inhibiting the disorder. Some embodiments include administering a composition described herein to a subject with the disorder. In some embodiments, the administration inhibits the disorder in the subject. In some embodiments, the composition inhibits the disorder in the subject.

Some embodiments relate to a method of reversing a disorder a disorder in a subject in need thereof. Some embodiments relate to use of a composition described herein in the method of reversing the disorder. Some embodiments include administering a composition described herein to a subject with the disorder. In some embodiments, the administration reverses the disorder in the subject. In some embodiments, the composition reverses the disorder in the subject.

A. Disorders

Some embodiments of the methods described herein include treating a disorder in a subject in need thereof. In some embodiments, the disorder is a metabolic disorder. Examples of metabolic disorders include hyperlipidemia (for example, hypertriglyceridemia) and diabetes (for example, type II diabetes). In some embodiments, the metabolic disorder comprises hyperlipidemia. In some embodiments, the metabolic disorder comprises hypertriglyceridemia. In some embodiments, the metabolic disorder comprises familial chylomicronemia. In some embodiments, the metabolic disorder comprises hypertriglyceridemia in the context of familial chylomicronemia. In some embodiments, the metabolic disorder comprises pancreatitis. In some embodiments, the metabolic disorder comprises acute pancreatitis. In some embodiments, the metabolic disorder comprises hypertriglyceridemia and associated acute pancreatitis. In some embodiments, the metabolic disorder comprises diabetes. In some embodiments, the metabolic disorder comprises type 2 diabetes. Some embodiments include a method of treating a metabolic disorder in a subject in need thereof, the method comprising administering to the subject a composition comprising an oligonucleotide that targets ANGPTL4.

In some embodiments, the disorder is a cardiometabolic disorder such as a cardiovascular disorder or a metabolic disorder. In some embodiments, the disorder is a cardiovascular disorder. Examples of cardiovascular disorders include heart disease, myocardial infarction, angina (for example, angina pectoris), and atherosclerosis. In some embodiments, the cardiovascular disorder comprises heart disease. In some embodiments, the cardiovascular disorder comprises myocardial infarction. In some embodiments, the cardiovascular disorder comprises angina pectoris. In some embodiments, the cardiovascular disorder comprises atherosclerosis. Some embodiments include a method of treating a cardiovascular disorder in a subject in need thereof, the method comprising administering to the subject a composition comprising an oligonucleotide that targets ANGPTL4.

B. Subjects

Some embodiments of the methods described herein include treatment of a subject. Examples of subjects include vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is a dog. In some embodiments, the subject is a cat. In some embodiments, the subject is a cattle. In some embodiments, the subject is a mouse. In some embodiments, the subject is a rat. In some embodiments, the subject is a primate. In some embodiments, the subject is a monkey. In some embodiments, the subject is an animal, a mammal, a dog, a cat, cattle, a rodent, a mouse, a rat, a primate, or a monkey. In some embodiments, the subject is a human.

In some embodiments, the subject has a body mass index (BMI) of 25, 26, 27, 28, 29, 30, 31, 32, 33, 34, 35, 36, 37, 38, 39, 40, 41, 42, 43, 44, 45, 46, 47, 48, 49, 50, or more, or a range defined by any two of the aforementioned integers. In some embodiments, the subject is overweight. In some embodiments, the subject has a BMI of 25 or more. In some embodiments, the subject has a BMI of 25-29. In some embodiments, the subject is obese. In some embodiments, the subject has a BMI of 30 or more. In some embodiments, the subject has a BMI of 30-39. In some embodiments, the subject has a BMI of 40-50. In some embodiments, the subject has a BMI of 25-50.

In some embodiments, the subject is ≥90 years of age. In some embodiments, the subject is ≥85 years of age. In some embodiments, the subject is ≥80 years of age. In some embodiments, the subject is ≥70 years of age. In some embodiments, the subject is ≥60 years of age. In some embodiments, the subject is ≥50 years of age. In some embodiments, the subject is ≥40 years of age. In some embodiments, the subject is ≥30 years of age. In some embodiments, the subject is ≥20 years of age. In some embodiments, the subject is ≥10 years of age. In some embodiments, the subject is ≥1 years of age. In some embodiments, the subject is ≥0 years of age.

In some embodiments, the subject is ≤100 years of age. In some embodiments, the subject is ≤90 years of age. In some embodiments, the subject is ≤85 years of age. In some embodiments, the subject is ≤80 years of age. In some embodiments, the subject is ≤70 years of age. In some embodiments, the subject is ≤60 years of age. In some embodiments, the subject is ≤50 years of age. In some embodiments, the subject is ≤40 years of age. In some embodiments, the subject is ≤30 years of age. In some embodiments, the subject is ≤20 years of age. In some embodiments, the subject is ≤10 years of age. In some embodiments, the subject is ≤1 years of age.

In some embodiments, the subject is between 0 and 100 years of age. In some embodiments, the subject is between 20 and 90 years of age. In some embodiments, the subject is between 30 and 80 years of age. In some embodiments, the subject is between 40 and 75 years of age. In some embodiments, the subject is between 50 and 70 years of age. In some embodiments, the subject is between 40 and 85 years of age.

C. Baseline Measurements

Some embodiments of the methods described herein include obtaining a baseline measurement from a subject. For example, in some embodiments, a baseline measurement is obtained from the subject prior to treating the subject.

In some embodiments, the baseline measurement is obtained by performing an assay such as an immunoassay, a colorimetric assay, or a fluorescence assay, on the sample obtained from the subject. In some embodiments, the baseline measurement is obtained by an immunoassay, a colorimetric assay, or a fluorescence assay. In some embodiments, the baseline measurement is obtained by PCR.

In some embodiments, the baseline measurement is a baseline triglyceride measurement. In some embodiments, the baseline triglyceride measurement is a baseline triglyceride concentration (for example, mg/dL). In some embodiments, the baseline triglyceride measurement is a baseline circulating triglyceride measurement. In some embodiments, the baseline triglyceride measurement is obtained by an assay such as an immunoassay, a colorimetric assay, or a fluorescence assay.

In some embodiments, the baseline measurement is a baseline cholesterol measurement. In some embodiments, the baseline cholesterol measurement is a baseline cholesterol concentration. In some embodiments, the baseline cholesterol concentration is a baseline total cholesterol concentration. In some embodiments, the baseline cholesterol measurement is a baseline circulating cholesterol measurement. In some embodiments, the baseline cholesterol measurement is a baseline low density lipoprotein (LDL) measurement. In some embodiments, the baseline cholesterol measurement is a baseline very low density lipoprotein (VLDL) measurement. In some embodiments, the baseline cholesterol measurement is obtained by an assay such as an immunoassay, a colorimetric assay, or a fluorescence assay.

In some embodiments, the baseline measurement is a baseline HDL measurement. In some embodiments, the baseline HDL measurement is a baseline HDL concentration. In some embodiments, the baseline HDL measurement is indicated relative to a baseline total cholesterol measurement. In some embodiments, the baseline HDL measurement is a baseline circulating HDL measurement. In some embodiments, the baseline HDL measurement is obtained by an assay such as an immunoassay, a colorimetric assay, or a fluorescence assay.

In some embodiments, the baseline measurement is a baseline glucose measurement. In some embodiments, the baseline glucose measurement is a baseline glucose concentration (for example, mg/dL). In some embodiments, the baseline glucose measurement comprises a baseline glucose concentration. In some embodiments, the baseline glucose measurement is a baseline circulating glucose measurement. In some embodiments, the baseline glucose measurement is obtained by an assay such as an immunoassay, a colorimetric assay, or a fluorescence assay. In some embodiments, the baseline glucose measurement is obtained In some embodiments, the baseline glucose measurement comprises a baseline glucose tolerance test. In some embodiments, the baseline glucose tolerance test comprises administering glucose to the subject, and then obtaining multiple baseline glucose measurements over time after administering the glucose to the subject. In some embodiments, the glucose is administered orally. In some embodiments, the glucose is administered by injection. In some embodiments, the multiple baseline glucose measurements are integrated into a baseline glucose area under the curve (AUC) measurement. In some embodiments, the baseline glucose tolerance test is performed on the subject in a fasted state such as after an overnight fast. In some embodiments, the baseline glucose measurement comprises a baseline glucose measurement other than a baseline glucose tolerance test.

In some embodiments, the baseline measurement is a baseline insulin measurement. In some embodiments, the baseline insulin measurement is a baseline insulin sensitivity measurement. In some embodiments, the baseline insulin sensitivity measurement is obtained using a glucose clamp technique such as a hyperinsulinemic euglycemic clamp. In some embodiments, the baseline insulin measurement is a baseline insulin concentration. In some embodiments, the baseline insulin measurement comprises a baseline insulin concentration. In some embodiments, the baseline insulin measurement is a baseline circulating insulin measurement. In some embodiments, the baseline insulin measurement is obtained by an assay such as an immunoassay (for example, an ELISA or an immunoblot), a colorimetric assay, or a fluorescence assay. In some embodiments, the baseline insulin sensitivity measurement comprises a baseline glucose tolerance test. In some embodiments, the baseline insulin sensitivity measurement comprises a baseline insulin sensitivity measurement other than a baseline glucose tolerance test.

In some embodiments, the baseline insulin measurement comprises a baseline insulin response test. In some embodiments, the baseline insulin response test comprises administering glucose to the subject and then obtaining multiple baseline insulin measurements over time after administering the glucose to the subject. In some embodiments, the glucose is administered orally. In some embodiments, the glucose is administered by injection. In some embodiments, the multiple baseline insulin measurements are integrated into a baseline insulin AUC measurement. In some embodiments, the baseline insulin response test is performed on the subject in a fasted state such as after an overnight fast.

In some embodiments, the baseline insulin measurement comprises a baseline glucose response test. In some embodiments, the baseline glucose response test comprises administering insulin to the subject, and then obtaining multiple baseline glucose measurements over time after administering the insulin to the subject. In some embodiments, the insulin is administered by injection. In some embodiments, the multiple baseline glucose measurements are integrated into a baseline glucose AUC measurement. In some embodiments, the multiple baseline glucose measurements are obtained with a glucometer. In some embodiments, the glucose response test is performed on the subject in a fasted state such as after an overnight fast. In some embodiments, the glucose response test is performed on the subject after administering food, drink, or glucose to the subject.

In some embodiments, the baseline measurement is a baseline ANGPTL4 protein measurement. In some embodiments, the baseline ANGPTL4 protein measurement comprises a baseline ANGPTL4 protein level. In some embodiments, the baseline ANGPTL4 protein level is indicated as a mass or percentage of ANGPTL4 protein per sample weight. In some embodiments, the baseline ANGPTL4 protein level is indicated as a mass or percentage of ANGPTL4 protein per sample volume. In some embodiments, the baseline ANGPTL4 protein level is indicated as a mass or percentage of ANGPTL4 protein per total protein within the sample. In some embodiments, the baseline ANGPTL4 protein measurement is a baseline cell (e.g. hepatocyte) ANGPTL4 protein measurement. In some embodiments, the baseline ANGPTL4 protein measurement is a baseline tissue (e.g. liver tissue) ANGPTL4 protein measurement. In some embodiments, the baseline ANGPTL4 protein measurement is a baseline circulating ANGPTL4 protein measurement. In some embodiments, the baseline ANGPTL4 protein measurement is obtained by an assay such as an immunoassay, a colorimetric assay, or a fluorescence assay.

In some embodiments, the baseline measurement is a baseline ANGPTL4 mRNA measurement. In some embodiments, the baseline ANGPTL4 mRNA measurement comprises a baseline ANGPTL4 mRNA level. In some embodiments, the baseline ANGPTL4 mRNA level is indicated as a mass or percentage of ANGPTL4 mRNA per sample weight. In some embodiments, the baseline ANGPTL4 mRNA level is indicated as a mass or percentage of ANGPTL4 mRNA per sample volume. In some embodiments, the baseline ANGPTL4 mRNA level is indicated as a mass or percentage of ANGPTL4 mRNA per total mRNA within the sample. In some embodiments, the baseline ANGPTL4 mRNA level is indicated as a mass or percentage of ANGPTL4 mRNA per total nucleic acids within the sample. In some embodiments, the baseline ANGPTL4 mRNA level is indicated relative to another mRNA level, such as an mRNA level of a housekeeping gene, within the sample. In some embodiments, the baseline ANGPTL4 mRNA measurement is obtained by an assay such as a polymerase chain reaction (PCR) assay. In some embodiments, the PCR comprises quantitative PCR (qPCR). In some embodiments, the PCR comprises reverse transcription of the ANGPTL4 mRNA.

Some embodiments of the methods described herein include obtaining a sample from a subject. In some embodiments, the baseline measurement is obtained in a sample obtained from the subject. In some embodiments, the sample is obtained from the subject prior to administration or treatment of the subject with a composition described herein. In some embodiments, a baseline measurement is obtained in a sample obtained from the subject prior to administering the composition to the subject. In some embodiments, the sample is obtained from the subject in a fasted state. In some embodiments, the sample is obtained from the subject after an overnight fasting period. In some embodiments, the sample is obtained from the subject in a fed state.

In some embodiments, the sample comprises a fluid. In some embodiments, the sample is a fluid sample. In some embodiments, the sample is a blood, plasma, or serum sample. In some embodiments, the sample comprises blood. In some embodiments, the sample is a blood sample. In some embodiments, the sample is a whole-blood sample. In some embodiments, the blood is fractionated or centrifuged. In some embodiments, the sample comprises plasma. In some embodiments, the sample is a plasma sample. In some embodiments, the sample comprises serum. In some embodiments, the sample is a serum sample. For example, the baseline triglyceride 33measurement, the baseline cholesterol measurement, the baseline HDL measurement, the baseline glucose measurement, the baseline insulin measurement, or the baseline ANGPTL4 protein measurement may be obtained in a serum sample from the patient.

In some embodiments, the sample comprises a tissue. In some embodiments, the sample is a tissue sample. In some embodiments, the sample comprises liver tissue. In some embodiments, the sample is a liver sample. In some embodiments, the sample comprises adipose tissue. In some embodiments, the sample is an adipose sample. In some embodiments, the sample comprises pancreatic tissue. In some embodiments, the sample comprises a pancreas sample. For example, the baseline ANGPTL4 mRNA measurement, or the baseline ANGPTL4 protein measurement, may be obtained in a liver or adipose sample from the patient. In some embodiments, the sample comprises intestinal tissue such as small intestinal tissue. In some embodiments, the sample is a small intestine sample. In some embodiments, the sample comprises lymph node tissue such as mesenteric lymph node tissue. In some embodiments, the sample is a mesenteric lymph node sample. In some embodiments, the sample comprises cardiac tissue such as ventricular or atrial tissue. In some embodiments, the sample is a cardiac sample. In some embodiments, the tissue sample comprises liver, adipose, small intestine, mesenteric lymph node, or cardiac tissue. In some embodiments, the tissue sample comprises brown adipose tissue, white adipose tissue, kidney tissue, or muscle tissue.

D. Effects

In some embodiments, the composition or administration of the composition affects a measurement such as a triglyceride measurement, a cholesterol measurement, an HDL measurement, a glucose measurement, an insulin measurement, an ANGPTL4 protein measurement (for example, circulating or tissue ANGPTL4 protein levels), or an ANGPTL4 mRNA measurement, relative to the baseline measurement.

Some embodiments of the methods described herein include obtaining the measurement from a subject. For example, the measurement may be obtained from the subject after treating the subject. In some embodiments, the measurement is obtained in a second sample (such as a fluid or tissue sample described herein) obtained from the subject after the composition is administered to the subject. In some embodiments, the measurement is an indication that the disorder has been treated.

In some embodiments, the measurement is obtained by an assay as described herein. For example, the assay may comprise an immunoassay, a colorimetric assay, a fluorescence assay, or a PCR assay.

In some embodiments, the measurement is obtained within 1 week, within 2 weeks, within 3 weeks, within 1 month, within 2 months, within 3 months, within 6 months, within 1 year, within 2 years, within 3 years, within 4 years, or within 5 years after the administration of the composition. In some embodiments, the measurement is obtained after 1 week, after 2 weeks, after 3 weeks, after 1 month, after 2 months, after 3 months, after 6 months, after 1 year, after 2 years, after 3 years, after 4 years, or after 5 years, following the administration of the composition.

In some embodiments, the measurement is a triglyceride measurement. In some embodiments, the triglyceride measurement is a triglyceride concentration (for example, mg/dL). In some embodiments, the triglyceride measurement is a circulating triglyceride measurement. In some embodiments, the triglyceride measurement is obtained by an assay such as an immunoassay, a colorimetric assay, or a fluorescence assay.

In some embodiments, the composition reduces the triglyceride measurement relative to the baseline triglyceride measurement. In some embodiments, the composition reduces circulating triglycerides relative to the baseline triglyceride measurement. In some embodiments, the reduced triglycerides are measured in a second sample obtained from the subject after administering the composition to the subject.

In some embodiments, the triglyceride measurement is decreased by about 2.5% or more, about 5% or more, or about 7.5% or more, relative to the baseline triglyceride measurement. In some embodiments, the triglyceride measurement is decreased by about 10% or more, relative to the baseline triglyceride measurement. In some embodiments, the triglyceride measurement is decreased by about 20% or more, about 30% or more, about 40% or more, about 50% or more, about 60% or more, about 70% or more, about 80% or more, about 90% or more, or about 100%, relative to the baseline triglyceride measurement. In some embodiments, the triglyceride measurement is decreased by no more than about 2.5%, no more than about 5%, or no more than about 7.5%, relative to the baseline triglyceride measurement. In some embodiments, the triglyceride measurement is decreased by no more than about 10%, relative to the baseline triglyceride measurement. In some embodiments, the triglyceride measurement is decreased by no more than about 20%, no more than about 30%, no more than about 40%, no more than about 50%, no more than about 60%, no more than about 70%, no more than about 80%, no more than about 90%, or no more than about 100% relative to the baseline triglyceride measurement. In some embodiments, the triglyceride measurement is decreased by 2.5%, 5%, 7.5%, 10%, 20%, 30%, 40%, 50%, 60%, 70%, 80%, 90%, 100%, or by a range defined by any of the two aforementioned percentages.

In some embodiments, the measurement is a cholesterol measurement. In some embodiments, the cholesterol measurement is a total cholesterol measurement. In some embodiments, the cholesterol measurement is a cholesterol concentration. In some embodiments, the cholesterol concentration is a total cholesterol concentration. In some embodiments, the cholesterol measurement is a circulating cholesterol measurement. In some embodiments, the cholesterol measurement is a low density lipoprotein (LDL) measurement. In some embodiments, the cholesterol measurement is a very low density lipoprotein (VLDL) measurement. In some embodiments, the cholesterol measurement is obtained by an assay such as an immunoassay, a colorimetric assay, or a fluorescence assay.

In some embodiments, the composition reduces the cholesterol measurement relative to the baseline cholesterol measurement. In some embodiments, the composition reduces circulating cholesterol relative to the baseline cholesterol measurement. In some embodiments, the reduced cholesterol is measured in a second sample obtained from the subject after administering the composition to the subject.

In some embodiments, the cholesterol measurement is decreased by about 2.5% or more, about 5% or more, or about 7.5% or more, relative to the baseline cholesterol measurement. In some embodiments, the cholesterol measurement is decreased by about 10% or more, relative to the baseline cholesterol measurement. In some embodiments, the cholesterol measurement is decreased by about 20% or more, about 30% or more, about 40% or more, about 50% or more, about 60% or more, about 70% or more, about 80% or more, about 90% or more, or about 100%, relative to the baseline cholesterol measurement. In some embodiments, the cholesterol is decreased by no more than about 2.5%, no more than about 5%, or no more than about 7.5%, relative to the baseline cholesterol measurement. In some embodiments, the cholesterol is decreased by no more than about 10%, relative to the baseline cholesterol measurement. In some embodiments, the cholesterol is decreased by no more than about 20%, no more than about 30%, no more than about 40%, no more than about 50%, no more than about 60%, no more than about 70%, no more than about 80%, no more than about 90%, or no more than about 100% relative to the baseline cholesterol measurement. In some embodiments, the cholesterol measurement is decreased by 2.5%, 5%, 7.5%, 10%, 20%, 30%, 40%, 50%, 60%, 70%, 80%, 90%, 100%, or by a range defined by any of the two aforementioned percentages.

In some embodiments, the measurement is an HDL measurement. In some embodiments, the HDL measurement is an HDL concentration. In some embodiments, the HDL measurement is indicated relative to a total cholesterol measurement. In some embodiments, the HDL measurement is a circulating HDL measurement. In some embodiments, the HDL measurement is obtained by an assay such as an immunoassay, a colorimetric assay, or a fluorescence assay.

In some embodiments, the composition reduces the HDL measurement relative to the baseline HDL measurement. In some embodiments, the composition increases circulating HDL relative to the baseline HDL measurement. In some embodiments, the increased HDL is measured in a second sample obtained from the subject after administering the composition to the subject.

In some embodiments, the HDL measurement is increased by about 2.5% or more, about 5% or more, or about 7.5% or more, relative to the baseline HDL measurement. In some embodiments, the HDL measurement is increased by about 10% or more, relative to the baseline HDL measurement. In some embodiments, the HDL measurement is increased by about 20% or more, about 30% or more, about 40% or more, about 50% or more, about 60% or more, about 70% or more, about 80% or more, about 90% or more, or about 100% or more relative to the baseline HDL measurement. In some embodiments, the HDL measurement is increased by about 200% or more, about 300% or more, about 400% or more, about 500% or more, about 600% or more, about 700% or more, about 800% or more, about 900% or more, or about 1000% or more, relative to the baseline HDL measurement. In some embodiments, the HDL measurement is increased by no more than about 2.5%, no more than about 5%, or no more than about 7.5%, relative to the baseline HDL measurement. In some embodiments, the HDL measurement is increased by no more than about 10%, relative to the baseline HDL measurement. In some embodiments, the HDL measurement is increased by no more than about 20%, no more than about 30%, no more than about 40%, no more than about 50%, no more than about 60%, no more than about 70%, no more than about 80%, no more than about 90%, or no more than about 100% relative to the baseline HDL measurement. In some embodiments, the HDL measurement is increased by no more than about 200%, no more than about 300%, no more than about 400%, no more than about 500%, no more than about 600%, no more than about 700%, no more than about 800%, no more than about 900%, or no more than about 1000%, relative to the baseline HDL measurement. In some embodiments, the HDL measurement is increased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the measurement is a glucose measurement. In some embodiments, the glucose measurement comprises a glucose concentration (for example, mg/dL). In some embodiments, the glucose measurement is a glucose concentration. In some embodiments, the glucose measurement is a circulating glucose measurement. In some embodiments, the glucose measurement is obtained by an assay such as an immunoassay, a colorimetric assay, or a fluorescence assay. In some embodiments, the glucose measurement is obtained using a glucometer.

In some embodiments, the glucose measurement comprises a glucose tolerance test. In some embodiments, the glucose tolerance test comprises administering glucose to the subject, and then obtaining multiple glucose measurements over time after administering the glucose to the subject. In some embodiments, the glucose is administered orally. In some embodiments, the glucose is administered by injection. In some embodiments, the multiple glucose measurements are integrated into a glucose area under the curve (AUC) measurement. In some embodiments, the glucose tolerance test is performed on the subject in a fasted state such as after an overnight fast. In some embodiments, the glucose measurement comprises a glucose measurement other than a glucose tolerance test.

In some embodiments, the composition reduces the glucose measurement relative to the baseline glucose measurement. In some embodiments, the composition reduces circulating glucose relative to the baseline glucose measurement. In some embodiments, the reduced glucose is measured in a second sample obtained from the subject after administering the composition to the subject. In some embodiments, the composition reduces one or more of the multiple glucose measurements of the glucose tolerance test relative to one or more of the multiple glucose measurements of the baseline glucose tolerance test. In some embodiments, the composition reduces the glucose AUC measurement relative to the baseline glucose AUC measurement.

In some embodiments, the glucose measurement is decreased by about 2.5% or more, about 5% or more, or about 7.5% or more, relative to the baseline glucose measurement. In some embodiments, the glucose measurement is decreased by about 10% or more, relative to the baseline glucose measurement. In some embodiments, the glucose measurement is decreased by about 20% or more, about 30% or more, about 40% or more, about 50% or more, about 60% or more, about 70% or more, about 80% or more, about 90% or more, or about 100%, relative to the baseline glucose measurement. In some embodiments, the glucose is decreased by no more than about 2.5%, no more than about 5%, or no more than about 7.5%, relative to the baseline glucose measurement. In some embodiments, the glucose is decreased by no more than about 10%, relative to the baseline glucose measurement. In some embodiments, the glucose is decreased by no more than about 20%, no more than about 30%, no more than about 40%, no more than about 50%, no more than about 60%, no more than about 70%, no more than about 80%, no more than about 90%, or no more than about 100% relative to the baseline glucose measurement. In some embodiments, the glucose measurement is decreased by 2.5%, 5%, 7.5%, 10%, 20%, 30%, 40%, 50%, 60%, 70%, 80%, 90%, 100%, or by a range defined by any of the two aforementioned percentages.

In some embodiments, the measurement is an insulin measurement. In some embodiments, the insulin measurement is an insulin sensitivity measurement. In some embodiments, the insulin sensitivity measurement is obtained using a glucose clamp technique such as a hyperinsulinemic euglycemic clamp. In some embodiments, the insulin measurement comprises an insulin concentration. In some embodiments, the insulin measurement is an insulin concentration. In some embodiments, the insulin measurement is a circulating insulin measurement. In some embodiments, the insulin measurement is obtained by an assay such as an immunoassay, a colorimetric assay, or a fluorescence assay.

In some embodiments, the insulin sensitivity measurement comprises a glucose tolerance test. In some embodiments, the insulin sensitivity measurement comprises an insulin sensitivity measurement other than a glucose tolerance test.

In some embodiments, the insulin measurement comprises an insulin response test. In some embodiments, the insulin response test comprises administering glucose to the subject, and then obtaining multiple insulin measurements over time after administering the glucose to the subject. In some embodiments, the glucose is administered orally. In some embodiments, the glucose is administered by injection. In some embodiments, the multiple insulin measurements are integrated into an insulin AUC measurement. In some embodiments, the insulin response test is performed on the subject in a fasted state such as after an overnight fast.

In some embodiments, the insulin measurement comprises a glucose response test. In some embodiments, the glucose response test comprises administering insulin to the subject, and then obtaining multiple glucose measurements over time after administering the insulin to the subject. In some embodiments, the insulin is administered by injection. In some embodiments, the multiple glucose measurements are integrated into a glucose AUC measurement. In some embodiments, the multiple glucose measurements are measured with a glucometer. In some embodiments, the glucose response test is performed on the subject in a fasted state such as after an overnight fast. In some embodiments, the glucose response test is performed on the subject after administering food, drink, or glucose to the subject.

In some embodiments, the composition increases the insulin sensitivity relative to the baseline insulin sensitivity measurement. In some embodiments, the insulin sensitivity is increased by about 2.5% or more, about 5% or more, or about 7.5% or more, relative to the baseline insulin sensitivity measurement. In some embodiments, the insulin sensitivity is increased by about 10% or more, relative to the baseline insulin sensitivity measurement. In some embodiments, the insulin sensitivity is increased by about 20% or more, about 30% or more, about 40% or more, about 50% or more, about 60% or more, about 70% or more, about 80% or more, about 90% or more, or about 100% or more relative to the baseline insulin sensitivity measurement. In some embodiments, the insulin sensitivity is increased by about 200% or more, about 300% or more, about 400% or more, about 500% or more, about 600% or more, about 700% or more, about 800% or more, about 900% or more, or about 1000% or more, relative to the baseline insulin sensitivity measurement. In some embodiments, the insulin sensitivity is increased by no more than about 2.5%, no more than about 5%, or no more than about 7.5%, relative to the baseline insulin sensitivity measurement. In some embodiments, the insulin sensitivity is increased by no more than about 10%, relative to the baseline insulin sensitivity measurement. In some embodiments, the insulin sensitivity is increased by no more than about 20%, no more than about 30%, no more than about 40%, no more than about 50%, no more than about 60%, no more than about 70%, no more than about 80%, no more than about 90%, or no more than about 100% relative to the baseline insulin sensitivity measurement. In some embodiments, the insulin sensitivity is increased by no more than about 200%, no more than about 300%, no more than about 400%, no more than about 500%, no more than about 600%, no more than about 700%, no more than about 800%, no more than about 900%, or no more than about 1000%, relative to the baseline insulin sensitivity measurement. In some embodiments, the insulin sensitivity is increased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the composition reduces the insulin measurement relative to the baseline insulin measurement. In some embodiments, the composition reduces circulating insulin relative to the baseline insulin measurement. In some embodiments, the reduced insulin is measured in a second sample obtained from the subject after administering the composition to the subject. In some embodiments, the composition reduces the insulin AUC measurement relative to the baseline insulin AUC measurement.

In some embodiments, the insulin measurement is decreased by about 2.5% or more, about 5% or more, or about 7.5% or more, relative to the baseline insulin measurement. In some embodiments, the insulin measurement is decreased by about 10% or more, relative to the baseline insulin measurement. In some embodiments, the insulin measurement is decreased by about 20% or more, about 30% or more, about 40% or more, about 50% or more, about 60% or more, about 70% or more, about 80% or more, about 90% or more, or about 100%, relative to the baseline insulin measurement. In some embodiments, the insulin is decreased by no more than about 2.5%, no more than about 5%, or no more than about 7.5%, relative to the baseline insulin measurement. In some embodiments, the insulin is decreased by no more than about 10%, relative to the baseline insulin measurement. In some embodiments, the insulin is decreased by no more than about 20%, no more than about 30%, no more than about 40%, no more than about 50%, no more than about 60%, no more than about 70%, no more than about 80%, no more than about 90%, or no more than about 100% relative to the baseline insulin measurement. In some embodiments, the insulin measurement is decreased by 2.5%, 5%, 7.5%, 19%, 20%, 30%, 40%, 50%, 60%, 70%, 80%, 90%, 100%, or by a range defined by any of the two aforementioned percentages.

In some embodiments, the measurement is an ANGPTL4 protein measurement. In some embodiments, the ANGPTL4 protein measurement comprises an ANGPTL4 protein level. In some embodiments, the ANGPTL4 protein level is indicated as a mass or percentage of ANGPTL4 protein per sample weight. In some embodiments, the ANGPTL4 protein level is indicated as a mass or percentage of ANGPTL4 protein per sample volume. In some embodiments, the ANGPTL4 protein level is indicated as a mass or percentage of ANGPTL4 protein per total protein within the sample. In some embodiments, the ANGPTL4 protein measurement is a cell (e.g. hepatocyte) ANGPTL4 protein measurement. In some embodiments, the ANGPTL4 protein measurement is a tissue (e.g. liver tissue) ANGPTL4 protein measurement. In some embodiments, the ANGPTL4 protein measurement is a circulating ANGPTL4 protein measurement. In some embodiments, the baseline ANGPTL4 protein measurement is obtained by an assay such as an immunoassay, a colorimetric assay, or a fluorescence assay.

In some embodiments, the composition reduces the ANGPTL4 protein measurement relative to the baseline ANGPTL4 protein measurement. In some embodiments, the composition reduces circulating ANGPTL4 protein levels relative to the baseline ANGPTL4 protein measurement. In some embodiments, the composition reduces tissue ANGPTL4 protein levels (such as liver tissue ANGPTL protein levels) relative to the baseline ANGPTL4 protein measurement. In some embodiments, the composition reduces cell ANGPTL4 protein levels (such as hepatocyte ANGPTL protein levels) relative to the baseline ANGPTL4 protein measurement. In some embodiments, the reduced ANGPTL4 protein levels are measured in a second sample obtained from the subject after administering the composition to the subject.

In some embodiments, the ANGPTL4 protein measurement is decreased by about 2.5% or more, about 5% or more, or about 7.5% or more, relative to the baseline ANGPTL4 protein measurement. In some embodiments, the ANGPTL4 protein measurement is decreased by about 10% or more, relative to the baseline ANGPTL4 protein measurement. In some embodiments, the ANGPTL4 protein measurement is decreased by about 20% or more, about 30% or more, about 40% or more, about 50% or more, about 60% or more, about 70% or more, about 80% or more, about 90% or more, or about 100%, relative to the baseline ANGPTL4 protein measurement. In some embodiments, the ANGPTL4 protein measurement is decreased by no more than about 2.5%, no more than about 5%, or no more than about 7.5%, relative to the baseline ANGPTL4 protein measurement. In some embodiments, the ANGPTL4 protein measurement is decreased by no more than about 10%, relative to the baseline ANGPTL4 protein measurement. In some embodiments, the ANGPTL4 protein measurement is decreased by no more than about 20%, no more than about 30%, no more than about 40%, no more than about 50%, no more than about 60%, no more than about 70%, no more than about 80%, no more than about 90%, or no more than about 100% relative to the baseline ANGPTL4 protein measurement. In some embodiments, the ANGPTL4 protein measurement is decreased by 2.5%, 5%, 7.5%, 19%, 20%, 30%, 40%, 50%, 60%, 70%, 80%, 90%, 100%, or by a range defined by any of the two aforementioned percentages.

In some embodiments, the measurement is an ANGPTL4 mRNA measurement. In some embodiments, the ANGPTL4 mRNA measurement comprises an ANGPTL4 mRNA level. In some embodiments, the ANGPTL4 mRNA level is indicated as a mass or percentage of ANGPTL4 mRNA per sample weight. In some embodiments, the ANGPTL4 mRNA level is indicated as a mass or percentage of ANGPTL4 mRNA per sample volume. In some embodiments, the ANGPTL4 mRNA level is indicated as a mass or percentage of ANGPTL4 mRNA per total mRNA within the sample. In some embodiments, the ANGPTL4 mRNA level is indicated as a mass or percentage of ANGPTL4 mRNA per total nucleic acids within the sample. In some embodiments, the ANGPTL4 mRNA level is indicated relative to another mRNA level, such as an mRNA level of a housekeeping gene, within the sample. In some embodiments, the ANGPTL4 mRNA measurement is obtained by an assay such as a PCR assay. In some embodiments, the PCR comprises qPCR. In some embodiments, the PCR comprises reverse transcription of the ANGPTL4 mRNA.

In some embodiments, the composition reduces the ANGPTL4 mRNA measurement relative to the baseline ANGPTL4 mRNA measurement. In some embodiments, the ANGPTL4 mRNA measurement is obtained in a second sample obtained from the subject after administering the composition to the subject. In some embodiments, the composition reduces ANGPTL4 mRNA levels relative to the baseline ANGPTL4 mRNA levels. In some embodiments, the reduced ANGPTL4 mRNA levels are measured in a second sample obtained from the subject after administering the composition to the subject. In some embodiments, the second sample is a liver sample. In some embodiments, the second sample is an adipose sample.

In some embodiments, the ANGPTL4 mRNA measurement is reduced by about 2.5% or more, about 5% or more, or about 7.5% or more, relative to the baseline ANGPTL4 mRNA measurement. In some embodiments, the ANGPTL4 mRNA measurement is decreased by about 10% or more, relative to the baseline ANGPTL4 mRNA measurement. In some embodiments, the ANGPTL4 mRNA measurement is decreased by about 20% or more, about 30% or more, about 40% or more, about 50% or more, about 60% or more, about 70% or more, about 80% or more, about 90% or more, or about 100%, relative to the baseline ANGPTL4 mRNA measurement. In some embodiments, the ANGPTL4 mRNA measurement is decreased by no more than about 2.5%, no more than about 5%, or no more than about 7.5%, relative to the baseline ANGPTL4 mRNA measurement. In some embodiments, the ANGPTL4 mRNA measurement is decreased by no more than about 10%, relative to the baseline ANGPTL4 mRNA measurement. In some embodiments, the ANGPTL4 mRNA measurement is decreased by no more than about 20%, no more than about 30%, no more than about 40%, no more than about 50%, no more than about 60%, no more than about 70%, no more than about 80%, no more than about 90%, or no more than about 100% relative to the baseline ANGPTL4 mRNA measurement. In some embodiments, the ANGPTL4 mRNA measurement is decreased by 2.5%, 5%, 7.5%, 10%, 20%, 30%, 40%, 50%, 60%, 70%, 80%, 90%, 100%, or by a range defined by any of the two aforementioned percentages.

III. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," and "patient" may be used interchangeably herein. A "subject" can be a biological entity containing expressed genetic materials. The biological entity can be a plant, animal, or microorganism, including, for example, bacteria, viruses, fungi, and protozoa. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

IV. Sequence Information

Some embodiments include one or more nucleic acid sequences in the following table:

TABLE 1

| SEQ ID NO: | Description |
|---|---|
| 1-1854 & 13970-13977 | ANGPTL4 siRNA oligonucleotide sense strand sequences |
| 1855-3708 & 13978-13985 | ANGPTL4 siRNA oligonucleotide antisense strand sequences |
| 3709-13934 | ANGPTL4 ASO sequences |
| 13935 | Full-length human ANGPTL4 human mRNA sequence (GenBank Acc.# NM_139314.3) |
| 13936 | Full-length ANGPTL4 human pre-mRNA sequence (NC_00019.10: 8364129-8374373) |
| 13937-13944 | Sequences for siRNA sense strands targeting mouse ANGPTL4 |
| 13945-13952 | Sequences for siRNA antisense strands targeting mouse ANGPTL4 |
| 13953 | Non-targeting control ASO oligonucleotide sequence |
| 13954-13959 | Modification pattern 1S to 6S |
| 13960-13968 | Modification pattern 1AS to 9AS |
| 13969 | Modification pattern ASO1 |

TABLE 1-continued

| SEQ ID NO: | Description |
|---|---|
| 13986-14133 | Modified ANGPTL4 siRNA oligonucleotide sense strand sequences |
| 14134-14288 | Modified ANGPTL4 siRNA oligonucleotide antisense strand sequences |
| 14289-14290 | ETD00971 sense and antisense strands |
| 14291-14292 | ETD00959 sense and antisense strands |

V. Embodiments

Some embodiments include one or more of the following:

1. A composition comprising an oligonucleotide that targets Angiopoietin-like 4 (ANGPTL4) and when administered to a subject in an effective amount decreases circulating triglycerides.

2. The composition of embodiment 1, wherein the triglycerides are decreased by about 10% or more, as compared to prior to administration.

3. A composition comprising an oligonucleotide that targets ANGPTL4 and when administered to a subject in an effective amount decreases circulating total cholesterol.

4. The composition of embodiment 3, wherein the total cholesterol is decreased by about 10% or more, as compared to prior to administration.

5. A composition comprising an oligonucleotide that targets ANGPTL4 and when administered to a subject in an effective amount increases circulating high-density lipoproteins (HDL).

6. The composition of embodiment 5, wherein the HDL are increased by about 10% or more, as compared to prior to administration.

7. A composition comprising an oligonucleotide that targets ANGPTL4 and when administered to a subject in an effective amount decreases circulating glucose.

8. The composition of embodiment 7, wherein the glucose is decreased by about 10% or more, as compared to prior to administration.

9. A composition comprising an oligonucleotide that targets ANGPTL4 and when administered to a subject in an effective amount increases insulin sensitivity.

10. The composition of embodiment 9, wherein the insulin sensitivity is increased by about 10% or more, as compared to prior to administration.

11. The composition of any one of embodiments 1-10, wherein the oligonucleotide comprises a modified internucleoside linkage.

12. The composition of embodiment 11, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

13. The composition of embodiment 11, wherein the modified internucleoside linkage comprises one or more phosphorothioate linkages.

14. The composition of any one of embodiments 1-13, wherein the oligonucleotide comprises 1, 2, 3, 4, 5, 6, 7, 8, 9, 10, 11, 12, 13, 14, 15, 16, 17, 18, 19, or 20 modified internucleoside linkages.

15. The composition of any one of embodiments 1-14, wherein the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

16. The composition of any one of embodiments 1-15, wherein the oligonucleotide comprises a modified nucleoside.

17. The composition of embodiment 16, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

18. The composition of embodiment 16, wherein the modified nucleoside comprises a LNA.

19. The composition of embodiment 16, wherein the modified nucleoside comprises a 2',4' constrained ethyl nucleic acid.

20. The composition of embodiment 16, wherein the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

21. The composition of embodiment 16, wherein the modified nucleoside comprises one or more 2'fluoro modified nucleosides.

22. The composition of embodiment 16, wherein the modified nucleoside comprises a 2' O-alkyl modified nucleoside.

23. The composition of embodiment 16, wherein the oligonucleotide comprises a lipid attached at a 3' or 5' terminus of the oligonucleotide.

24. The composition of embodiment 23, wherein the lipid comprises cholesterol, myristoyl, palmitoyl, stearoyl, lithocholoyl, docosanoyl, docosahexaenoyl, myristyl, palmityl stearyl, or α-tocopherol, or a combination thereof.

25. The composition of any one of embodiments 1-24, wherein the oligonucleotide comprises 1, 2, 3, 4, 5, 6, 7, 8, 9, 10, 11, 12, 13, 14, 15, 16, 17, 18, 19, 20, or 21 modified nucleosides.

26. The composition of any one of embodiments 1-25, wherein the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

27. The composition of any one of embodiments 1-26, wherein the oligonucleotide comprises an N-acetylgalactosamine (GalNAc) ligand for hepatocyte targeting.

28. The composition of any one of embodiments 1-27, wherein the oligonucleotide comprises a small interfering RNA (siRNA) comprising a sense strand and an antisense strand.

29. The composition of embodiment 28, wherein the sense strand is 14-30 nucleosides in length.

30. The composition of embodiment 28 or 29, wherein the antisense strand is 14-30 nucleosides in length.

31. A composition comprising an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13935.

32. A composition comprising an oligonucleotide that inhibits the expression of ANGPTL4, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13936.

33. The composition of any one of embodiments 28-32, wherein the sense strand and the antisense strand form a double-stranded RNA duplex.

34. The composition of embodiment 33, wherein the first base pair of the double-stranded RNA duplex is an AU base pair.

35. The composition of any one of embodiments 28-34, wherein the sense strand comprises a 3' overhang comprising 1, 2, or more nucleosides.

36. The composition of embodiment 35, wherein the 3' overhang of the sense strand comprises 2 nucleosides.

37. The composition of any one of embodiments 28-36, wherein the antisense strand comprises a 3' overhang comprising 1, 2, or more nucleosides.

38. The composition of embodiment 37, wherein the 3' overhang of the antisense strand comprises 2 nucleosides.

39. The composition of any one of embodiments 28-38, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions.

40. The composition of any one of embodiments 28-39, wherein the sense strand comprises a nucleoside sequence comprising or consisting of the sequence of any one of SEQ ID NOs: 1-1854 or 13970-13977.

41. The composition of any one of embodiments 28-40, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions.

42. The composition of any one of embodiments 28-41, wherein the antisense strand comprises a nucleoside sequence comprising or consisting of the sequence of any one of SEQ ID NOs: 1855-3708 or 13978-13985.

43. The composition of any one of embodiments 28-42, wherein the siRNA binds with a 17mer in a non-human primate ANGPTL4 mRNA.

44. The composition of any one of embodiments 28-43, wherein the siRNA binds with a 19mer in a human ANGPTL4 mRNA.

45. The composition of any one of embodiments 28-44, wherein the siRNA binds with a human ANGPTL4 mRNA and less than or equal to 20 human off-targets, with no more than 2 mismatches in the antisense strand.

46. The composition of any one of embodiments 28-45, wherein the siRNA binds with a human ANGPTL4 mRNA target site that does not harbor an SNP, with a minor allele frequency (MAF) greater or equal to 1% (pos. 2-18).

47. The composition of any one of embodiments 28-46, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside substitutions, additions, or deletions; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside substitutions, additions, or deletions.

48. The composition of any one of embodiments 28-47, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657.

49. The composition of any one of embodiments 28-48, wherein the sense strand comprises the nucleoside sequence of any one of SEQ ID NOs: 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, or 1787; and wherein the antisense strand comprises the nucleoside sequence of any one of SEQ ID NOs: 1887, 1888, 1889, 1890, 1910, 1975, 2126, 2134, 2136, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2335, 2338, 2363, 2371, 2373, 2374, 2419, 2474, 2489, 2491, 2494, 2684, 2688, 2695, 2696, 2697, 2698, 2704, 2725, 2726, 2730, 2741, 2742, 2748, 2751, 2756, 2799, 2855, 2856, 2859, 2891, 2987, 2988, 2991, 3003, 3005, 3007, 3008, 3009, 3011, 3012, 3015, 3016, 3018, 3019, 3020, 3025, 3026, 3102, 3103, 3169, 3192, 3197, 3201, 3202, 3283, 3284, 3424, 3425, 3426, 3464, 3465, 3471, 3634, 3638, or 3641.

50. The composition of any one of embodiments 28-49, wherein the sense strand comprises the nucleoside sequence of any one of SEQ ID NOs: 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, or 1803; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1966, 1970, 1971, 1972, 1973, 1974, 1979, 1980, 1981, 1982, 1983, 2003, 2004, 2006, 2007, 2011, 2012, 2013, 2015, 2018, 2019, 2020, 2021, 2022, 2023, 2026, 2028, 2029, 2050, 2053, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2234, 2236, 2240, 2242, 2245, 2246, 2247, 2248, 2251, 2252, 2253, 2256, 2258, 2259, 2265, 2266, 2267, 2268, 2269, 2274, 2275, 2276, 2277, 2278, 2279, 2280, 2281, 2282, 2283, 2284, 2285, 2289, 2338, 2371, 2373, 2374, 2419, 2424, 2425, 2426, 2461, 2462, 2464, 2465, 2466, 2470, 2471, 2474, 2489, 2491, 2494, 2526, 2527, 2528, 2529, 2530, 2531, 2532, 2533, 2535, 2536, 2537, 2538, 2540, 2541, 2543, 2546, 2549, 2684, 2695, 2696, 2697, 2698, 2704, 2705, 2706, 2707, 2708, 2710, 2711, 2720, 2722, 2725, 2726, 2730, 2741, 2742, 2744, 2746, 2747, 2748, 2756, 2765, 2766, 2767, 2768, 2769, 2770, 2771, 2772, 2773, 2774, 2775, 2776, 2799, 2855, 2856, 2859, 2860, 2863, 2864, 2865, 2867, 2882, 2886, 2906, 2907, 2908, 2909, 2911, 2912, 2966, 2976, 2978, 2980, 2981, 2987, 2988, 3001, 3002, 3003, 3005, 3007, 3008, 3009, 3011, 3012, 3015, 3016, 3018, 3019, 3020, 3029, 3036, 3038, 3106, 3107, 3113, 3130, 3139, 3164, 3169, 3197, 3201, 3202, 3203, 3204, 3205, 3259, 3261, 3267, 3268, 3269, 3270, 3271, 3272, 3283, 3284, 3302, 3373, 3377, 3410, 3415, 3417, 3418, 3419, 3425, 3426, 3434, 3435, 3443, 3451, 3455, 3456, 3457, 3458, 3459, 3460, 3465, 3467, 3468, 3547, 3553, 3555, 3556, 3557, 3576, 3594, 3595, 3596, 3599, 3601, 3602, 3603, 3605, 3608, 3609, 3633, 3634, 3638, 3642, 3652, 3653, 3655, 3656, or 3657.

51. The composition of any one of embodiments 28-50, wherein the sense strand comprises the nucleoside sequence of any one of SEQ ID NOs: 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, or 1784; and wherein the antisense strand comprises the nucleoside sequence of any one of SEQ ID NOs: 1887, 1888, 1889, 1890, 1910, 2126, 2134, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2338, 2371, 2373, 2374, 2419, 2474, 2489, 2491, 2494, 2684, 2695, 2696, 2697, 2698, 2704, 2725, 2726, 2730, 2741, 2742, 2748, 2756, 2799, 2855, 2856, 2859, 2987, 2988, 3003, 3005, 3007, 3008, 3009, 3011, 3012, 3015, 3016, 3018, 3019, 3020, 3169, 3197, 3201, 3202, 3283, 3284, 3425, 3426, 3465, 3634, or 3638.

52. The composition of any one of embodiments 28-51, wherein the antisense strand comprises a seed region that is not identical to a seed region of a human miRNA.

53. The composition of any one of embodiments 28-52, wherein the sense strand comprises the nucleoside sequence of any one of SEQ ID NOs: 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, or 1803, or 3638; and wherein the antisense strand comprises the nucleoside sequence of any one of SEQ ID NOs: 1886, 1890, 1910, 1911, 1912, 1915, 1916, 1933, 1934, 1971, 1973, 1979, 1980, 1982, 2003, 2006, 2011, 2012, 2013, 2015, 2019, 2020, 2021, 2022, 2023, 2028, 2050, 2065, 2066, 2071, 2072, 2073, 2084, 2085, 2099, 2100, 2107, 2114, 2115, 2116, 2125, 2126, 2134, 2143, 2145, 2146, 2147, 2158, 2175, 2177, 2179, 2180, 2182, 2184, 2185, 2186, 2187, 2188, 2191, 2192, 2196, 2201, 2203, 2206, 2207, 2210, 2234, 2236, 2240, 2242, 2245, 2246, 2248, 2253, 2267, 2268, 2269, 2276, 2277, 2278, 2279, 2280, 2289, 2371, 2373, 2374, 2419, 2425, 2461, 2462, 2466, 2471, 2474, 2489, 2494, 2526, 2527, 2528, 2529, 2532, 2533, 2535, 2537, 2538, 2541, 2546, 2696, 2697, 2704, 2705, 2708, 2720, 2722, 2730, 2746, 2747, 2756, 2765, 2766, 2767, 2768, 2770, 2773, 2799, 2855, 2856, 2860, 2864, 2882, 2906, 2907, 2908, 2909, 2911, 2966, 2978, 2981, 3001, 3003, 3005, 3007, 3009, 3011, 3018, 3029, 3036, 3038, 3113, 3130, 3139, 3169, 3197, 3203, 3204, 3205, 3259, 3261, 3267, 3269, 3272, 3418, 3425, 3435, 3443, 3451, 3455, 3456, 3457, 3458, 3459, 3460, 3467, 3468, 3547, 3555, 3576, 3594, 3599, 3605, 3609, 3655, 3656, or 3657.

54. The composition of any one of embodiments 28-53, wherein the sense strand comprises the nucleoside sequence of any one of SEQ ID 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, or 1571; and wherein the antisense strand comprises the nucleoside sequence of any one of SEQ ID 1890, 1910, 2126, 2134, 2143, 2145, 2146, 2147, 2175, 2177, 2180, 2182, 2184, 2185, 2186, 2187, 2188, 2191, 2192, 2196, 2201, 2203, 2289, 2371, 2373, 2374, 2419, 2474, 2489, 2494, 2696, 2697, 2704, 2730, 2756, 2799, 2855, 2856, 3003, 3005, 3007, 3009, 3011, 3018, 3169, 3197, or 3425.

55. The composition of any one of embodiments 28-54, wherein the sense strand comprises a seed region that is not identical to a seed region of a human miRNA.

56. The composition of any one of embodiments 28-55, wherein the sense strand comprises the nucleoside sequence of any one of SEQ ID NOs: 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, or 1787; and wherein the antisense strand comprises the nucleoside sequence of any one of SEQ ID NOs: 1886, 1890, 1910, 1912, 1915, 1916, 1934, 1971, 1973, 1980, 2006, 2008, 2011, 2012, 2013, 2015, 2020, 2023, 2028, 2031, 2050, 2065, 2066, 2071, 2072, 2084, 2085, 2099, 2107, 2114, 2115, 2125, 2126, 2134, 2143, 2147, 2158, 2182, 2184, 2185, 2186, 2187, 2188, 2191, 2196, 2201, 2203, 2207, 2210, 2240, 2242, 2245, 2246, 2248, 2268, 2269, 2276, 2277, 2278, 2280, 2289, 2374, 2425, 2462, 2466, 2471, 2507, 2526, 2532, 2533, 2535, 2537, 2546, 2696, 2697, 2705, 2708, 2713, 2730, 2746, 2754, 2767, 2768, 2773, 2822, 2855, 2856, 2908, 2911, 2918, 2966, 2978, 3011, 3018, 3036, 3038, 3102, 3113, 3197, 3205, 3206, 3269, 3272, 3418, 3435, 3456, 3468, 3547, 3555, 3576, 3594, 3605, 3609, or 3641.

57. The composition of any one of embodiments 28-56, wherein the sense strand comprises the nucleoside sequence of any one of SEQ ID NOs: 36, 56, 272, 280, 289, 293, 328, 330, 331, 332, 333, 334, 337, 342, 347, 349, 435, 520, 842, 843, 876, 1001, 1002, 1157, 1164, or 1343; and wherein the antisense strand comprises the nucleoside sequence of any one of SEQ ID NOs: 1890, 1910, 2126, 2134, 2143, 2147, 2182, 2184, 2185, 2186, 2187, 2188, 2191, 2196, 2201, 2203, 2289, 2374, 2696, 2697, 2730, 2855, 2856, 3011, 3018, or 3197.

58. The composition of any one of embodiments 28-57, wherein the sense strand comprises modification pattern 1S: 5'-NfsnsNfnNfnNfNfNfnNfnNfnNfnNfnNfsnsn-3', wherein "Nf" is a 2' fluoro-modified nucleoside, "n" is a 2' O-methyl modified nucleoside, and "s" is a phosphorothioate linkage.

59. The composition of any one of embodiments 28-57, wherein the sense strand comprises modification pattern 2S: 5'-nsnsnnNfnNfNfNfnnnnnnnnnnnsnsn-3', wherein "Nf" is a 2' fluoro-modified nucleoside, "n" is a 2' O-methyl modified nucleoside, and "s" is a phosphorothioate linkage.

60. The composition of any one of embodiments 28-57, wherein the sense strand comprises modification pattern 3S: 5'-nsnsnnNfnNfnNfnNfnnnnnnnnnnnsnsn-3', wherein "Nf" is a 2' fluoro-modified nucleoside, "n" is a 2' O-methyl modified nucleoside, and "s" is a phosphorothioate linkage.

61. The composition of any one of embodiments 28-57, wherein the sense strand comprises modification pattern 4S: 5'-NfsnsNfnNfnNfnNfNfnNfnNfnNfnNfnNfsnsnN-3', wherein "Nf" is a 2' fluoro-modified nucleoside, "n" is a 2' O-methyl modified nucleoside, "s" is a phosphorothioate linkage, and N comprises one or more nucleosides.

62. The composition of any one of embodiments 28-57, wherein the sense strand comprises modification pattern 5S: 5'-nsnsnnNfnNfNfNfnnnnnnnnnnsnsnN-3', wherein "Nf" is a 2' fluoro-modified nucleoside, "n" is a 2' O-methyl modified nucleoside, "s" is a phosphorothioate linkage, and N comprises one or more nucleosides.

63. The composition of any one of embodiments 28-62, wherein the antisense strand comprises modification pattern 1AS: 5'-nsNfsnNfnNfnNfnNfnnnNfnNfnNfsnsn-3', wherein "Nf" is a 2' fluoro-modified nucleoside, "n" is a 2' O-methyl modified nucleoside, and "s" is a phosphorothioate linkage.

64. The composition of any one of embodiments 28-62, wherein the antisense strand comprises modification pattern 2AS: 5'-nsNfsnnnNfnNfNfnnnnNfnNfnnnsnsn-3', wherein "Nf" is a 2' fluoro-modified nucleoside, "n" is a 2' O-methyl modified nucleoside, and "s" is a phosphorothioate linkage.

65. The composition of any one of embodiments 28-62, wherein the antisense strand comprises modification pattern 3AS: 5'-nsNfsnnnNfnnnnnnnNfnNfnnnsnsn-3', wherein "Nf" is a 2' fluoro-modified nucleoside, "n" is a 2' O-methyl modified nucleoside, and "s" is a phosphorothioate linkage.

66. The composition of any one of embodiments 28-62, wherein the antisense strand comprises modification pattern 4AS: 5'-nsNfsnNfnNfnnnnnnnNfnNfnnnsnsn-3', wherein "Nf" is a 2' fluoro-modified nucleoside, "n" is a 2' O-methyl modified nucleoside, and "s" is a phosphorothioate linkage.

67. The composition of any one of embodiments 28-57, wherein the sense strand comprises modification pattern 1S and the antisense strand comprises modification pattern 1AS, 2AS, 3AS, or 4AS.

68. The composition of any one of embodiments 28-57, wherein the sense strand comprises modification pattern 2S and the antisense strand comprises modification pattern 1AS, 2AS, 3AS, or 4AS.

69. The composition of any one of embodiments 28-57, wherein the sense strand comprises modification pattern 3S and the antisense strand comprises modification pattern 1AS, 2AS, 3AS, or 4AS.

70. The composition of any one of embodiments 28-57, wherein the sense strand comprises modification pattern 4S and the antisense strand comprises modification pattern 1AS, 2AS, 3AS, or 4AS.

71. The composition of any one of embodiments 28-57, wherein the sense strand comprises a nucleoside sequence comprising or consisting of the sequence of any one of SEQ ID NOs: 1-1854 or 13970-13977, a nucleic acid sequence thereof having 1 or 2 nucleoside substitutions, additions, or deletions, and modification pattern 1S.

72. The composition of any one of embodiments 28-57, wherein the sense strand comprises a nucleoside sequence comprising or consisting of the sequence of any one of SEQ ID NOs: 1-1854 or 13970-13977, and modification pattern 1S.

73. The composition of any one of embodiments 28-57, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2S.

74. The composition of any one of embodiments 28-57, wherein the sense strand comprises a nucleoside sequence comprising or consisting of the sequence of any one of SEQ ID NOs: 1-1854 or 13970-13977, and modification pattern 2S.

75. The composition of any one of embodiments 28-57 or 71-74, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 1AS.

76. The composition of any one of embodiments 28-57 or 71-74, wherein the antisense strand comprises a nucleoside sequence comprising or consisting of the sequence of any one of SEQ ID NOs: 1855-3708 or 13978-13985, and modification pattern 1AS.

77. The composition of any one of embodiments 28-57 or 71-74, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 3AS.

78. The composition of any one of embodiments 28-57 or 71-74, wherein the antisense strand comprises a nucleoside sequence comprising or consisting of the sequence of any one of SEQ ID NOs: 1855-3708 or 13978-13985, and modification pattern 3AS.

79. The composition of any one of embodiments 1-27, wherein the oligonucleotide comprises an antisense oligonucleotide (ASO).

80. The composition of embodiment 79, wherein the ASO is 12-30 nucleosides in length.

81. A composition comprising an oligonucleotide that inhibits the expression of ANGPTL4, wherein the oligonucleotide comprises an ASO about 12-30 nucleosides in length and comprising a nucleoside sequence complementary to about 12-30 contiguous nucleosides of SEQ ID NO: 13935.

82. A composition comprising an oligonucleotide that inhibits the expression of ANGPTL4, wherein the oligonucleotide comprises an ASO about 12-30 nucleosides in length and comprising a nucleoside sequence complementary to about 12-30 contiguous nucleosides of SEQ ID NO: 13936.

83. The composition of any one of embodiments 79-82, wherein the ASO is 15-25 nucleosides in length.

84. The composition of any one of embodiments 79-83, wherein the ASO is 20 nucleosides in length.

85. The composition of any one of embodiments 79-84, wherein the ASO comprises a nucleoside sequence comprising or consisting of the sequence of any one of SEQ ID NOs: 3709-13934, or a nucleic acid sequence thereof having 1 or 2 nucleoside substitutions, additions, or deletions.

86. The composition of any one of embodiments 79-85, wherein the ASO comprises a nucleoside sequence comprising or consisting of the sequence of any one of SEQ ID NOs: 3709-13934.

87. The composition of any one of embodiments 79-86, wherein the ASO comprises modification pattern: 5'-nsnsns-nsnsdNsdNsdNsdNsdNsdNsdNsdNsdNsnsnsnsnsn-3' where "dN" is any deoxynucleotide, "n" is a 2'O-methyl or 2'O-methoxyethyl-modified nucleoside, and "s" is a phosphorothioate linkage.

88. The composition of any one of embodiments 79-86, wherein the ASO comprises a nucleoside sequence comprising or consisting of the sequence of any one of SEQ ID NOs: 3709-13934, or a nucleic acid sequence thereof having 1 or 2 nucleoside substitutions, additions, or deletions, and modification pattern ASO1.

89. The composition of any one of embodiments 79-86, wherein the ASO comprises a nucleoside sequence comprising or consisting of the sequence of any one of SEQ ID NOs: 3709-13934, and modification pattern ASO1.

90. The composition of any one of embodiments 1-89, wherein the composition is a pharmaceutical composition.

91. The composition of any one of embodiments 1-90, wherein the composition is sterile. 92. The composition of any one of embodiments 1-91, further comprising a pharmaceutically acceptable carrier.

93. The composition of embodiment 92, wherein the pharmaceutically acceptable carrier comprises water, a buffer, or a saline solution.

94. Use of a composition comprising an oligonucleotide that targets ANGPTL4 in a method of treating a metabolic disorder in a subject in need thereof, the method comprising administering to the subject the composition.

95. The use of embodiment 94, wherein the metabolic disorder comprises hyperlipidemia.

96. The use of embodiment 94, wherein the metabolic disorder comprises hypertriglyceridemia.

97. The use of embodiment 94, wherein the metabolic disorder comprises diabetes.

98. The use of embodiment 94, wherein the metabolic disorder comprises type 2 diabetes.

99. Use of a composition comprising an oligonucleotide that targets ANGPTL4 in a method of treating a cardiovascular disorder in a subject in need thereof, the method comprising administering to the subject the composition.

100. The use of embodiment 99, wherein the cardiovascular disorder comprises heart disease.

101. The use of embodiment 99, wherein the cardiovascular disorder comprises myocardial infarction.

102. The use of embodiment 99, wherein the cardiovascular disorder comprises angina pectoris.

103. The use of embodiment 99, wherein the cardiovascular disorder comprises atherosclerosis.

104. The use of any one of embodiments 94-103, wherein the subject is an animal, a mammal, a dog, a cat, cattle, a rodent, a mouse, a rat, a primate, or a monkey.

105. The use of any one of embodiments 94-104, wherein the subject is a human.

106. The use of any one of embodiments 94-105, wherein the subject is ≥40 years of age.

107. The use of any one of embodiments 94-105, wherein the subject is ≤85 years of age.

108. The use of any one of embodiments 94-105, wherein the subject is ≥40 and ≤85 years of age.

109. The use of any one of embodiments 94-109, wherein a baseline measurement is obtained in a sample obtained from the subject prior to administering the composition to the subject.

110. The use of embodiment 109, wherein the sample is obtained from the subject after an overnight fasting period.

111. The use of embodiment 109, wherein the sample is obtained from the subject in a fed state.

112. The use of one of embodiments 109-111, wherein the baseline measurement is obtained by an immunoassay, a colorimetric assay, or a fluorescence assay.

113. The use of any one of embodiments 109-112, wherein the sample is a blood, plasma, or serum sample.

114. The use of one of embodiments 109-113, wherein the sample is a serum sample. 115. The use of any one of embodiments 109-114, wherein the baseline measurement is a baseline triglyceride measurement.

116. The use of any one of embodiments 109-114, wherein the baseline measurement is a baseline cholesterol measurement.

117. The use of any one of embodiments 109-114, wherein the baseline measurement is a baseline HDL measurement.

118. The use of any one of embodiments 109-114, wherein the baseline measurement is a baseline glucose measurement.

119. The use of any one of embodiments 109-114, wherein the baseline measurement is a baseline insulin sensitivity measurement.

120. The use of any one of embodiments 109-112, wherein the sample is a tissue sample.

121. The use of embodiment 120, wherein the tissue sample comprises liver, adipose, small intestine, mesenteric lymph node, or cardiac tissue.

122. The use of embodiment 120 or 121, wherein the tissue sample is a liver sample.

123. The use of any one of embodiments 109-122, wherein the baseline measurement is a baseline ANGPTL4 protein measurement.

124. The use of any one of embodiments 109-122, wherein the baseline measurement is a baseline ANGPTL4 mRNA measurement.

125. The use of embodiment 124, wherein the baseline measurement is obtained by PCR.

126. The use of embodiment 115, wherein the composition reduces circulating triglycerides relative to the baseline triglyceride measurement.

127. The use of embodiment 126, wherein the reduced triglycerides are measured in a second sample obtained from the subject after administering the composition to the subject.

128. The use of embodiment 116, wherein the composition reduces circulating cholesterol relative to the baseline cholesterol measurement.

129. The use of embodiment 128, wherein the reduced cholesterol is measured in a second sample obtained from the subject after administering the composition to the subject.

130. The use of embodiment 117, wherein the composition increases circulating HDL relative to the baseline HDL measurement.

131. The use of embodiment 130, wherein the increased HDL is measured in a second sample obtained from the subject after administering the composition to the subject.

132. The use of embodiment 118, wherein the composition reduces circulating glucose relative to the baseline glucose measurement.

133. The use of embodiment 132, wherein the reduced glucose is measured in a second sample obtained from the subject after administering the composition to the subject.

134. The use of embodiment 119, wherein the composition improves insulin sensitivity relative to the baseline insulin sensitivity measurement.

135. The use of embodiment 134, wherein the improves insulin sensitivity is measured in a second sample obtained from the subject after administering the composition to the subject.

136. The use of embodiment 123, wherein the composition reduces circulating ANGPTL4 protein levels relative to the baseline ANGPTL4 protein measurement.

137. The use of embodiment 136, wherein the reduced ANGPTL4 protein levels are measured in a second sample obtained from the subject after administering the composition to the subject.

138. The use of embodiment 124 or 125, wherein the composition reduces ANGPTL4 mRNA levels relative to the baseline ANGPTL4 mRNA measurement.

139. The use of embodiment 138, wherein the reduced ANGPTL4 mRNA levels are measured in a second sample obtained from the subject after administering the composition to the subject.

140. The use of any one of embodiments 94-139, wherein the oligonucleotide comprises a modified internucleoside linkage.

141. The use of embodiment 140, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

142. The use of embodiment 140, wherein the modified internucleoside linkage comprises one or more phosphorothioate linkages.

143. The use of any one of embodiments 94-142, wherein the oligonucleotide comprises 1, 2, 3, 4, 5, 6, 7, 8, 9, 10, 11, 12, 13, 14, 15, 16, 17, 18, 19, or 20 modified internucleoside linkages.

144. The use of any one of embodiments 94-143, wherein the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

145. The use of any one of embodiments 94-144, wherein the oligonucleotide comprises a modified nucleoside.

146. The use of embodiment 145, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

147. The use of embodiment 145, wherein the modified nucleoside comprises a LNA.

148. The use of embodiment 145, wherein the modified nucleoside comprises a 2',4' constrained ethyl nucleic acid.

149. The use of embodiment 145, wherein the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

150. The use of embodiment 145, wherein the modified nucleoside comprises one or more 2'fluoro modified nucleosides.

151. The use of embodiment 145, wherein the modified nucleoside comprises a 2' O-alkyl modified nucleoside.

152. The use of embodiment 145, wherein the oligonucleotide comprises a lipid attached at a 3' or 5' terminus of the oligonucleotide.

153. The use of embodiment 152, wherein the lipid comprises cholesterol, myristoyl, palmitoyl, stearoyl, lithocholoyl, docosanoyl, docosahexaenoyl, myristyl, palmityl stearyl, or α-tocopherol, or a combination thereof.

154. The use of any one of embodiments 94-153, wherein the oligonucleotide comprises 1, 2, 3, 4, 5, 6, 7, 8, 9, 10, 11, 12, 13, 14, 15, 16, 17, 18, 19, 20, or 21 modified nucleosides.

155. The use of any one of embodiments 94-154, wherein the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

156. The use of any one of embodiments 94-155, wherein the oligonucleotide comprises an N-acetylgalactosamine (GalNAc) ligand for hepatocyte targeting.

157. The use of any one of embodiments 94-156, wherein the oligonucleotide comprises an siRNA comprising a sense strand and an antisense strand.

158. The use of embodiment 157, wherein the sense strand is 14-30 nucleosides in length.

159. The use of embodiment 157 or 158, wherein the antisense strand is 14-30 nucleosides in length.

160. The use of any one of embodiments 94-156, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13935.

161. The use of any one of embodiments 94-156, wherein the oligonucleotide comprises an siRNA comprising a sense strand and an antisense strand, each strand is independently about 14-30 nucleosides in length, and at least one of the sense strand and the antisense strand comprises a nucleoside sequence comprising about 14-30 contiguous nucleosides of SEQ ID NO: 13936.

162. The use of any one of embodiments 157-161, wherein the sense strand and the antisense strand form a double-stranded RNA duplex.

163. The use of embodiment 162, wherein the first base pair of the double-stranded RNA duplex is an AU base pair.

164. The use of any one of embodiments 157-163, wherein the sense strand comprises a 3' overhang comprising 1, 2, or more nucleosides.

165. The use of embodiment 164, wherein the 3' overhang of the sense strand comprises 2 nucleosides.

166. The use of any one of embodiments 157-165, wherein the antisense strand comprises a 3' overhang comprising 1, 2, or more nucleosides.

167. The use of embodiment 166, wherein the 3' overhang of the antisense strand comprises 2 nucleosides.

168. The use of any one of embodiments 157-167, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions.

169. The use of any one of embodiments 157-168, wherein the sense strand comprises a nucleoside sequence comprising or consisting of the sequence of any one of SEQ ID NOs: 1-1854 or 13970-13977.

170. The use of any one of embodiments 157-169, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions.

171. The use of any one of embodiments 157-170, wherein the antisense strand comprises a nucleoside sequence comprising or consisting of the sequence of any one of SEQ ID NOs: 1855-3708 or 13978-13985.

172. The use of any one of embodiments 157-171, wherein the siRNA binds with a 17mer in a non-human primate ANGPTL4 mRNA.

173. The use of any one of embodiments 157-172, wherein the siRNA binds with a 19mer in a human ANGPTL4 mRNA.

174. The use of any one of embodiments 157-173, wherein the siRNA binds with a human ANGPTL4 mRNA and less than or equal to 20 human off-targets, with no more than 2 mismatches in the antisense strand.

175. The use of any one of embodiments 157-174, wherein the siRNA binds with a human ANGPTL4 mRNA target site that does not harbor an SNP, with a minor allele frequency (MAF) greater or equal to 1% (pos. 2-18).

176. The use of any one of embodiments 157-175, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803, or a nucleic acid sequence thereof having 1 or 2 nucleoside substitutions, additions, or deletions; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657, or a nucleic acid sequence thereof having 1 or 2 nucleoside substitutions, additions, or deletions.

177. The use of any one of embodiments 157-176, wherein the sense strand comprises the nucleoside sequence of any one of SEQ ID NOs: 32, 33, 34, 35, 36, 56, 57, 58, 59, 61, 62, 63, 64, 79, 80, 84, 111, 112, 116, 117, 118, 119, 120, 121, 125, 126, 127, 128, 129, 149, 150, 152, 153, 154, 157, 158, 159, 161, 164, 165, 166, 167, 168, 169, 172, 174, 175, 177, 196, 198, 199, 210, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 282, 289, 290, 291, 292, 293, 299, 304, 321, 323, 325, 326, 328, 329, 330, 331, 332, 333, 334, 335, 337, 338, 339, 342, 347, 349, 350, 352, 353, 356, 377, 380, 382, 386, 388, 391, 392, 393, 394, 397, 398, 399, 402, 404, 405, 411, 412, 413, 414, 415, 417, 419, 420, 421, 422, 423, 424, 425, 426, 427, 428, 429, 430, 431, 435, 481, 484, 506, 509, 517, 519, 520, 565, 570, 571, 572, 589, 607, 608, 610, 611, 612, 616, 617, 620, 623, 635, 637, 640, 643, 653, 672, 673, 674, 675, 676, 677, 678, 679, 681, 682, 683, 684, 686, 687, 689, 692, 695, 830, 834, 841, 842, 843, 844, 850, 851, 852, 853, 854, 856, 857, 859, 866, 868, 871, 872, 876, 887, 888, 890, 892, 893, 894, 897, 900, 902, 907, 911, 912, 913, 914, 915, 916, 917, 918, 919, 920, 921, 922, 925, 945, 968, 1001, 1002, 1005, 1006, 1009, 1010, 1011, 1013, 1028, 1032, 1037, 1052, 1053, 1054, 1055, 1057, 1058, 1064, 1112, 1122, 1124, 1126, 1127, 1133, 1134, 1136, 1137, 1147, 1148, 1149, 1151, 1153, 1154, 1155, 1157, 1158, 1161, 1162, 1163, 1164, 1165, 1166, 1171, 1172, 1175, 1181, 1182, 1184, 1248, 1249, 1252, 1253, 1259, 1276, 1285, 1310, 1315, 1338, 1343, 1347, 1348, 1349, 1350, 1351, 1352, 1378, 1405, 1407, 1413, 1414, 1415, 1416, 1417, 1418, 1429, 1430, 1448, 1477, 1487, 1488, 1489, 1493, 1494, 1519, 1523, 1538, 1556, 1561, 1563, 1564, 1565, 1570, 1571, 1572, 1580, 1581, 1589, 1597, 1598, 1601, 1602, 1603, 1604, 1605, 1606, 1610, 1611, 1613, 1614, 1617, 1693, 1699, 1701, 1702, 1703, 1722, 1740, 1741, 1742, 1745, 1747, 1748, 1749, 1751, 1754, 1755, 1779, 1780, 1784, 1787, 1788, 1798, 1799, 1800, 1801, 1802, or 1803; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1938, 1965, 1966, 1970, 1971, 1972, 1973, 1974, 1975, 1979, 1980, 1981, 1982, 1983, 2003, 2004, 2006, 2007, 2008, 2011, 2012, 2013, 2015, 2018, 2019, 2020, 2021, 2022, 2023, 2026, 2028, 2029, 2031, 2050, 2052, 2053, 2064, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2136, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2231, 2234, 2236, 2240, 2242, 2245, 2246, 2247, 2248, 2251, 2252, 2253, 2256, 2258, 2259, 2265, 2266, 2267, 2268, 2269, 2271, 2273, 2274, 2275, 2276, 2277, 2278, 2279, 2280, 2281, 2282, 2283, 2284, 2285, 2289, 2335, 2338, 2360, 2363, 2371, 2373, 2374, 2419, 2424, 2425, 2426, 2443, 2461, 2462, 2464, 2465, 2466, 2470, 2471, 2474, 2477, 2489, 2491, 2494, 2497, 2507, 2526, 2527, 2528, 2529, 2530, 2531, 2532, 2533, 2535, 2536, 2537, 2538, 2540, 2541, 2543, 2546, 2549, 2684, 2688, 2695, 2696, 2697, 2698, 2704, 2705, 2706, 2707, 2708, 2710, 2711, 2713, 2720, 2722, 2725, 2726, 2730, 2741, 2742, 2744, 2746, 2747, 2748, 2751, 2754, 2756, 2761, 2765, 2766, 2767, 2768, 2769, 2770, 2771, 2772, 2773, 2774, 2775, 2776, 2779, 2799, 2822, 2855, 2856, 2859, 2860, 2863, 2864, 2865, 2867, 2882, 2886, 2891, 2906, 2907, 2908, 2909, 2911, 2912, 2918, 2966, 2976, 2978, 2980, 2981, 2987, 2988, 2990, 2991, 3001, 3002, 3003, 3005, 3007, 3008, 3009, 3011, 3012, 3015, 3016, 3017, 3018, 3019, 3020, 3025, 3026, 3029, 3035, 3036, 3038, 3102, 3103, 3106, 3107, 3113, 3130, 3139, 3164, 3169, 3192, 3197, 3201, 3202, 3203, 3204, 3205, 3206, 3232, 3259, 3261, 3267, 3268, 3269, 3270, 3271, 3272, 3283, 3284, 3302, 3331, 3341, 3342, 3343, 3347, 3348, 3373, 3377, 3392, 3410, 3415, 3417, 3418, 3419, 3424, 3425, 3426, 3434, 3435, 3443, 3451, 3452, 3455, 3456, 3457, 3458, 3459, 3460, 3464, 3465, 3467, 3468, 3471, 3547, 3553, 3555, 3556, 3557, 3576, 3594, 3595, 3596, 3599, 3601, 3602, 3603, 3605, 3608, 3609, 3633, 3634, 3638, 3641, 3642, 3652, 3653, 3654, 3655, 3656, or 3657.

178. The use of any one of embodiments 157-177, wherein the sense strand comprises the nucleoside sequence of any one of SEQ ID NOs: 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, or 1787; and wherein the antisense strand comprises the nucleoside sequence of any one of SEQ ID NOs: 1887, 1888, 1889, 1890, 1910, 1975, 2126, 2134, 2136, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2335, 2338, 2363, 2371, 2373, 2374, 2419, 2474, 2489, 2491, 2494, 2684, 2688, 2695, 2696, 2697, 2698, 2704, 2725, 2726, 2730, 2741, 2742, 2748, 2751, 2756, 2799, 2855, 2856, 2859, 2891, 2987, 2988, 2991, 3003, 3005, 3007, 3008, 3009, 3011, 3012, 3015, 3016, 3018, 3019, 3020, 3025, 3026, 3102, 3103, 3169, 3192, 3197, 3201, 3202, 3283, 3284, 3424, 3425, 3426, 3464, 3465, 3471, 3634, 3638, or 3641.

179. The use of any one of embodiments 157-178, wherein the sense strand comprises the nucleoside sequence of any one of SEQ ID NOs: 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, or 1803; and wherein the antisense strand comprises the nucleoside sequence of any one of SEQ ID NOs: 1886, 1887, 1888, 1889, 1890, 1910, 1911, 1912, 1913, 1915, 1916, 1917, 1918, 1933, 1934, 1966, 1970, 1971, 1972, 1973, 1974, 1979, 1980, 1981, 1982, 1983, 2003, 2004, 2006, 2007, 2011, 2012, 2013, 2015, 2018, 2019, 2020, 2021, 2022, 2023, 2026, 2028, 2029, 2050, 2053, 2065, 2066, 2068, 2069, 2070, 2071, 2072, 2073, 2075, 2076, 2077, 2082, 2084, 2085, 2094, 2095, 2099, 2100, 2104, 2106, 2107, 2108, 2109, 2114, 2115, 2116, 2117, 2119, 2120, 2125, 2126, 2128, 2134, 2143, 2144, 2145, 2146, 2147, 2153, 2158, 2175, 2177, 2179, 2180, 2182, 2183, 2184, 2185, 2186, 2187, 2188, 2189, 2191, 2192, 2193, 2196, 2201, 2203, 2204, 2206, 2207, 2210, 2234, 2236, 2240, 2242, 2245, 2246, 2247, 2248, 2251, 2252, 2253, 2256, 2258, 2259, 2265, 2266, 2267, 2268, 2269, 2274, 2275, 2276, 2277, 2278, 2279, 2280, 2281, 2282, 2283, 2284, 2285, 2289, 2338, 2371, 2373, 2374, 2419, 2424, 2425, 2426, 2461, 2462, 2464, 2465, 2466, 2470, 2471, 2474, 2489, 2491, 2494, 2526, 2527, 2528, 2529, 2530, 2531, 2532, 2533, 2535, 2536, 2537, 2538, 2540, 2541, 2543, 2546, 2549, 2684, 2695, 2696, 2697, 2698, 2704, 2705, 2706, 2707, 2708, 2710, 2711, 2720, 2722, 2725, 2726, 2730, 2741, 2742, 2744, 2746, 2747, 2748, 2756, 2765, 2766, 2767, 2768, 2769, 2770, 2771, 2772, 2773, 2774, 2775, 2776, 2799, 2855, 2856, 2859, 2860, 2863, 2864, 2865, 2867, 2882, 2886, 2906, 2907, 2908, 2909, 2911, 2912, 2966, 2976, 2978, 2980, 2981, 2987, 2988, 3001, 3002, 3003, 3005, 3007, 3008, 3009, 3011, 3012, 3015, 3016, 3018, 3019, 3020, 3029, 3036, 3038, 3106, 3107, 3113, 3130, 3139, 3164, 3169, 3197, 3201, 3202, 3203, 3204, 3205, 3259, 3261, 3267, 3268, 3269, 3270, 3271, 3272, 3283, 3284, 3302, 3373, 3377, 3410, 3415, 3417, 3418, 3419, 3425, 3426, 3434, 3435, 3443, 3451, 3455, 3456, 3457, 3458, 3459, 3460, 3465, 3467, 3468, 3547, 3553, 3555, 3556, 3557, 3576, 3594, 3595, 3596, 3599, 3601, 3602, 3603, 3605, 3608, 3609, 3633, 3634, 3638, 3642, 3652, 3653, 3655, 3656, or 3657.

180. The use of any one of embodiments 157-179, wherein the sense strand comprises the nucleoside sequence of any one of SEQ ID NOs: 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, or 1784; and wherein the antisense strand comprises the nucleoside sequence of any one of SEQ ID NOs: 1887, 1888, 1889, 1890, 1910, 2126, 2134, 2143, 2144, 2145, 2146, 2147, 2175, 2177, 2180, 2182, 2183, 2184, 2185, 2186, 2187, 2188, 2189, 2191, 2192, 2193, 2196, 2201, 2203, 2265, 2266, 2284, 2285, 2289, 2338, 2371, 2373, 2374, 2419, 2474, 2489, 2491, 2494, 2684, 2695, 2696, 2697, 2698, 2704, 2725, 2726, 2730, 2741, 2742, 2748, 2756, 2799, 2855, 2856, 2859, 2987, 2988, 3003, 3005, 3007, 3008, 3009, 3011, 3012, 3015, 3016, 3018, 3019, 3020, 3169, 3197, 3201, 3202, 3283, 3284, 3425, 3426, 3465, 3634, or 3638.

181. The use of any one of embodiments 157-180, wherein the antisense strand comprises a seed region that is not identical to a seed region of a human miRNA.

182. The use of any one of embodiments 157-181, wherein the sense strand comprises the nucleoside sequence of any one of SEQ ID NOs: 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, or 1803, or 3638; and wherein the antisense strand comprises the nucleoside sequence of any one of SEQ ID NOs: 1886, 1890, 1910, 1911, 1912, 1915, 1916, 1933, 1934, 1971, 1973, 1979, 1980, 1982, 2003, 2006, 2011, 2012, 2013, 2015, 2019, 2020, 2021, 2022, 2023, 2028, 2050, 2065, 2066, 2071, 2072, 2073, 2084, 2085, 2099, 2100, 2107, 2114, 2115, 2116, 2125, 2126, 2134, 2143, 2145, 2146, 2147, 2158, 2175, 2177, 2179, 2180, 2182, 2184, 2185, 2186, 2187, 2188, 2191, 2192, 2196, 2201, 2203, 2206, 2207, 2210, 2234, 2236, 2240, 2242, 2245, 2246, 2248, 2253, 2267, 2268, 2269, 2276, 2277, 2278, 2279, 2280, 2289, 2371, 2373, 2374, 2419, 2425, 2461, 2462, 2466, 2471, 2474, 2489, 2494, 2526, 2527, 2528, 2529, 2532, 2533, 2535, 2537, 2538, 2541, 2546, 2696, 2697, 2704, 2705, 2708, 2720, 2722, 2730, 2746, 2747, 2756, 2765, 2766, 2767, 2768, 2770, 2773, 2799, 2855, 2856, 2860, 2864, 2882, 2906, 2907, 2908, 2909, 2911, 2966, 2978, 2981, 3001, 3003, 3005, 3007, 3009, 3011, 3018, 3029, 3036, 3038, 3113, 3130, 3139, 3169, 3197, 3203, 3204, 3205, 3259, 3261, 3267, 3269, 3272, 3418, 3425, 3435, 3443, 3451, 3455, 3456, 3457, 3458, 3459, 3460, 3467, 3468, 3547, 3555, 3576, 3594, 3599, 3605, 3609, 3655, 3656, or 3657.

183. The use of any one of embodiments 157-182, wherein the sense strand comprises the nucleoside sequence of any one of SEQ ID 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, or 1571; and wherein the antisense strand comprises the nucleoside sequence of any one of SEQ ID 1890, 1910, 2126, 2134, 2143, 2145, 2146, 2147, 2175, 2177, 2180, 2182, 2184, 2185, 2186, 2187, 2188, 2191, 2192, 2196, 2201, 2203, 2289, 2371, 2373, 2374, 2419, 2474, 2489, 2494, 2696, 2697, 2704, 2730, 2756, 2799, 2855, 2856, 3003, 3005, 3007, 3009, 3011, 3018, 3169, 3197, or 3425.

184. The use of any one of embodiments 157-183, wherein the sense strand comprises a seed region that is not identical to a seed region of a human miRNA.

185. The use of any one of embodiments 157-184, wherein the sense strand comprises the nucleoside sequence of any one of SEQ ID NOs: 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, or 1787; and wherein the antisense strand comprises the nucleoside sequence of any one of SEQ ID NOs: 1886, 1890, 1910, 1912, 1915, 1916, 1934, 1971, 1973, 1980, 2006, 2008, 2011, 2012, 2013, 2015, 2020, 2023, 2028, 2031, 2050, 2065, 2066, 2071, 2072, 2084, 2085, 2099, 2107, 2114, 2115, 2125, 2126, 2134, 2143, 2147, 2158, 2182, 2184, 2185, 2186, 2187, 2188, 2191, 2196, 2201, 2203, 2207, 2210, 2240, 2242, 2245, 2246, 2248, 2268, 2269, 2276, 2277, 2278, 2280, 2289, 2374, 2425, 2462, 2466, 2471, 2507, 2526, 2532, 2533, 2535, 2537, 2546, 2696, 2697, 2705, 2708, 2713, 2730, 2746, 2754, 2767, 2768, 2773, 2822, 2855, 2856, 2908, 2911, 2918, 2966, 2978, 3011, 3018, 3036, 3038, 3102, 3113, 3197, 3205, 3206, 3269, 3272, 3418, 3435, 3456, 3468, 3547, 3555, 3576, 3594, 3605, 3609, or 3641.

186. The use of any one of embodiments 157-185, wherein the sense strand comprises the nucleoside sequence of any one of SEQ ID NOs: 36, 56, 272, 280, 289, 293, 328, 330, 331, 332, 333, 334, 337, 342, 347, 349, 435, 520, 842, 843, 876, 1001, 1002, 1157, 1164, or 1343; and wherein the antisense strand comprises the nucleoside sequence of any one of SEQ ID NOs: 1890, 1910, 2126, 2134, 2143, 2147, 2182, 2184, 2185, 2186, 2187, 2188, 2191, 2196, 2201, 2203, 2289, 2374, 2696, 2697, 2730, 2855, 2856, 3011, 3018, or 3197.

187. The use of any one of embodiments 157-186, wherein the sense strand comprises modification pattern 1S: 5'-NfsnsNfnNfnNfNfNfnNfnNfnNfnNfnNfnNfsnsn-3', wherein "Nf" is a 2' fluoro-modified nucleoside, "n" is a 2' O-methyl modified nucleoside, and "s" is a phosphorothioate linkage.

188. The use of any one of embodiments 157-186, wherein the sense strand comprises modification pattern 2S: 5'-nsnsnnNfnNfNfNfnnnnnnnnnnsnsn-3', wherein "Nf" is a 2' fluoro-modified nucleoside, "n" is a 2' O-methyl modified nucleoside, and "s" is a phosphorothioate linkage.

189. The use of any one of embodiments 157-186, wherein the sense strand comprises modification pattern 3S: 5'-nsnsnnNfnNfnNfnnnnnnnnnnsnsn-3', wherein "Nf" is a 2' fluoro-modified nucleoside, "n" is a 2' O-methyl modified nucleoside, and "s" is a phosphorothioate linkage.

190. The use of any one of embodiments 157-186, wherein the sense strand comprises modification pattern 4S: 5'-NfsnsNfnNfnNfNfNfnNfnNfnNfnNfnNfsnsnN-3', wherein "Nf" is a 2' fluoro-modified nucleoside, "n" is a 2' O-methyl modified nucleoside, "s" is a phosphorothioate linkage, and N comprises one or more nucleosides.

191. The use of any one of embodiments 157-186, wherein the sense strand comprises modification pattern 5S: 5'-nsnsnnNfnNfNfNfnnnnnnnnnnsnsnN-3', wherein "Nf" is a 2' fluoro-modified nucleoside, "n" is a 2' O-methyl modified nucleoside, "s" is a phosphorothioate linkage, and N comprises one or more nucleosides.

192. The use of any one of embodiments 157-192, wherein the antisense strand comprises modification pattern 1AS: 5'-nsNfsnNfnNfnNfnNfnnnNfnNfnNfsnsn-3', wherein "Nf" is a 2' fluoro-modified nucleoside, "n" is a 2' O-methyl modified nucleoside, and "s" is a phosphorothioate linkage.

193. The use of any one of embodiments 157-192, wherein the antisense strand comprises modification pattern 2AS: 5'-nsNfsnnnNfnNfNfnnnnNfnNfnnnsnsn-3', wherein "Nf" is a 2' fluoro-modified nucleoside, "n" is a 2' O-methyl modified nucleoside, and "s" is a phosphorothioate linkage.

194. The use of any one of embodiments 157-192, wherein the antisense strand comprises modification pattern 3AS: 5'-nsNfsnnnNfnnnnnnnnNfnNfnnnsnsn-3', wherein "Nf" is a 2' fluoro-modified nucleoside, "n" is a 2' O-methyl modified nucleoside, and "s" is a phosphorothioate linkage.

195. The use of any one of embodiments 157-192, wherein the antisense strand comprises modification pattern 4AS: 5'-nsNfsnNfnNfnnnnnnnnNfnNfnnnsnsn-3', wherein "Nf" is a 2' fluoro-modified nucleoside, "n" is a 2' O-methyl modified nucleoside, and "s" is a phosphorothioate linkage.

196. The use of any one of embodiments 157-186, wherein the sense strand comprises modification pattern 1S and the antisense strand comprises modification pattern 1AS, 2AS, 3AS, or 4AS.

197. The use of any one of embodiments 157-186, wherein the sense strand comprises modification pattern 2S and the antisense strand comprises modification pattern 1AS, 2AS, 3AS, or 4AS.

198. The use of any one of embodiments 157-186, wherein the sense strand comprises modification pattern 3S and the antisense strand comprises modification pattern 1AS, 2AS, 3AS, or 4AS.

199. The use of any one of embodiments 157-186, wherein the sense strand comprises modification pattern 4S and the antisense strand comprises modification pattern 1AS, 2AS, 3AS, or 4AS.

200. The use of any one of embodiments 157-186, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 1S.

201. The use of any one of embodiments 157-186, wherein the sense strand comprises a nucleoside sequence comprising or consisting of the sequence of any one of SEQ ID NOs: 1-1854 or 13970-13977, and modification pattern 1S.

202. The use of any one of embodiments 157-186, wherein the sense strand comprises a nucleoside sequence comprising or consisting of the sequence of any one of SEQ ID NOs: 1-1854 or 13970-13977, or a nucleic acid sequence thereof having 1 or 2 nucleoside substitutions, additions, or deletions, and modification pattern 2S.

203. The use of any one of embodiments 157-186, wherein the sense strand comprises a nucleoside sequence comprising or consisting of the sequence of any one of SEQ ID NOs: 1-1854 or 13970-13977, and modification pattern 2S.

204. The use of any one of embodiments 157-186 or 200-203, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 1AS.

205. The use of any one of embodiments 157-186 or 200-203, wherein the antisense strand comprises a nucleoside sequence comprising or consisting of the sequence of any one of SEQ ID NOs: 1855-3708 or 13978-13985, and modification pattern 1AS.

206. The use of any one of embodiments 157-186 or 200-203, wherein the antisense strand comprises a nucleoside sequence comprising or consisting of the sequence of any one of SEQ ID NOs: 1855-3708 or 13978-13985, or a nucleic acid sequence thereof having 1 or 2 nucleoside substitutions, additions, or deletions, and modification pattern 3AS.

207. The use of any one of embodiments 157-186 or 200-203, wherein the antisense strand comprises a nucleoside sequence comprising or consisting of the sequence of any one of SEQ ID NOs: 1855-3708 or 13978-13985, and modification pattern 3AS.

208. The use of any one of embodiments 90-156, wherein the oligonucleotide comprises an ASO.

209. The use of embodiment 208, wherein the ASO is 12-30 nucleosides in length. 210. The use of any one of embodiments 90-156, wherein the oligonucleotide comprises an antisense oligonucleotide (ASO) about 12-30 nucleosides in length and comprising a nucleoside sequence complementary to about 12-30 contiguous nucleosides of SEQ ID NO: 13935.

211. The use of any one of embodiments 90-156, wherein the oligonucleotide comprises an ASO about 12-30 nucleosides in length and comprising a nucleoside sequence complementary to about 12-30 contiguous nucleosides of SEQ ID NO: 13936.

212. The use of any one of embodiments 208-211, wherein the ASO is 15-25 nucleosides in length.

213. The use of any one of embodiments 208-212, wherein the ASO is 20 nucleosides in length.

214. The use of any one of embodiments 208-213, wherein the ASO comprises a nucleoside sequence comprising or consisting of the sequence of any one of SEQ ID NOs: 3709-13934, or a nucleic acid sequence thereof having 1 or 2 nucleoside substitutions, additions, or deletions.

215. The use of any one of embodiments 208-214, wherein the ASO comprises a nucleoside sequence comprising or consisting of the sequence of any one of SEQ ID NOs: 3709-13934.

216. The use of any one of embodiments 208-215, wherein the ASO comprises modification pattern: 5'-nsnsnsnsnsdNsdNsdNsdNsdNsdNsdNsdNsdNsnsns-nsnsn-3' where "dN" is any deoxynucleotide, "n" is a 2'O-methyl or 2'O-methoxyethyl-modified nucleoside, and "s" is a phosphorothioate linkage.

217. The use of any one of embodiments 208-215, wherein the ASO comprises a nucleoside sequence comprising or consisting of the sequence of any one of SEQ ID NOs: 3709-13934, or a nucleic acid sequence thereof having 1 or 2 nucleoside substitutions, additions, or deletions, and modification pattern ASO1.

218. The use of any one of embodiments 208-215, wherein the ASO comprises a nucleoside sequence comprising or consisting of the sequence of any one of SEQ ID NOs: 3709-13934, and modification pattern ASO1.

219. The use of any one of embodiments 90-218, wherein the composition is a pharmaceutical composition.

220. The use of any one of embodiments 90-219, wherein the composition is sterile. 221. The use of any one of embodiments 90-220, further comprising a pharmaceutically acceptable carrier.

222. The use of embodiment 221, wherein the pharmaceutically acceptable carrier comprises water, a buffer, or a saline solution.

223. The composition of any one of embodiments 28-57, wherein the sense strand comprises modification pattern 6S.

224. The composition of any one of embodiments 28-62 or 223, wherein the antisense strand comprises modification pattern 5AS.

225. The composition of any one of embodiments 28-62 or 223, wherein the antisense strand comprises modification pattern 6AS.

226. The composition of any one of embodiments 28-62 or 223, wherein the antisense strand comprises modification pattern 7AS.

227. The composition of any one of embodiments 28-62 or 223, wherein the antisense strand comprises modification pattern 8AS.

228. The composition of any one of embodiments 28-62 or 223, wherein the antisense strand comprises modification pattern 9AS.

229. The use of any one of embodiments 157-186, wherein the sense strand comprises modification pattern 6S.

230. The use of any one of embodiments 157-192 or 229, wherein the antisense strand comprises modification pattern 5AS.

231. The use of any one of embodiments 157-192 or 229, wherein the antisense strand comprises modification pattern 6AS.

232. The use of any one of embodiments 157-192 or 229, wherein the antisense strand comprises modification pattern 7AS.

233. The use of any one of embodiments 157-192 or 229, wherein the antisense strand comprises modification pattern 8AS.

234. The use of any one of embodiments 157-192 or 229, wherein the antisense strand comprises modification pattern 9AS.

VI. Further Embodiments

Some embodiments include one or more of the following:

1. A composition comprising an oligonucleotide that targets Angiopoietin-like 4 (ANGPTL4) and when administered to a subject in an effective amount decreases circulating triglycerides, decreases circulating total cholesterol, decreases circulating glucose, increases circulating high-density lipoproteins (HDL), or increases insulin sensitivity, wherein the oligonucleotide comprises a small interfering RNA (siRNA) comprising a sense strand and an antisense strand, the antisense strand being complementary with no more than 2 mismatches to a portion of a nucleic acid having the nucleoside sequence of SEQ ID NO: 13936, and each strand having 12 to 30 nucleotides.

2. The composition of embodiment 1, wherein the triglycerides, total cholesterol, or glucose is decreased by about 10% or more, or the HDL or insulin sensitivity is increased by about 10% or more, as compared to prior to administration.

3. The composition of embodiment 1 or 2, wherein the antisense strand is complementary with no more than 2 mismatches to a portion of a nucleic acid having the nucleoside sequence of SEQ ID NO: 13935.

4. The composition of any one of embodiments 1-3, wherein the antisense strand comprises a nucleoside sequence at least 85% identical to any antisense strand sequence of an siRNA in Table 4.

5. The composition of any one of embodiments 1-3, wherein the antisense strand comprises the nucleoside sequence of any antisense strand sequence of an siRNA in Table 4, or an antisense strand sequence thereof having 1 or 2 nucleoside substitutions, additions, or deletions.

6. The composition of any one of embodiments 1-3, wherein the antisense strand comprises the nucleoside sequence of any antisense strand sequence of an siRNA in Table 4.

7. The composition of any one of embodiments 4-6, wherein the sense strand comprises a nucleoside sequence at least 85% identical to the sense strand sequence of the siRNA in Table 4.

8. The composition of any one of embodiments 4-6, wherein the sense strand comprises the nucleoside sequence of the sense strand sequence of the siRNA in Table 4, or a sense strand sequence thereof having 1 or 2 nucleoside substitutions, additions, or deletions.

9. The composition of any one of embodiments 4-6, wherein the sense strand comprises the nucleoside sequence of the sense strand sequence of the siRNA in Table 4.

10. The composition of any one of embodiments 1-3, wherein the antisense strand comprises a nucleoside sequence at least 85% identical to any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696.

11. The composition of any one of embodiments 1-3, wherein the antisense strand comprises the nucleoside sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or an antisense strand sequence thereof having 1 or 2 nucleoside substitutions, additions, or deletions.

12. The composition of any one of embodiments 1-3, wherein the antisense strand comprises the nucleoside sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696.

13. The composition of any one of embodiments 10-12, wherein the sense strand comprises a nucleoside sequence at least 85% identical to any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842.

14. The composition of any one of embodiments 10-12, wherein the sense strand comprises the nucleoside sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, or a sense strand sequence thereof having 1 or 2 nucleoside substitutions, additions, or deletions.

15. The composition of any one of embodiments 10-12, wherein the sense strand comprises the nucleoside sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842.

16. The composition of any one of embodiments 1-3, wherein the antisense strand comprises a nucleoside sequence at least 85% identical to any one of SEQ ID NOS: 13978-13981.

17. The composition of any one of embodiments 1-3, wherein the antisense strand comprises the nucleoside sequence of any one of SEQ ID NOS: 13978-13981, or an antisense strand sequence thereof having 1 or 2 nucleoside substitutions, additions, or deletions.

18. The composition of any one of embodiments 1-3, wherein the antisense strand comprises the nucleoside sequence of any one of SEQ ID NOS: 13978-13981.

19. The composition of any one of embodiments 16-18, wherein the sense strand comprises a nucleoside sequence at least 85% identical to any one of SEQ ID NOS: 13970-13973.

20. The composition of any one of embodiments 16-18, wherein the sense strand comprises the nucleoside sequence of any one of SEQ ID NOS: 13970-13973, or a sense strand sequence thereof having 1 or 2 nucleoside substitutions, additions, or deletions.

21. The composition of any one of embodiments 16-18, wherein the sense strand comprises the nucleoside sequence of any one of SEQ ID NOS: 13970-13973.

22. The composition of any one of embodiments 1-21, wherein the oligonucleotide comprises one or more modified internucleoside linkages.

23. The composition of embodiment 22, wherein the one or more modified internucleoside linkages comprise alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

24. The composition of embodiment 22 or 23, wherein the one or more modified internucleoside linkages comprise a phosphorothioate linkage.

25. The composition of any one of embodiments 22-24, wherein the sense strand comprises 2-6 modified internucleoside linkages.

26. The composition of any one of embodiments 22-25, wherein the antisense strand comprises 2-6 modified internucleoside linkages.

27. The composition of any one of embodiments 1-26, wherein the oligonucleotide comprises one or more modified nucleosides.

28. The composition of embodiment 27, wherein the one or more modified nucleosides comprise a locked nucleic acid (LNA), hexitol nucleic acid (HLA), cyclohexene nucleic acid (CeNA), a 2',4' constrained ethyl, 2'-methoxyethyl, 2'-O-alkyl, 2'-O-allyl, 2'-O-allyl, 2'-fluoro, 2'-deoxy, a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, 2'-ara-F, or a combination thereof.

29. The composition of embodiment 27 or 28, wherein the one or more modified nucleosides comprise a 2' fluoro modified nucleoside.

30. The composition of any one of embodiments 27-29, wherein the one or more modified nucleosides comprise a 2' O-methyl modified nucleoside.

31. The composition of any one of embodiments 27-30, wherein the sense strand comprises 15-21 modified nucleosides, and/or the antisense strand comprises 15-21 modified nucleosides.

32. The composition of any one of embodiments 1-31, wherein the sense strand or the antisense strand comprises a 3' overhang of at least 2 nucleosides.

33. The composition of any one of embodiments 1-32, wherein the oligonucleotide comprises a GalNAc ligand attached at a 3' or 5' terminus of the sense strand.

34. The composition of any one of embodiments 1-33, wherein the oligonucleotide comprises a GalNAc ligand attached at a 3' or 5' terminus of the antisense strand 35. The composition of any one of embodiments 1-34, wherein the sense strand comprises modification pattern 1S: 5'-NfsnsNfnNfnNfNfNfnNfnNfnNfnNfnNfsnsn-3' (SEQ ID NO: 13954), modification pattern 2S: 5'-nsnsnnNfnNfNf Nfnnnnnnnnnnsnsn-3' (SEQ ID NO: 13955), modification pattern 3S: 5'-nsnsnnNfnNfnNfnnnnnnnnnnsnsn-3' (SEQ ID NO: 13956), modification pattern 4S: 5'-NfsnsNfnNfnNfnNfnNfnNfnNfnNfnNfnNfnNfnNfsnsn-3' (SEQ ID NfnNfnNfnNfnNfnNfsnsnN-3'(SEQIDNO:13957), modification pattern 5S: 5'-nsnsnnNfnNfNfNfnnnn nnnnnnsnsnN-3' (SEQ ID NO: 13958); modification pattern 6S: 5'-NfsnsNfnNfnNfnNfnNfnNfnNfnNfnNfsnsn-3' (SEQ ID NO: 13959); wherein "Nf" is a 2' fluoro-modified nucleoside, "n" is a 2' O-methyl modified nucleoside, "s" is a phosphorothioate linkage, and N comprises a nucleoside.

36. The composition of any one of embodiments 1-35, wherein the antisense strand comprises modification pattern 1AS: 5'-nsNfsnNfnNfnNfnNfnnnNfnNfnNfsnsn-3' (SEQ ID NO: 13960), modification pattern 2AS: 5'-nsNfsnnnNfn NfNfnnnnNfnNfnnnsnsn-3' (SEQ ID NO: 13961), modification pattern 3AS: 5'-nsNfsnnnNfnnnnnnnNfnNfnnnsnsn-3' (SEQ ID NO: 13962), modification pattern 4AS: 5'-nsNf snNfnNfnnnnnnnNfnNfnnnsnsn-3' (SEQ ID NO: 13963), modification pattern 5AS: 5'-nsNfsnnnNfnNfnnnnn NfnNfnnnsnsn-3' (SEQ ID NO: 13964), modification pattern 6AS: 5'-nsNfsnNfnNfnNfnNfnNfnNfnNfnNfsnsn-3' (SEQ ID NO: 13965), modification pattern 7AS: 5'-nsNfsnNfnNfnNfNfnnnnNfnNfnnnsnsn-3' (SEQ ID NO: 13966), modification pattern 8AS: 5'-nsNfsnnnnnnnnnnn Nfnnnnnsnsn-3' (SEQ ID NO: 13967), or modification pattern 9AS: 5'-nsNfsnnnNfnnnnnnnNfnNfnNfnsnsn-3' (SEQ ID NO: 13968); wherein "Nf" is a 2' fluoro-modified nucleoside, "n" is a 2' O-methyl modified nucleoside, and "s" is a phosphorothioate linkage.

37. The composition of any one of embodiments 1-36, wherein the composition is a pharmaceutical composition comprising a pharmaceutically acceptable carrier.

38. The composition of embodiment 37, wherein the pharmaceutically acceptable carrier comprises water, a buffer, or a saline solution.

39. Use of a composition comprising an oligonucleotide that targets ANGPTL4, wherein the oligonucleotide comprises a small interfering RNA (siRNA) comprising a sense strand and an antisense strand, the antisense strand being complementary with no more than 2 mismatches to a portion of a nucleic acid having the nucleoside sequence of SEQ ID NO: 13936, and each strand having 12 to 30 nucleotides, in a method of treating a metabolic or cardiovascular disorder in a subject in need thereof, the method comprising administering to the subject an effective amount of the composition.

40. The use of embodiment 39, wherein the disorder comprises hyperlipidemia, hypertriglyceridemia, diabetes, type 2 diabetes, heart disease, a myocardial infarction, angina pectoris, or atherosclerosis.

41. The use of embodiment 39 or 40, wherein the effective amount of the composition decreases a triglyceride measurement, decreases a cholesterol measurement, decreases a glucose measurement, increases an HDL measurement, or increases an insulin sensitivity measurement in the subject by about 10% or more, relative to a baseline measurement.

42. The use of any one of embodiments 39-41, wherein the antisense strand is complementary with no more than 2 mismatches to a portion of a nucleic acid having the nucleoside sequence of SEQ ID NO: 13935.

43. The use of any one of embodiments 39-42, wherein the antisense strand comprises a nucleoside sequence at least 85% identical to any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696.

44. The use of any one of embodiments 39-42, wherein the antisense strand comprises the nucleoside sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696, or an antisense strand sequence thereof having 1 or 2 nucleoside substitutions, additions, or deletions.

45. The use of any one of embodiments 39-42, wherein the antisense strand comprises the nucleoside sequence of any one of SEQ ID NOS: 1886, 1887, 1889, 1890, 1975, 2134, 2136, 2143, 2144, 2146, 2175, 2177, 2180, 2186, 2188, 2338, 2363, 2373, 2419, 2424, 2425, 2474, 2491, 2494, 2613, 2688, 2730, 2855, 2987, 2988, 2991, 3003, 3005, 3008, 3011, 3019, 3020, 3025, 3026, 3102, 3103, 3139, 3192, 3202, 3284, 3343, 3344, 3418, 3434, 3435, 3443, 3451, 3465, 3556, 3694, or 3696.

46. The use of any one of embodiments 43-45, wherein the sense strand comprises a nucleoside sequence at least 85% identical to any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842.

47. The use of any one of embodiments 43-45, wherein the sense strand comprises the nucleoside sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842, ora sense strand sequence thereof having 1 or 2 nucleoside substitutions, additions, or deletions.

48. The use of any one of embodiments 43-45, wherein the sense strand comprises the nucleoside sequence of any one of SEQ ID NOS: 32, 33, 35, 36, 121, 280, 282, 289, 290, 292, 321, 323, 326, 332, 334, 484, 509, 519, 565, 570, 571, 620, 637, 640, 759, 834, 876, 1001, 1133, 1134, 1137, 1149, 1151, 1154, 1157, 1165, 1166, 1171, 1172, 1248, 1249, 1285, 1338, 1348, 1430, 1489, 1490, 1564, 1580, 1581, 1589, 1597, 1611, 1702, 1840, or 1842.

49. The use of any one of embodiments 39-42, wherein the antisense strand comprises a nucleoside sequence at least 85% identical to any one of SEQ ID NOS: 13978-13981.

50. The use of any one of embodiments 39-42, wherein the antisense strand comprises the nucleoside sequence of any one of SEQ ID NOS: 13978-13981, or an antisense strand sequence thereof having 1 or 2 nucleoside substitutions, additions, or deletions.

51. The use of any one of embodiments 39-42, wherein the antisense strand comprises the nucleoside sequence of any one of SEQ ID NOS: 13978-13981.

52. The use of any one of embodiments 49-51, wherein the sense strand comprises a nucleoside sequence at least 85% identical to any one of SEQ ID NOS: 13970-13973.

53. The use of any one of embodiments 49-51, wherein the sense strand comprises the nucleoside sequence of any one of SEQ ID NOS: 13970-13973, or a sense strand sequence thereof having 1 or 2 nucleoside substitutions, additions, or deletions.

54. The use of any one of embodiments 49-51, wherein the sense strand comprises the nucleoside sequence of any one of SEQ ID NOS: 13970-13973.

55. The use of any one of embodiments 39-54, wherein the oligonucleotide comprises one or more modified internucleoside linkages comprising alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

56. The use of any one of embodiments 39-55, wherein the oligonucleotide comprises one or more modified nucleosides comprising a locked nucleic acid (LNA), hexitol nucleic acid (HLA), cyclohexene nucleic acid (CeNA), a 2',4' constrained ethyl, 2'-methoxyethyl, 2'-O-alkyl, 2'-O-allyl, 2'-O-allyl, 2'-fluoro, 2'-deoxy, a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, 2'-ara-F, or a combination thereof.

57. The use of any one of embodiments 39-56, wherein the sense strand or the antisense strand comprises a 3' overhang of at least 2 nucleosides.

58. The use of any one of embodiments 39-57, wherein the oligonucleotide comprises a GalNAc ligand attached at a 3' or 5' terminus of the sense strand.

59. The use of any one of embodiments 39-58, wherein the oligonucleotide comprises a GalNAc ligand attached at a 3' or 5' terminus of the antisense strand 60. The use of any one of embodiments 39-59, wherein the sense strand comprises modification pattern 1S: 5'-NfsnsNfnNfnNfNfNfnNfnNfnNfnNfnNfsnsn-3' (SEQ ID NO: 13954), modification pattern 2S: 5'-nsnsnnNfnNfNf Nfnnnnnnnnnnnsnsn-3' (SEQ ID NO: 13955), modification pattern 3S: 5'-nsnsnnNfnNfnNfnnnnnnnnnnnsnsn-3' (SEQ ID NO: 13956), modification pattern 4S: 5'-NfsnsNfnNfnNf NfNfnNfnNfnNfnNfnNfsnsnN-3' (SEQ ID NO: 13957), modification pattern 5S: 5'-nsnsnnNfnNfNf Nfnnnnnnnnnnnsnsn N-3' (SEQ ID NO: 13958); modification pattern 6S: 5'-NfsnsNfnNfnNfnNfnNfnNfnNfnNfnNfnNfsnsn-3' (SEQ ID NO: 13959); wherein "Nf" is a 2' fluoro-modified nucleoside, "n" is a 2' O-methyl modified nucleoside, "s" is a phosphorothioate linkage, and N comprises a nucleoside.

61. The use of any one of embodiments 39-60, wherein the antisense strand comprises modification pattern 1AS: 5'-nsNfsnNfnNfnNfnNfnnnNfnNfnNfnsnsn-3' (SEQ ID NO: 13960), modification pattern 2AS: 5'-nsNfsnnnNfnNf NfnrmnNfnNfnnnsnsn-3' (SEQ ID NO: 13961), modification pattern 3AS: 5'-nsNfsnnnNfnrmrmnnNfnNfrmnsnsn-3' (SEQ ID NO: 13962), modification pattern 4AS: 5'-nsNfsn NfnNfnnrmrmnNfnNfnnnsnsn-3' (SEQ ID NO: 13963), modification pattern 5AS: 5'-nsNfsnnnNfnNfrmrmnNfn Nfnnnsnsn-3' (SEQ ID NO: 13964), modification pattern 6AS: 5'-nsNfsnNfnNfnNfnNfnNfnNfnNfnNfnsnsn-3' (SEQ ID NO: 13965), modification pattern 7AS: 5'-nsNfsnNfn NfnNfNfnnnnNfnNfnnnsnsn-3' (SEQ ID NO: 13966), modification pattern 8AS: 5'-nsNfsnnnnnnnnnnNf nnnnnsnsn-3' (SEQ ID NO: 13967), or modification pattern 9AS: 5'-nsNfsnnnNfnnnnnnnNfnNfnNfnsnsn-3' (SEQ ID NO: 13968); wherein "Nf" is a 2' fluoro-modified nucleoside, "n" is a 2' O-methyl modified nucleoside, and "s" is a phosphorothioate linkage.

VII. Examples

The following examples are included for illustrative purposes only and are not intended to limit the scope of the invention.

Example 1: Loss of Function Variants in ANGPTL4 Are Associated with Decreased Risk of Cardiovascular and Metabolic Disease Approximately 30,000,000 imputed variants were analyzed in 375,000 individuals from the UK Biobank cohort for associations with cardiometabolic traits including circulating triglyceride levels, hyperlipidemia, chronic ischemic heart disease, myocardial infarction, Type 2 diabetes, and lipid-lowering and diabetes medication use. Additionally, rare loss of function variants were evaluated in a gene burden test in a subset of 45,000 individuals from the UK Biobank cohort with available exome sequencing data. Case counts in the full and exome-sequenced cohorts are shown in Table 2.

TABLE 2

Case and Value Counts for Tested Cardiometabolic Traits

| Trait | Imputed Genotypes Cases/Counts | Exome Sequencing Cases/Counts |
|---|---|---|
| Hyperlipidemia | 80,196 | 10,112 |
| Chronic ischemic heart disease | 26,771 | 3,135 |
| Angina pectoris | 22,200 | 2,685 |
| Myocardial Infarction | 15,250 | 1,616 |
| Type 2 diabetes mellitus | 20,663 | 2,512 |
| Medication-simvastatin | 42,197 | 5,404 |
| Medication-metformin | 9,262 | 1,184 |
| Family history of heart disease | 162,657 | 20,211 |
| Family history of diabetes | 76,202 | 9,845 |
| Blood Triglycerides | 356,875 | 43,055 |
| Blood HDL | 327,461 | 40,600 |

Protective associations were observed between a low-frequency and a rare missense variant (rs116843064; MAF=0.02 and rs140744493; MAF=0.003) within ANGPTL4 and cardiometabolic traits (see Table 3). The major allele (chr19-8429323-G, hg19) of the rs116843064 variant encodes for a glutamic acid residue and the minor allele (chr19-8429323-A, hg19) a lysine at amino acid position 40 of the full length ANGPTL4 protein (Glu40Lys; E40K). A lysine at position 40 reduces the inhibition of LPL by ANGPTL4; rs116843064 is thus a loss of function variant. The major allele (chr19-8436373-C, hg19) of the rs140744493 variant encodes for an arginine residue and the minor allele (chr19-8436373-T, hg19) a cysteine at amino acid position 336 of the full length ANGPTL4 protein (Arg336Cys; R336C). A cysteine at position 336 impairs cellular secretion of ANGPTL4; rs140744493 is thus also a loss of function variant. Carriers of the minor allele of both of these variants had a reduced risk of a range of cardiometabolic diseases, as well as reduced circulating triglycerides ($p=2.35\times10^{-145}$; beta=−0.048 and $p=2.64\times10^{-4}$; beta=−0.018 for rs116843064 and rs140744493, respectively) and increased high density lipoprotein levels ($p=2.35\times10^{-145}$; beta=−0.048 and $p=2.64\times10^{-4}$; beta= −0.018 for rs116843064 and rs140744493, respectively). Accordingly, in some cases therapeutic inhibition or modulation of ANGPTL4 may be an effective genetically-informed method of treatment for cardiovascular and metabolic disease.

TABLE 3

Association of ANGPTL4 Missense Variants with Cardiometabolic Traits

| Trait | rs116843064 (E40K) | | rs140744493 (R336C) | |
|---|---|---|---|---|
| | Effect Size | P | Effect Size | P |
| Hyperlipidemia | 0.87 (OR) | 2.04E−10 | NS | NS |
| Chronic ischemic heart disease | 0.84 (OR) | 1.03E−06 | NS | NS |
| Angina pectoris | 0.85 (OR) | 1.59E−05 | 0.81 (OR) | 0.04 |
| Myocardial Infarction | 0.85 (OR) | 4.53E−04 | NS | NS |
| Type 2 diabetes mellitus | 0.88 (OR) | 7.31E−04 | NS | NS |
| Medication-simvastatin | 0.91 (OR) | 1.13E−03 | 0.83 (OR) | 0.01 |
| Medication-metformin | 0.79 (OR) | 9.11E−05 | NS | NS |
| Family history of heart disease | 0.95 (OR) | 5.55E−03 | 0.91 (OR) | 0.04 |
| Family history of diabetes | 0.94 (OR) | 2.20E−03 | NS | NS |
| Blood Triglycerides | −0.048 (beta) | 2.35E−145 | −0.018 (beta) | 2.13E−04 |
| Blood HDL | 0.023 (beta) | 3.15E−115 | 0.011 (beta) | 9.70E−06 |

NS = Not Significant,
OR = Odds Ratio

Using the subset of individuals with available exome sequencing data (approximately 45,000 of the 375,000 individuals), a gene burden test was applied to assess the association of ANGPTL4 loss of function variants on cardiometabolic traits. Gene burden tests are used to aggregate rare variants in a gene by functional class that are too rare to be tested individually. In total, 17 rare predicted loss of function variants (frameshift, stop gained and splice donor/acceptor variants) in 72 total carriers were tested. Individuals carrying predicted ANGPTL4 loss of function variants had significantly lower triglyceride levels when compared to non-carriers (p=2.64E-4; beta=−0.097). These results are directionally consistent with the results obtained in the larger cohort for the rs116843064 and rs140744493 inactivating missense variants, and further confirm that ANGPTL4 loss of function results in lower circulating triglyceride levels.

Example 2: Bioinformatic Selection of Sequences in Order to Identify Therapeutic siRNAs to Downmodulate Expression of the ANGPTL4 mRNA Screening sets were defined based on bioinformatic analysis. Therapeutic siRNAs were designed to target human ANGPTL4, and the ANGPTL4 sequence of at least one toxicology-relevant species, in this case, the non-human primates (NHP) rhesus and cynomolgus monkeys. Drivers for the design of the screening set were predicted specificity of the siRNAs against the transcriptome of the relevant species as well as cross-reactivity between species. Predicted specificity in human, rhesus monkey, cynomolgus monkey, mouse and rat was determined for sense (S) and antisense (AS) strands. These were assigned a "specificity score" which considers the likelihood of unintended downregulation of any other transcript by full or partial complementarity of an siRNA strand (up to 4 mismatches within positions 2-18) as well as the number and positions of mismatches. Thus, off-target(s) for antisense and sense strands of each siRNA were identified. In addition, the number of potential off-targets was used as an additional specificity factor in the specificity score. As identified, siRNAs with high specificity and a low number of predicted off-targets provide a benefit of increased targeting specificity.

In addition to selecting siRNA sequences with high sequence specificity to ANGPTL4 mRNA, siRNA sequences within the seed region were analyzed for similarity to seed regions of known miRNAs. siRNAs can function in a miRNA like manner via base-pairing with complementary sequences within the 3'-UTR of mRNA molecules. The complementarity typically encompasses the 5'-bases at positions 2-7 of the miRNA (seed region). To circumvent siRNAs to act via functional miRNA binding sites, siRNA strands containing natural miRNA seed regions were avoided. Seed regions identified in miRNAs from human, mouse, rat, rhesus monkey, dog, rabbit and pig are referred to as "conserved". Combining the "specificity score" with miRNA seed analysis yielded a "specificity category". This is divided into categories 1-4, with 1 having the highest specificity and 4 having the lowest specificity. Each strand of the siRNA is assigned to a specificity category.

Species cross-reactivity was assessed for human, cynomolgus monkey, rhesus monkey, mouse and rat. The analysis was based on a canonical siRNA design using 19 bases and 17 bases (without considering positions 1 and 19) for cross-reactivity. Full match as well as single mismatch analyses were included.

Analysis of the human Single Nucleotide Polymorphism (SNP) database (NCBI-DB-SNP) to identify siRNAs targeting regions with known SNPs was also carried out to identify siRNAs that may be non-functional in individuals containing the SNP. Information regarding the positions of SNPs within the target sequence as well as minor allele frequency (MAF) in case data was obtained in this analysis.

Initial analysis of the relevant ANGPTL4 mRNA sequence revealed few sequences that fulfil the specificity parameters and at the same time target ANGPTL4 mRNA in all of the analyzed relevant species. Therefore, it was decided to design independent screening subsets for the therapeutic siRNAs.

The siRNAs in these subsets recognize the human ANGPTL4 sequence, as a human cell culture system is selected for determination of in vitro activity. Therefore, the siRNAs in these subsets can be used to target human ANGPTL4 in a therapeutic setting.

The number of siRNAs that were derived from human ANGPTL4 mRNA (NM_139314.3) without consideration of specificity or species cross-reactivity was 1,854 (antisense and sense strand sequences included in SEQ ID NOS: 1-3708).

Prioritizing sequences for target specificity, species cross-reactivity, miRNA seed region sequences and SNPs as described above yields subset A. The siRNAs in subset A are included in Table 4.

TABLE 4

Subset A

| siRNA Name | Sense Strand Sequence- SEQ ID NO: | Antisense Strand Sequence- SEQ ID NO: |
|---|---|---|
| siRNA 32 | 32 | 1886 |
| siRNA 33 | 33 | 1887 |
| siRNA 34 | 34 | 1888 |
| siRNA 35 | 35 | 1889 |
| siRNA 36 | 36 | 1890 |
| siRNA 56 | 56 | 1910 |
| siRNA 57 | 57 | 1911 |
| siRNA 58 | 58 | 1912 |
| siRNA 59 | 59 | 1913 |
| siRNA 61 | 61 | 1915 |
| siRNA 62 | 62 | 1916 |
| siRNA 63 | 63 | 1917 |
| siRNA 64 | 64 | 1918 |
| siRNA 79 | 79 | 1933 |
| siRNA 80 | 80 | 1934 |
| siRNA 84 | 84 | 1938 |
| siRNA 111 | 111 | 1965 |
| siRNA 112 | 112 | 1966 |
| siRNA 116 | 116 | 1970 |
| siRNA 117 | 117 | 1971 |
| siRNA 118 | 118 | 1972 |
| siRNA 119 | 119 | 1973 |
| siRNA 120 | 120 | 1974 |
| siRNA 121 | 121 | 1975 |
| siRNA 125 | 125 | 1979 |
| siRNA 126 | 126 | 1980 |
| siRNA 127 | 127 | 1981 |
| siRNA 128 | 128 | 1982 |
| siRNA 129 | 129 | 1983 |
| siRNA 149 | 149 | 2003 |
| siRNA 150 | 150 | 2004 |
| siRNA 152 | 152 | 2006 |
| siRNA 153 | 153 | 2007 |
| siRNA 154 | 154 | 2008 |
| siRNA 157 | 157 | 2011 |
| siRNA 158 | 158 | 2012 |
| siRNA 159 | 159 | 2013 |
| siRNA 161 | 161 | 2015 |
| siRNA 164 | 164 | 2018 |
| siRNA 165 | 165 | 2019 |
| siRNA 166 | 166 | 2020 |
| siRNA 167 | 167 | 2021 |
| siRNA 168 | 168 | 2022 |
| siRNA 169 | 169 | 2023 |
| siRNA 172 | 172 | 2026 |
| siRNA 174 | 174 | 2028 |
| siRNA 175 | 175 | 2029 |
| siRNA 177 | 177 | 2031 |
| siRNA 196 | 196 | 2050 |
| siRNA 198 | 198 | 2052 |
| siRNA 199 | 199 | 2053 |
| siRNA 210 | 210 | 2064 |
| siRNA 211 | 211 | 2065 |
| siRNA 212 | 212 | 2066 |
| siRNA 214 | 214 | 2068 |
| siRNA 215 | 215 | 2069 |
| siRNA 216 | 216 | 2070 |
| siRNA 217 | 217 | 2071 |
| siRNA 218 | 218 | 2072 |
| siRNA 219 | 219 | 2073 |
| siRNA 221 | 221 | 2075 |
| siRNA 222 | 222 | 2076 |
| siRNA 223 | 223 | 2077 |
| siRNA 228 | 228 | 2082 |
| siRNA 230 | 230 | 2084 |
| siRNA 231 | 231 | 2085 |
| siRNA 240 | 240 | 2094 |
| siRNA 241 | 241 | 2095 |
| siRNA 245 | 245 | 2099 |
| siRNA 246 | 246 | 2100 |
| siRNA 250 | 250 | 2104 |
| siRNA 252 | 252 | 2106 |
| siRNA 253 | 253 | 2107 |
| siRNA 254 | 254 | 2108 |
| siRNA 255 | 255 | 2109 |
| siRNA 260 | 260 | 2114 |
| siRNA 261 | 261 | 2115 |
| siRNA 262 | 262 | 2116 |
| siRNA 263 | 263 | 2117 |
| siRNA 265 | 265 | 2119 |
| siRNA 266 | 266 | 2120 |
| siRNA 271 | 271 | 2125 |
| siRNA 272 | 272 | 2126 |
| siRNA 274 | 274 | 2128 |
| siRNA 280 | 280 | 2134 |
| siRNA 282 | 282 | 2136 |
| siRNA 289 | 289 | 2143 |
| siRNA 290 | 290 | 2144 |
| siRNA 291 | 291 | 2145 |
| siRNA 292 | 292 | 2146 |
| siRNA 293 | 293 | 2147 |
| siRNA 299 | 299 | 2153 |
| siRNA 304 | 304 | 2158 |
| siRNA 321 | 321 | 2175 |
| siRNA 323 | 323 | 2177 |
| siRNA 325 | 325 | 2179 |
| siRNA 326 | 326 | 2180 |
| siRNA 328 | 328 | 2182 |
| siRNA 329 | 329 | 2183 |
| siRNA 330 | 330 | 2184 |
| siRNA 331 | 331 | 2185 |
| siRNA 332 | 332 | 2186 |
| siRNA 333 | 333 | 2187 |
| siRNA 334 | 334 | 2188 |
| siRNA 335 | 335 | 2189 |
| siRNA 337 | 337 | 2191 |
| siRNA 338 | 338 | 2192 |
| siRNA 339 | 339 | 2193 |
| siRNA 342 | 342 | 2196 |
| siRNA 347 | 347 | 2201 |
| siRNA 349 | 349 | 2203 |
| siRNA 350 | 350 | 2204 |
| siRNA 352 | 352 | 2206 |
| siRNA 353 | 353 | 2207 |
| siRNA 356 | 356 | 2210 |
| siRNA 377 | 377 | 2231 |
| siRNA 380 | 380 | 2234 |
| siRNA 382 | 382 | 2236 |
| siRNA 386 | 386 | 2240 |
| siRNA 388 | 388 | 2242 |
| siRNA 391 | 391 | 2245 |
| siRNA 392 | 392 | 2246 |
| siRNA 393 | 393 | 2247 |
| siRNA 394 | 394 | 2248 |
| siRNA 397 | 397 | 2251 |
| siRNA 398 | 398 | 2252 |
| siRNA 399 | 399 | 2253 |
| siRNA 402 | 402 | 2256 |
| siRNA 404 | 404 | 2258 |
| siRNA 405 | 405 | 2259 |
| siRNA 411 | 411 | 2265 |
| siRNA 412 | 412 | 2266 |
| siRNA 413 | 413 | 2267 |
| siRNA 414 | 414 | 2268 |
| siRNA 415 | 415 | 2269 |
| siRNA 417 | 417 | 2271 |
| siRNA 419 | 419 | 2273 |
| siRNA 420 | 420 | 2274 |
| siRNA 421 | 421 | 2275 |
| siRNA 422 | 422 | 2276 |
| siRNA 423 | 423 | 2277 |
| siRNA 424 | 424 | 2278 |
| siRNA 425 | 425 | 2279 |
| siRNA 426 | 426 | 2280 |
| siRNA 427 | 427 | 2281 |
| siRNA 428 | 428 | 2282 |
| siRNA 429 | 429 | 2283 |
| siRNA 430 | 430 | 2284 |

TABLE 4-continued

Subset A

| siRNA Name | Sense Strand Sequence- SEQ ID NO: | Antisense Strand Sequence- SEQ ID NO: |
| --- | --- | --- |
| siRNA 431 | 431 | 2285 |
| siRNA 435 | 435 | 2289 |
| siRNA 481 | 481 | 2335 |
| siRNA 484 | 484 | 2338 |
| siRNA 506 | 506 | 2360 |
| siRNA 509 | 509 | 2363 |
| siRNA 517 | 517 | 2371 |
| siRNA 519 | 519 | 2373 |
| siRNA 520 | 520 | 2374 |
| siRNA 565 | 565 | 2419 |
| siRNA 570 | 570 | 2424 |
| siRNA 571 | 571 | 2425 |
| siRNA 572 | 572 | 2426 |
| siRNA 589 | 589 | 2443 |
| siRNA 607 | 607 | 2461 |
| siRNA 608 | 608 | 2462 |
| siRNA 610 | 610 | 2464 |
| siRNA 611 | 611 | 2465 |
| siRNA 612 | 612 | 2466 |
| siRNA 616 | 616 | 2470 |
| siRNA 617 | 617 | 2471 |
| siRNA 620 | 620 | 2474 |
| siRNA 623 | 623 | 2477 |
| siRNA 635 | 635 | 2489 |
| siRNA 637 | 637 | 2491 |
| siRNA 640 | 640 | 2494 |
| siRNA 643 | 643 | 2497 |
| siRNA 653 | 653 | 2507 |
| siRNA 672 | 672 | 2526 |
| siRNA 673 | 673 | 2527 |
| siRNA 674 | 674 | 2528 |
| siRNA 675 | 675 | 2529 |
| siRNA 676 | 676 | 2530 |
| siRNA 677 | 677 | 2531 |
| siRNA 678 | 678 | 2532 |
| siRNA 679 | 679 | 2533 |
| siRNA 681 | 681 | 2535 |
| siRNA 682 | 682 | 2536 |
| siRNA 683 | 683 | 2537 |
| siRNA 684 | 684 | 2538 |
| siRNA 686 | 686 | 2540 |
| siRNA 687 | 687 | 2541 |
| siRNA 689 | 689 | 2543 |
| siRNA 692 | 692 | 2546 |
| siRNA 695 | 695 | 2549 |
| siRNA 830 | 830 | 2684 |
| siRNA 834 | 834 | 2688 |
| siRNA 841 | 841 | 2695 |
| siRNA 842 | 842 | 2696 |
| siRNA 843 | 843 | 2697 |
| siRNA 844 | 844 | 2698 |
| siRNA 850 | 850 | 2704 |
| siRNA 851 | 851 | 2705 |
| siRNA 852 | 852 | 2706 |
| siRNA 853 | 853 | 2707 |
| siRNA 854 | 854 | 2708 |
| siRNA 856 | 856 | 2710 |
| siRNA 857 | 857 | 2711 |
| siRNA 859 | 859 | 2713 |
| siRNA 866 | 866 | 2720 |
| siRNA 868 | 868 | 2722 |
| siRNA 871 | 871 | 2725 |
| siRNA 872 | 872 | 2726 |
| siRNA 876 | 876 | 2730 |
| siRNA 887 | 887 | 2741 |
| siRNA 888 | 888 | 2742 |
| siRNA 890 | 890 | 2744 |
| siRNA 892 | 892 | 2746 |
| siRNA 893 | 893 | 2747 |
| siRNA 894 | 894 | 2748 |
| siRNA 897 | 897 | 2751 |
| siRNA 900 | 900 | 2754 |
| siRNA 902 | 902 | 2756 |
| siRNA 907 | 907 | 2761 |
| siRNA 911 | 911 | 2765 |
| siRNA 912 | 912 | 2766 |
| siRNA 913 | 913 | 2767 |
| siRNA 914 | 914 | 2768 |
| siRNA 915 | 915 | 2769 |
| siRNA 916 | 916 | 2770 |
| siRNA 917 | 917 | 2771 |
| siRNA 918 | 918 | 2772 |
| siRNA 919 | 919 | 2773 |
| siRNA 920 | 920 | 2774 |
| siRNA 921 | 921 | 2775 |
| siRNA 922 | 922 | 2776 |
| siRNA 925 | 925 | 2779 |
| siRNA 945 | 945 | 2799 |
| siRNA 968 | 968 | 2822 |
| siRNA 1001 | 1001 | 2855 |
| siRNA 1002 | 1002 | 2856 |
| siRNA 1005 | 1005 | 2859 |
| siRNA 1006 | 1006 | 2860 |
| siRNA 1009 | 1009 | 2863 |
| siRNA 1010 | 1010 | 2864 |
| siRNA 1011 | 1011 | 2865 |
| siRNA 1013 | 1013 | 2867 |
| siRNA 1028 | 1028 | 2882 |
| siRNA 1032 | 1032 | 2886 |
| siRNA 1037 | 1037 | 2891 |
| siRNA 1052 | 1052 | 2906 |
| siRNA 1053 | 1053 | 2907 |
| siRNA 1054 | 1054 | 2908 |
| siRNA 1055 | 1055 | 2909 |
| siRNA 1057 | 1057 | 2911 |
| siRNA 1058 | 1058 | 2912 |
| siRNA 1064 | 1064 | 2918 |
| siRNA 1112 | 1112 | 2966 |
| siRNA 1122 | 1122 | 2976 |
| siRNA 1124 | 1124 | 2978 |
| siRNA 1126 | 1126 | 2980 |
| siRNA 1127 | 1127 | 2981 |
| siRNA 1133 | 1133 | 2987 |
| siRNA 1134 | 1134 | 2988 |
| siRNA 1136 | 1136 | 2990 |
| siRNA 1137 | 1137 | 2991 |
| siRNA 1147 | 1147 | 3001 |
| siRNA 1148 | 1148 | 3002 |
| siRNA 1149 | 1149 | 3003 |
| siRNA 1151 | 1151 | 3005 |
| siRNA 1153 | 1153 | 3007 |
| siRNA 1154 | 1154 | 3008 |
| siRNA 1155 | 1155 | 3009 |
| siRNA 1157 | 1157 | 3011 |
| siRNA 1158 | 1158 | 3012 |
| siRNA 1161 | 1161 | 3015 |
| siRNA 1162 | 1162 | 3016 |
| siRNA 1163 | 1163 | 3017 |
| siRNA 1164 | 1164 | 3018 |
| siRNA 1165 | 1165 | 3019 |
| siRNA 1166 | 1166 | 3020 |
| siRNA 1171 | 1171 | 3025 |
| siRNA 1172 | 1172 | 3026 |
| siRNA 1175 | 1175 | 3029 |
| siRNA 1181 | 1181 | 3035 |
| siRNA 1182 | 1182 | 3036 |
| siRNA 1184 | 1184 | 3038 |
| siRNA 1248 | 1248 | 3102 |
| siRNA 1249 | 1249 | 3103 |
| siRNA 1252 | 1252 | 3106 |
| siRNA 1253 | 1253 | 3107 |
| siRNA 1259 | 1259 | 3113 |
| siRNA 1276 | 1276 | 3130 |
| siRNA 1285 | 1285 | 3139 |
| siRNA 1310 | 1310 | 3164 |
| siRNA 1315 | 1315 | 3169 |
| siRNA 1338 | 1338 | 3192 |
| siRNA 1343 | 1343 | 3197 |

TABLE 4-continued

Subset A

| siRNA Name | Sense Strand Sequence- SEQ ID NO: | Antisense Strand Sequence- SEQ ID NO: |
|---|---|---|
| siRNA 1347 | 1347 | 3201 |
| siRNA 1348 | 1348 | 3202 |
| siRNA 1349 | 1349 | 3203 |
| siRNA 1350 | 1350 | 3204 |
| siRNA 1351 | 1351 | 3205 |
| siRNA 1352 | 1352 | 3206 |
| siRNA 1378 | 1378 | 3232 |
| siRNA 1405 | 1405 | 3259 |
| siRNA 1407 | 1407 | 3261 |
| siRNA 1413 | 1413 | 3267 |
| siRNA 1414 | 1414 | 3268 |
| siRNA 1415 | 1415 | 3269 |
| siRNA 1416 | 1416 | 3270 |
| siRNA 1417 | 1417 | 3271 |
| siRNA 1418 | 1418 | 3272 |
| siRNA 1429 | 1429 | 3283 |
| siRNA 1430 | 1430 | 3284 |
| siRNA 1448 | 1448 | 3302 |
| siRNA 1477 | 1477 | 3331 |
| siRNA 1487 | 1487 | 3341 |
| siRNA 1488 | 1488 | 3342 |
| siRNA 1489 | 1489 | 3343 |
| siRNA 1493 | 1493 | 3347 |
| siRNA 1494 | 1494 | 3348 |
| siRNA 1519 | 1519 | 3373 |
| siRNA 1523 | 1523 | 3377 |
| siRNA 1538 | 1538 | 3392 |
| siRNA 1556 | 1556 | 3410 |
| siRNA 1561 | 1561 | 3415 |
| siRNA 1563 | 1563 | 3417 |
| siRNA 1564 | 1564 | 3418 |
| siRNA 1565 | 1565 | 3419 |
| siRNA 1570 | 1570 | 3424 |
| siRNA 1571 | 1571 | 3425 |
| siRNA 1572 | 1572 | 3426 |
| siRNA 1580 | 1580 | 3434 |
| siRNA 1581 | 1581 | 3435 |
| siRNA 1589 | 1589 | 3443 |
| siRNA 1597 | 1597 | 3451 |
| siRNA 1598 | 1598 | 3452 |
| siRNA 1601 | 1601 | 3455 |
| siRNA 1602 | 1602 | 3456 |
| siRNA 1603 | 1603 | 3457 |
| siRNA 1604 | 1604 | 3458 |
| siRNA 1605 | 1605 | 3459 |
| siRNA 1606 | 1606 | 3460 |
| siRNA 1610 | 1610 | 3464 |
| siRNA 1611 | 1611 | 3465 |
| siRNA 1613 | 1613 | 3467 |
| siRNA 1614 | 1614 | 3468 |
| siRNA 1617 | 1617 | 3471 |
| siRNA 1693 | 1693 | 3547 |
| siRNA 1699 | 1699 | 3553 |
| siRNA 1701 | 1701 | 3555 |
| siRNA 1702 | 1702 | 3556 |
| siRNA 1703 | 1703 | 3557 |
| siRNA 1722 | 1722 | 3576 |
| siRNA 1740 | 1740 | 3594 |
| siRNA 1741 | 1741 | 3595 |
| siRNA 1742 | 1742 | 3596 |
| siRNA 1745 | 1745 | 3599 |
| siRNA 1747 | 1747 | 3601 |
| siRNA 1748 | 1748 | 3602 |
| siRNA 1749 | 1749 | 3603 |
| siRNA 1751 | 1751 | 3605 |
| siRNA 1754 | 1754 | 3608 |
| siRNA 1755 | 1755 | 3609 |
| siRNA 1779 | 1779 | 3633 |
| siRNA 1780 | 1780 | 3634 |
| siRNA 1784 | 1784 | 3638 |
| siRNA 1787 | 1787 | 3641 |
| siRNA 1788 | 1788 | 3642 |
| siRNA 1798 | 1798 | 3652 |
| siRNA 1799 | 1799 | 3653 |
| siRNA 1800 | 1800 | 3654 |
| siRNA 1801 | 1801 | 3655 |
| siRNA 1802 | 1802 | 3656 |
| siRNA 1803 | 1803 | 3657 |

Subset A includes 102 siRNA sequences that are cross-reactive with NHP ANGPTL4 mRNA (siRNAs 33, 34, 35, 36, 56, 121, 272, 280, 282, 289, 290, 291, 292, 293, 321, 323, 326, 328, 329, 330, 331, 332, 333, 334, 335, 337, 338, 339, 342, 347, 349, 411, 412, 430, 431, 435, 481, 484, 509, 517, 519, 520, 565, 620, 635, 637, 640, 830, 834, 841, 842, 843, 844, 850, 871, 872, 876, 887, 888, 894, 897, 902, 945, 1001, 1002, 1005, 1037, 1133, 1134, 1137, 1149, 1151, 1153, 1154, 1155, 1157, 1158, 1161, 1162, 1164, 1165, 1166, 1171, 1172, 1248, 1249, 1315, 1338, 1343, 1347, 1348, 1429, 1430, 1570, 1571, 1572, 1610, 1611, 1617, 1780, 1784, and 1787). The siRNAs in subset A that may be cross-reactive with NHP ANGPTL4 mRNA were tested in vitro (see, e.g., Table 5). In some cases, the sense strand of any of these siRNAs comprises modification pattern 1S. In some cases, the antisense strand of any of these siRNAs comprises modification pattern 1AS.

The siRNAs in subset A have the following characteristics:

Cross-reactivity: With 19mer in human ANGPTL4 mRNA, with 17mer/19mer in NHP ANGPTL4

Specificity category: For human and NHP: AS2 or better, SS3 or better miRNA seeds: AS+SS strand: seed region not conserved in human, mouse, and rat and not present in ≥4 species Off-target frequency: ≤20 human off-targets matched with 2 mismatches in antisense strand SNPs: siRNA target sites do not harbor SNPs with a MAF≥1% (pos. 2-18)

The siRNA sequences in subset A were selected for more stringent specificity to yield subset B. Subset B includes 323 siRNAs (siRNAs 32, 33, 34, 35, 36, 56, 57, 58, 59, 61, 62, 63, 64, 79, 80, 112, 116, 117, 118, 119, 120, 125, 126, 127, 128, 129, 149, 150, 152, 153, 157, 158, 159, 161, 164, 165, 166, 167, 168, 169, 172, 174, 175, 196, 199, 211, 212, 214, 215, 216, 217, 218, 219, 221, 222, 223, 228, 230, 231, 240, 241, 245, 246, 250, 252, 253, 254, 255, 260, 261, 262, 263, 265, 266, 271, 272, 274, 280, 289, 290, 291, 292, 293, 299, 304, 321, 323, 325, 326, 328, 329, 330, 331, 332, 333, 334, 335, 337, 338, 339, 342, 347, 349, 350, 352, 353, 356, 380, 382, 386, 388, 391, 392, 393, 394, 397, 398, 399, 402, 404, 405, 411, 412, 413, 414, 415, 420, 421, 422, 423, 424, 425, 426, 427, 428, 429, 430, 431, 435, 484, 517, 519, 520, 565, 570, 571, 572, 607, 608, 610, 611, 612, 616, 617, 620, 635, 637, 640, 672, 673, 674, 675, 676, 677, 678, 679, 681, 682, 683, 684, 686, 687, 689, 692, 695, 830, 841, 842, 843, 844, 850, 851, 852, 853, 854, 856, 857, 866, 868, 871, 872, 876, 887, 888, 890, 892, 893, 894, 902, 911, 912, 913, 914, 915, 916, 917, 918, 919, 920, 921, 922, 945, 1001, 1002, 1005, 1006, 1009, 1010, 1011, 1013, 1028, 1032, 1052, 1053, 1054, 1055, 1057, 1058, 1112, 1122, 1124, 1126, 1127, 1133, 1134, 1147, 1148, 1149, 1151, 1153, 1154, 1155, 1157, 1158, 1161, 1162, 1164, 1165, 1166, 1175, 1182, 1184, 1252, 1253, 1259, 1276, 1285, 1310, 1315, 1343, 1347, 1348, 1349, 1350, 1351, 1405, 1407, 1413, 1414, 1415, 1416, 1417, 1418, 1429, 1430, 1448, 1519, 1523, 1556, 1561, 1563, 1564, 1565, 1571, 1572, 1580, 1581, 1589, 1597, 1601, 1602, 1603, 1604, 1605, 1606, 1611, 1613, 1614, 1693, 1699, 1701, 1702, 1703, 1722, 1740, 1741, 1742, 1745, 1747, 1748, 1749, 1751, 1754, 1755, 1779, 1780, 1784, 1788, 1798, 1799, 1801, 1802, and 1803). This subset includes 85 siRNA sequences that are cross-reactive with NHP ANGPTL4 mRNA (siRNAs 33, 34, 35, 36, 56, 272, 280, 289, 290, 291, 292, 293, 321, 323, 326, 328, 329, 330, 331, 332, 333, 334, 335, 337, 338, 339, 342, 347, 349, 411, 412, 430, 431, 435, 484, 517, 519, 520, 565, 620, 635, 637, 640, 830, 841, 842, 843, 844, 850, 871, 872, 876, 887, 888, 894, 902, 945, 1001, 1002, 1005, 1133, 1134, 1149, 1151, 1153, 1154, 1155, 1157, 1158, 1161, 1162, 1164, 1165, 1166, 1315, 1343, 1347, 1348, 1429, 1430, 1571, 1572, 1611, 1780, and 1784).

The siRNAs in subset B have the following characteristics:
  Cross-reactivity: With 19mer in human ANGPTL4 mRNA, with 17mer/19mer in NHP ANGPTL4
  Specificity category: For human and NHP: AS2 or better, SS3 or better
  miRNA seeds: AS+SS strand: seed region not conserved in human, mouse, and rat and not present in >4 species
  Off-target frequency: ≤15 human off-targets matched with 2 mismatches in antisense strand
  SNPs: siRNA target sites do not harbor SNPs with a MAF≥1% (pos. 2-18)

The siRNA sequences in subset B were further selected for absence of seed regions in the AS strand that are identical to a seed region of known human miRNA to yield subset C. Subset C includes 183 siRNAs (siRNAs 32, 36, 56, 57, 58, 61, 62, 79, 80, 117, 119, 125, 126, 128, 149, 152, 157, 158, 159, 161, 165, 166, 167, 168, 169, 174, 196, 211, 212, 217, 218, 219, 230, 231, 245, 246, 253, 260, 261, 262, 271, 272, 280, 289, 291, 292, 293, 304, 321, 323, 325, 326, 328, 330, 331, 332, 333, 334, 337, 338, 342, 347, 349, 352, 353, 356, 380, 382, 386, 388, 391, 392, 394, 399, 413, 414, 415, 422, 423, 424, 425, 426, 435, 517, 519, 520, 565, 571, 607, 608, 612, 617, 620, 635, 640, 672, 673, 674, 675, 678, 679, 681, 683, 684, 687, 692, 842, 843, 850, 851, 854, 866, 868, 876, 892, 893, 902, 911, 912, 913, 914, 916, 919, 945, 1001, 1002, 1006, 1010, 1028, 1052, 1053, 1054, 1055, 1057, 1112, 1124, 1127, 1147, 1149, 1151, 1153, 1155, 1157, 1164, 1175, 1182, 1184, 1259, 1276, 1285, 1315, 1343, 1349, 1350, 1351, 1405, 1407, 1413, 1415, 1418, 1564, 1571, 1581, 1589, 1597, 1601, 1602, 1603, 1604, 1605, 1606, 1613, 1614, 1693, 1701, 1722, 1740, 1745, 1751, 1755, 1801, 1802, and 1803). This subset includes 47 siRNA sequences that are cross-reactive with NHP ANGPTL4 mRNA (siRNAs 36, 56, 272, 280, 289, 291, 292, 293, 321, 323, 326, 328, 330, 331, 332, 333, 334, 337, 338, 342, 347, 349, 435, 517, 519, 520, 565, 620, 635, 640, 842, 843, 850, 876, 902, 945, 1001, 1002, 1149, 1151, 1153, 1155, 1157, 1164, 1315, 1343, and 1571).

The siRNAs in subset C have the following characteristics:
  Cross-reactivity: With 19mer in human ANGPTL4 mRNA, with 17mer/19mer in NHP ANGPTL4
  Specificity category: For human and NHP: AS2 or better, SS3 or better
  miRNA seeds: AS+SS strand: seed region not conserved in human, mouse, and rat and not present in >4 species. AS strand: seed region not identical to seed region of known human miRNA
  Off-target frequency: ≤15 human off-targets matched with 2 mismatches by antisense strand
  SNPs: siRNA target sites do not harbor SNPs with a MAF≥1% (pos. 2-18)

The siRNA sequences in subset C were also selected for absence of seed regions in the AS or S strands that are identical to a seed region of known human miRNA to yield subset D. Subset D includes 114 siRNAs (siRNAs 32, 36, 56, 58, 61, 62, 80, 117, 119, 126, 152, 154, 157, 158, 159, 161, 166, 169, 174, 177, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 653, 672, 678, 679, 681, 683, 692, 842, 843, 851, 854, 859, 876, 892, 900, 913, 914, 919, 968, 1001, 1002, 1054, 1057, 1064, 1112, 1124, 1157, 1164, 1182, 1184, 1248, 1259, 1343, 1351, 1352, 1415, 1418, 1564, 1581, 1602, 1614, 1693, 1701, 1722, 1740, 1751, 1755, and 1787). This subset includes 26 siRNA sequences that are cross-reactive with NHP ANGPTL4 mRNA (siRNAs 36, 56, 272, 280, 289, 293, 328, 330, 331, 332, 333, 334, 337, 342, 347, 349, 435, 520, 842, 843, 876, 1001, 1002, 1157, 1164, and 1343).

The siRNAs in subset D have the following characteristics:
  Cross-reactivity: With 19mer in human ANGPTL4 mRNA, with 17mer/19mer in NHP ANGPTL4
  Specificity category: For human and NHP: AS2 or better, SS3 or better
  miRNA seeds: AS+SS strand: seed region not conserved in human, mouse, and rat and not present in >4 species. AS+SS strand: seed region not identical to seed region of known human miRNA
  Off-target frequency: ≤20 human off-targets matched with 2 mismatches by antisense strand
  SNPs: siRNA target sites do not harbor SNPs with a MAF≥1% (pos. 2-18)

The siRNA sequences in subset D were further selected for more stringent specificity to yield subset E. Subset E includes 104 siRNAs (siRNAs 32, 36, 56, 58, 61, 62, 80, 117, 119, 126, 152, 157, 158, 159, 161, 166, 169, 174, 196, 211, 212, 217, 218, 230, 231, 245, 253, 260, 261, 271, 272, 280, 289, 293, 304, 328, 330, 331, 332, 333, 334, 337, 342, 347, 349, 353, 356, 386, 388, 391, 392, 394, 414, 415, 422, 423, 424, 426, 435, 520, 571, 608, 612, 617, 672, 678, 679, 681, 683, 692, 842, 843, 851, 854, 876, 892, 913, 914, 919, 1001, 1002, 1054, 1057, 1112, 1124, 1157, 1164, 1182, 1184, 1259, 1343, 1351, 1415, 1418, 1564, 1581, 1602, 1614, 1693, 1701, 1722, 1740, 1751, and 1755). This set includes 26 siRNA sequences that are cross-reactive with NHP ANGPTL4 mRNA (siRNAs 36, 56, 272, 280, 289, 293, 328, 330, 331, 332, 333, 334, 337, 342, 347, 349, 435, 520, 842, 843, 876, 1001, 1002, 1157, 1164, and 1343).

The siRNAs in subset E have the following characteristics:
  Cross-reactivity: With 19mer in human ANGPTL4 mRNA, with 17mer/19mer in NHP ANGPTL4
  Specificity category: For human and NHP: AS2 or better, SS3 or better
  miRNA seeds: AS+SS strand: seed region not conserved in human, mouse, and rat and not present in >4 species. AS+SS strand: seed region not identical to seed region of known human miRNA Off-target frequency: ≤15 human off-targets matched with 2 mismatches by antisense strand SNPs: siRNA target sites do not harbor SNPs with a MAF≥1% (pos. 2-18)

The siRNA sequences targeting ANGPTL4 can also be selected using other criteria. Subset F includes 115 siRNAs (siRNAs 32, 57, 119, 120, 125, 126, 127, 128, 164, 165, 166, 167, 168, 169, 174, 175, 176, 177, 199, 250, 252, 255, 260, 261, 262, 263, 353, 356, 363, 372, 403, 404, 412, 413, 417, 423, 424, 425, 426, 427, 428, 429, 565, 570, 571, 572, 589, 607, 608, 610, 611, 612, 672, 673, 674, 675, 676, 677, 678, 679, 689, 695, 759, 801, 851, 852, 853, 854, 857, 859, 866, 868, 907, 911, 912, 913, 914, 915, 918, 919, 972, 1006, 1009, 1010, 1011, 1013, 1028, 1034, 1037, 1048, 1126, 1276, 1285, 1349, 1489, 1490, 1564, 1565, 1580, 1581, 1589, 1597, 1598, 1601, 1602, 1603, 1604, 1605, 1606, 1610, 1701, 1702, 1789, 1840, and 1842).

The siRNAs in subset F met the following criteria:

Cross-reactivity: With 19mer in human ANGPTL4 mRNA. One or fewer mismatches with 19mer in either rhesus or cynomolgus monkey.

Specificity category: For human: AS2 or better, SS3 or better. For NHP: AS3 or better, SS3 or better miRNA seeds: AS+SS strand: seed region conserved in <4 species (out of 7). AS and SS strand: seed region not conserved between human, mouse and rat Off-target frequency: For human: no perfect match or single mismatches. For NHP: no perfect match SNPs: siRNA target sites do not harbor SNPs with a MAF≥1% (pos. 2-18)

Subset G includes 20 siRNAs (siRNAs 32, 570, 571, 572, 589, 607, 759, 801, 1276, 1285, 1489, 1490, 1564, 1580, 1581, 1589, 1597, 1702, 1840, and 1842). The siRNAs in subset G include siRNAs from subset F that were tested in vitro (see, e.g., Table 6). In some cases, the sense strand of any of the siRNAs of subset G comprises modification pattern 2S. In some cases, the antisense strand of any of the siRNAs of subset G comprises modification pattern 3AS. The siRNAs in subset G may comprise any other modification pattern(s).

Any siRNA among any of subsets A-G may comprise any modification pattern described herein. If a sequence is a different number of nucleotides in length than a modification pattern, the modification pattern may still be used with the appropriate number of additional nucleotides added 5' or 3' to match the number of nucleotides in the modification pattern. For example, if a sense or antisense strand of the siRNA among any of subsets A-G comprises 19 nucleotides, and a modification pattern comprises 21 nucleotides, UU may be added onto the 5' end of the sense or antisense strand.

Example 3: Chemically Modified ANGPTL4 siRNAs

The siRNAs targeting ANGPTL4 can be synthesized with chemical modifications with the sense strand having modification pattern 1S (SEQ ID NO: 13954) and the antisense strand having modification pattern 1AS (SEQ ID NO: 13960). In addition, adenosine can be placed at position 19 in the sense strand and uridine at position 1 in the antisense strand.

The siRNAs targeting ANGPTL4 can also be synthesized with chemical modifications with the sense strand having modification pattern 2S (SEQ ID NO: 13955) and the antisense strand having modification pattern 3AS (SEQ ID NO: 13962). In addition, adenosine can be placed at position 19 in the sense strand and uridine at position 1 in the antisense strand.

The siRNAs targeting ANGPTL4 can also be synthesized with chemical modifications with the sense strand having modification pattern 2S (SEQ ID NO: 13955) and the antisense strand having modification pattern 9AS (SEQ ID NO: 13968). In addition, adenosine can be placed at position 19 in the sense strand and uridine at position 1 in the antisense strand.

The siRNAs targeting ANGPTL4 can also be synthesized with chemical modifications with the sense strand having modification pattern 3S (SEQ ID NO: 13954) and the antisense strand having modification pattern 3AS (SEQ ID NO: 13962). In addition, adenosine can be placed at position 19 in the sense strand and uridine at position 1 in the antisense strand.

Example 4: Screening ANGPTL4 siRNAs for Activity in Cells in Culture

Chemically modified ANGPTL4 siRNAs cross reactive for human and non-human primate were assayed for ANGPTL4 mRNA knockdown activity in cells in culture. U-138 MG (ATCC® HTB-16) cells were seeded in 96-well tissue culture plates at a cell density of 7,500 cells per well in EMEM (BD Biosciences Catalog No. 670086) supplemented with 10% fetal bovine serum and incubated overnight in a water-jacketed, humidified incubator at 37° C. in an atmosphere composed of air plus 5% carbon dioxide. The ANGPTL4 siRNAs were individually transfected into U-138 MG cells in duplicate wells at 10 nM final concentration using 0.3 μL Lipofectamine RNAiMax (Fisher) per well. Silencer Select Negative Control #1 (ThermoFisher, Catalog #4390843) was transfected at 10 nM final concentration as a control. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL4 mRNA from each well was measured in triplicate by real-time qPCR on an Applied Biosystems 7500 Fast Real-Time PCR machine using TaqMan Gene Expression Assay for human ANGPTL4 (ThermoFisher, assay #Hs01101127 m1). The level of PPIA mRNA was measured using TaqMan Gene Expression Assay (ThermoFisher, assay #Hs99999904 ml) and used to determine relative ANGPTL4 mRNA levels in each well using the delta-delta Ct method. All data were normalized to relative ANGPTL4 mRNA levels in untreated U-138 MG cells. A subset of the siRNAs were also tested at 1 nM concentration. Results are shown in Table 5 and Table 6. The siRNAs in Table 5 (ETD00646-ETD00747) each comprised a sense strand having modification pattern 1S, and an sense strand having modification pattern 1AS. The siRNAs in Table 6 (ETD00915-ETD00934) each comprised a sense strand having modification pattern 2S, and an sense strand having modification pattern 3AS.

TABLE 5

Knockdown Activity of ANGPTL4-Specific siRNAs at 1 nM and 10 nM in Human U-138 MG cells

| siRNA name | Sense Strand SEQ ID NO: | Antisense Strand SEQ ID NO: | Relative ANGPTL4 mRNA Level | |
|---|---|---|---|---|
| | | | 1 nM siRNA | 10 nM siRNA |
| Untreated Cells | — | — | 1.00 | 1.00 |
| Negative Control siRNA | — | — | 1.15 | 1.14 |
| ETD00646 | 14012 | 14167 | ND | 0.72 |
| ETD00647 | 14013 | 14168 | ND | 0.97 |
| ETD00648 | 14014 | 14169 | ND | 0.84 |
| ETD00649 | 14015 | 14170 | 0.94 | 0.69 |
| ETD00650 | 14016 | 14171 | ND | 2.08 |
| ETD00651 | 14017 | 14172 | 0.99 | 0.71 |
| ETD00652 | 14018 | 14173 | ND | 1.06 |
| ETD00653 | 14019 | 14174 | 1.03 | 0.63 |
| ETD00654 | 14020 | 14175 | 1.18 | 0.68 |
| ETD00655 | 14021 | 14176 | 1.05 | 0.65 |
| ETD00656 | 14022 | 14177 | ND | 0.86 |
| ETD00657 | 14023 | 14178 | ND | 0.96 |
| ETD00658 | 14024 | 14179 | ND | 0.87 |
| ETD00659 | 14025 | 14180 | ND | 1.02 |
| ETD00660 | 14026 | 14181 | ND | 0.84 |
| ETD00661 | 14027 | 14182 | ND | 0.84 |
| ETD00662 | 14028 | 14183 | ND | 0.82 |
| ETD00663 | 14029 | 14184 | ND | 0.94 |
| ETD00664 | 14030 | 14185 | ND | 0.97 |
| ETD00665 | 14031 | 14186 | ND | 1.22 |
| ETD00666 | 14032 | 14187 | ND | 1.24 |
| ETD00667 | 14033 | 14188 | ND | 0.88 |
| ETD00668 | 14034 | 14189 | ND | 1.00 |
| ETD00669 | 14035 | 14190 | 1.05 | 0.68 |
| ETD00670 | 14036 | 14191 | ND | 0.93 |
| ETD00671 | 14037 | 14192 | ND | 1.59 |
| ETD00672 | 14038 | 14193 | ND | 1.41 |
| ETD00673 | 14039 | 14194 | ND | 1.80 |
| ETD00674 | 14040 | 14195 | ND | 1.87 |
| ETD00675 | 14041 | 14196 | ND | 1.04 |
| ETD00676 | 14042 | 14197 | ND | 1.28 |
| ETD00677 | 14043 | 14198 | ND | 1.39 |
| ETD00678 | 14044 | 14199 | ND | 1.49 |
| ETD00679 | 14045 | 14200 | ND | 1.28 |
| ETD00680 | 14046 | 14201 | ND | 1.52 |
| ETD00681 | 14047 | 14202 | ND | 2.12 |
| ETD00682 | 14048 | 14203 | ND | 0.91 |
| ETD00683 | 14049 | 14204 | 1.06 | 0.47 |
| ETD00684 | 14050 | 14205 | 0.88 | 0.63 |
| ETD00685 | 14051 | 14206 | ND | 1.02 |
| ETD00686 | 14052 | 14207 | 0.79 | 0.66 |
| ETD00687 | 14053 | 14208 | ND | 0.91 |
| ETD00688 | 14054 | 14209 | ND | 0.84 |
| ETD00689 | 14055 | 14210 | 1.01 | 0.51 |
| ETD00690 | 14056 | 14211 | ND | 1.29 |
| ETD00691 | 14057 | 14212 | ND | 0.80 |
| ETD00692 | 14058 | 14213 | ND | 0.78 |
| ETD00693 | 14059 | 14214 | ND | 1.09 |
| ETD00694 | 14060 | 14215 | 1.16 | 0.58 |
| ETD00695 | 14061 | 14216 | ND | 1.79 |
| ETD00696 | 14062 | 14217 | ND | 1.55 |
| ETD00697 | 14063 | 14218 | ND | 1.42 |
| ETD00698 | 14064 | 14219 | ND | 1.83 |
| ETD00699 | 14065 | 14220 | ND | 1.10 |
| ETD00700 | 14066 | 14221 | ND | 1.33 |
| ETD00701 | 14067 | 14222 | ND | 1.13 |
| ETD00702 | 14068 | 14223 | ND | 0.85 |
| ETD00703 | 14069 | 14224 | ND | 1.26 |
| ETD00704 | 14070 | 14225 | ND | 1.14 |
| ETD00705 | 14071 | 14226 | ND | 1.72 |
| ETD00706 | 14072 | 14227 | ND | 1.63 |
| ETD00707 | 14073 | 14228 | ND | 0.92 |
| ETD00708 | 14074 | 14229 | ND | 1.69 |
| ETD00709 | 14075 | 14230 | 1.24 | 0.69 |
| ETD00710 | 14076 | 14231 | ND | 2.23 |
| ETD00711 | 14077 | 14232 | ND | 1.02 |
| ETD00712 | 14078 | 14233 | ND | 1.21 |
| ETD00713 | 14079 | 14234 | 1.09 | 0.48 |
| ETD00714 | 14080 | 14235 | 0.94 | 0.50 |
| ETD00715 | 14081 | 14236 | 0.98 | 0.65 |

TABLE 5-continued

Knockdown Activity of ANGPTL4-Specific siRNAs at 1 nM and 10 nM in Human U-138 MG cells

| siRNA name | Sense Strand SEQ ID NO: | Antisense Strand SEQ ID NO: | Relative ANGPTL4 mRNA Level | |
|---|---|---|---|---|
| | | | 1 nM siRNA | 10 nM siRNA |
| ETD00716 | 14082 | 14237 | 0.91 | 0.59 |
| ETD00717 | 14083 | 14238 | ND | 0.82 |
| ETD00718 | 14084 | 14239 | ND | 1.09 |
| ETD00719 | 14085 | 14240 | ND | 0.84 |
| ETD00720 | 14086 | 14241 | ND | 1.82 |
| ETD00721 | 14087 | 14242 | 0.64 | 0.47 |
| ETD00722 | 14088 | 14243 | ND | 1.52 |
| ETD00723 | 14089 | 14244 | ND | 1.08 |
| ETD00724 | 14090 | 14245 | ND | 0.91 |
| ETD00725 | 14091 | 14246 | ND | 0.93 |
| ETD00726 | 14092 | 14247 | ND | 0.90 |
| ETD00727 | 14093 | 14248 | ND | 0.76 |
| ETD00728 | 14094 | 14249 | 0.94 | 0.43 |
| ETD00729 | 14095 | 14250 | 1.08 | 0.71 |
| ETD00730 | 14096 | 14251 | ND | 0.80 |
| ETD00731 | 14097 | 14252 | 1.25 | 0.56 |
| ETD00732 | 14098 | 14253 | ND | 1.25 |
| ETD00733 | 14099 | 14254 | ND | 0.88 |
| ETD00734 | 14100 | 14255 | ND | 1.15 |
| ETD00735 | 14101 | 14256 | ND | 1.11 |
| ETD00736 | 14102 | 14257 | 0.90 | 0.48 |
| ETD00737 | 14103 | 14258 | ND | 1.10 |
| ETD00738 | 14104 | 14259 | ND | 0.83 |
| ETD00739 | 14105 | 14260 | ND | 1.33 |
| ETD00740 | 14106 | 14261 | ND | 1.40 |
| ETD00741 | 14107 | 14262 | ND | 0.96 |
| ETD00742 | 14108 | 14263 | ND | 1.30 |
| ETD00743 | 14109 | 14264 | 1.04 | 0.63 |
| ETD00744 | 14110 | 14265 | ND | 1.24 |
| ETD00745 | 14111 | 14266 | ND | 1.42 |
| ETD00746 | 14112 | 14267 | ND | 1.20 |
| ETD00747 | 14113 | 14268 | ND | 1.21 |

"—" untreated U-138MG cells; Negative Control siRNA, Silencer Select Negative Control #1;
ND, Not Determined

TABLE 6

Knockdown Activity of ANGPTL4-Specific siRNAs at 1 nM and 10 nM in Human U-138 MG Cells

| siRNA name | Sense Strand SEQ ID NO: | Antisense Strand SEQ ID NO: | Relative ANGPTL4 mRNA Level | |
|---|---|---|---|---|
| | | | 1 nM siRNA | 10 nM siRNA |
| Untreated Cells | — | — | 1.00 | 1.00 |
| Negative Control siRNA | — | — | 1.23 | 1.10 |
| ETD00915 | 14114 | 14269 | 1.05 | 0.85 |
| ETD00916 | 14115 | 14270 | 0.62 | 0.39 |
| ETD00917 | 14116 | 14271 | 0.84 | 0.86 |
| ETD00918 | 14117 | 14272 | 1.02 | 1.03 |
| ETD00919 | 14118 | 14273 | 1.01 | 1.02 |
| ETD00920 | 14119 | 14274 | 0.91 | 1.15 |
| ETD00921 | 14120 | 14275 | 0.78 | 0.48 |
| ETD00922 | 14121 | 14276 | 1.18 | 1.10 |
| ETD00923 | 14122 | 14277 | 0.91 | 0.93 |
| ETD00924 | 14123 | 14278 | 0.82 | 0.57 |
| ETD00925 | 14124 | 14279 | 0.79 | 0.57 |
| ETD00926 | 14125 | 14280 | 0.77 | 0.47 |
| ETD00927 | 14126 | 14281 | 0.98 | 0.73 |
| ETD00928 | 14127 | 14282 | 0.87 | 0.50 |
| ETD00929 | 14128 | 14283 | 0.91 | 0.54 |
| ETD00930 | 14129 | 14284 | 0.85 | 0.58 |
| ETD00931 | 14130 | 14285 | 0.85 | 0.46 |
| ETD00932 | 14131 | 14286 | 1.01 | 0.72 |
| ETD00933 | 14132 | 14287 | 0.38 | 0.33 |
| ETD00934 | 14133 | 14288 | 0.65 | 0.37 |

"—" untreated U-138MG cells; Negative Control siRNA, Silencer Select Negative Control #1;
ND, Not Determined

Example 5: Determining the IC50 of ANGPTL4 siRNAs

The IC50 values for knockdown of ANGPTL4 mRNA by select ANGPTL4 siRNAs were determined in U-138 MG cells. The siRNAs were assayed individually at 30 nM, 10 nM, 3 nM, 1 nM and 0.3 nM, or 3 nM, 1 nM, 0.3 nM, 0.1 nM and 0.03 nM, or 30 nM, 10 nM, 3 nM, 1 nM, 0.3 nM, 0.1 nM and 0.03 nM. The U-138 MG (ATCC® HTB-16) cells were seeded in 96-well tissue culture plates at a cell density of 7,500 cells per well in EMEM (BD Biosciences Catalog No. 670086) supplemented with 10% fetal bovine serum and incubated overnight in a water-jacketed, humidified incubator at 37° C. in an atmosphere composed of air plus 5% carbon dioxide. The ANGPTL4 siRNAs were individually transfected into U-138 MG cells in triplicate wells using 0.3 μL Lipofectamine RNAiMax (Fisher) per well. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL4 mRNA from each well was measured in triplicate by real-time qPCR on an Applied Biosystems 7500 Fast Real-Time PCR machine using TaqMan Gene Expression Assay for human ANGPTL4 (ThermoFisher, assay #Hs01101127 ml). The level of PPIA mRNA was measured using TaqMan Gene Expression Assay (ThermoFisher, assay #Hs99999904 ml) and used to determine relative ANGPTL4 mRNA levels in each well using the delta-delta Ct method. All data were normalized to relative ANGPTL4 mRNA levels in untreated U-138 MG cells. Curve fit was accomplish using the [inhibitor] vs. response (three parameters) function in GraphPad Prism software. Results are shown in Table 7.

TABLE 7

IC50 Values of ANGPTL4 siRNAs in Human U-138 MG Cells

| siRNA | [siRNA] | Relative ANGPTL4 mRNA Levels | IC50 (nM) |
|---|---|---|---|
| — | — | 1 | ND |
| ETD00714 | 30 nM | 0.27 | 4.27 |
|  | 10 nM | 0.43 |  |
|  | 3 nM | 0.52 |  |
|  | 1 nM | 0.69 |  |
|  | 0.3 nM | 0.75 |  |
| ETD00721 | 30 nM | 0.54 | 2.69 |
|  | 10 nM | 0.61 |  |
|  | 3 nM | 0.86 |  |
|  | 1 nM | 1.09 |  |
|  | 0.3 nM | 1.21 |  |
| ETD00728 | 30 nM | 0.57 | 5.10 |
|  | 10 nM | 0.79 |  |
|  | 3 nM | 0.95 |  |
|  | 1 nM | 1.29 |  |
|  | 0.3 nM | 1.27 |  |
| ETD00736 | 30 nM | 0.35 | 8.06 |
|  | 10 nM | 0.36 |  |
|  | 3 nM | 0.76 |  |
|  | 1 nM | 0.71 |  |
|  | 0.3 nM | 0.78 |  |
| ETD00916 | 3 nM | 0.20 | 0.42 |
|  | 1 nM | 0.45 |  |
|  | 0.3 nM | 0.68 |  |
|  | 0.1 nM | 0.89 |  |
|  | 0.03 nM | 1.07 |  |
| ETD00921 | 30 nM | 0.43 | 0.16 |
|  | 10 nM | 0.43 |  |
|  | 3 nM | 0.49 |  |
|  | 1 nM | 0.55 |  |
|  | 0.3 nM | 0.86 |  |
|  | 0.1 nM | 0.93 |  |
|  | 0.03 nM | 1.30 |  |
| ETD00924 | 30 nM | 0.44 | 0.54 |
|  | 10 nM | 0.47 |  |
|  | 3 nM | 0.52 |  |
|  | 1 nM | 0.63 |  |
|  | 0.3 nM | 0.82 |  |
|  | 0.1 nM | 0.91 |  |
|  | 0.03 nM | 0.99 |  |
| ETD00925 | 3 nM | 0.21 | ND |
|  | 1 nM | 0.69 |  |
|  | 0.3 nM | 0.99 |  |
|  | 0.1 nM | 0.87 |  |
|  | 0.03 nM | 0.88 |  |
| ETD00926 | 3 nM | 0.46 | 0.91 |
|  | 1 nM | 0.84 |  |
|  | 0.3 nM | 1.09 |  |
|  | 0.1 nM | 1.21 |  |
|  | 0.03 nM | 1.46 |  |

TABLE 7-continued

IC50 Values of ANGPTL4 siRNAs in Human U-138 MG Cells

| siRNA | [siRNA] | Relative ANGPTL4 mRNA Levels | IC50 (nM) |
|---|---|---|---|
| ETD00928 | 30 nM | 0.56 | 0.13 |
|  | 10 nM | 0.47 |  |
|  | 3 nM | 0.49 |  |
|  | 1 nM | 0.55 |  |
|  | 0.3 nM | 0.76 |  |
|  | 0.1 nM | 1.45 |  |
|  | 0.03 nM | 1.55 |  |
| ETD00930 | 3 nM | 0.70 | ND |
|  | 1 nM | 0.76 |  |
|  | 0.3 nM | 0.95 |  |
|  | 0.1 nM | 0.90 |  |
|  | 0.03 nM | 1.07 |  |
| ETD00931 | 3 nM | 0.29 | ND |
|  | 1 nM | 0.77 |  |
|  | 0.3 nM | 0.88 |  |
|  | 0.1 nM | 0.97 |  |
|  | 0.03 nM | 0.92 |  |
| ETD00933 | 30 nM | 0.26 | 0.13 |
|  | 10 nM | 0.26 |  |
|  | 3 nM | 0.28 |  |
|  | 1 nM | 0.29 |  |
|  | 0.3 nM | 0.37 |  |
|  | 0.1 nM | 0.67 |  |
|  | 0.03 nM | 0.71 |  |
| ETD00934 | 3 nM | 0.53 | ND |
|  | 1 nM | 0.66 |  |
|  | 0.3 nM | 0.65 |  |
|  | 0.1 nM | 0.97 |  |
|  | 0.03 nM | 0.98 |  |

"—" untreated U-138 MG cells;
ND, Not Determined

Some siRNAs having sense strands in accordance with SEQ ID NOs: 13974-13977, and having antisense strands in accordance with SEQ ID NOs: 13982-13985, were synthesized with an alternative modification pattern and are included in Table 8. The siRNAs in Table 8 were based, at least partially, on siRNAs having sense strand sequences comprising the sequences of SEQ ID NOs: 759, 1285, 1580, and 1840, and having antisense strand sequences comprising the sequences of SEQ ID NOs: 2613, 3139, 3434, and 3694.

TABLE 8

Alternative Modification Patterns of Select siRNAs

| ETD# | Sense strand sequence (5'-3') | Antisense strand sequence (5'-3') |
|---|---|---|
| ETD01062 | csasgaGfuGfgAfcu auuugaaasusu | usUfsucaAfauaguc cAfcUfcugsusu |
| ETD01063 | asgscuUfaAfgAfag ggaaucuasusu | usAfsgauUfcccuuc uUfaAfgcususu |
| ETD01064 | gsasucGfaGfgCfug caggauaasusu | usUfsaucCfugcagc cUfcGfaucsusu |
| ETD01065 | csasgaGfuUfcUfug gaauaaaasusu | usUfsuuaUfuccaag aAfcUfcugsusu |

| ETD# | Sense strand - SEQ ID NO: | Antisense strand - SEQ ID NO: |
|---|---|---|
| ETD01062 | 13986 | 14134 |
| ETD01063 | 13987 | 14135 |
| ETD01064 | 13988 | 14136 |
| ETD01065 | 13989 | 14137 |

IC50 values for knockdown of ANGPTL4 mRNA for ETD01062, ETD01063, ETD01064 and ETD01065 ANGPTL4 siRNAs were determined in U-138 MG cells. The siRNAs were assayed individually at 30 nM, 10 nM, 3 nM, 1 nM, 0.3 nM, 0.1 nM and 0.03 nM. The U-138 MG (ATCC® HTB-16) cells were seeded in 96-well tissue culture plates at a cell density of 7,500 cells per well in EMEM (BD Biosciences Catalog No. 670086) supplemented with 10% fetal bovine serum and incubated overnight in a water-jacketed, humidified incubator at 37° C. in an atmosphere composed of air plus 5% carbon dioxide. The ANGPTL4 siRNAs were individually transfected into U-138 MG cells in triplicate wells using 0.3 µL Lipofectamine RNAiMax (Fisher) per well. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL4 mRNA from each well was measured in triplicate by real-time qPCR on an Applied Biosystems 7500 Fast Real-Time PCR machine using TaqMan Gene Expression Assay for human ANGPTL4 (ThermoFisher, assay #Hs01101127_m1). The level of PPIA mRNA was measured using TaqMan Gene Expression Assay (ThermoFisher, assay #Hs99999904_m1) and used to determine relative ANGPTL4 mRNA levels in each well using the delta-delta Ct method. All data were normalized to relative ANGPTL4 mRNA levels in untreated U-138 MG cells. Curve fit was accomplished using the [inhibitor] vs. response (three parameters) function in GraphPad Prism software. Results are shown in Table 9.

TABLE 9

IC50 Values of ETD01062, ETD01063, ETD01064 and ETD01065 ANGPTL4 siRNAs in Human U-138 MG Cells

| siRNA | [siRNA] | Relative ANGPTL4 mRNA Levels | IC50 (nM) |
|---|---|---|---|
| — | — | 1 | ND |
| ETD01062 | 30 nM | 0.41 | 0.22 |
|  | 10 nM | 0.39 |  |
|  | 3 nM | 0.36 |  |
|  | 1 nM | 0.42 |  |
|  | 0.3 nM | 0.63 |  |
|  | 0.1 nM | 0.70 |  |
|  | 0.03 nM | 0.82 |  |
| ETD01063 | 30 nM | 0.68 | 1.24 |
|  | 10 nM | 0.62 |  |
|  | 3 nM | 0.62 |  |
|  | 1 nM | 0.71 |  |
|  | 0.3 nM | 1.54 |  |
|  | 0.1 nM | 1.15 |  |
|  | 0.03 nM | 0.89 |  |
| ETD01064 | 30 nM | 0.83 | 0.25 |
|  | 10 nM | 0.41 |  |
|  | 3 nM | 0.57 |  |
|  | 1 nM | 0.57 |  |
|  | 0.3 nM | 0.71 |  |
|  | 0.1 nM | 1.27 |  |
|  | 0.03 nM | 0.89 |  |
| ETD01065 | 30 nM | 0.24 | 0.07 |
|  | 10 nM | 0.23 |  |
|  | 3 nM | 0.20 |  |
|  | 1 nM | 0.27 |  |
|  | 0.3 nM | 0.31 |  |
|  | 0.1 nM | 0.42 |  |
|  | 0.03 nM | 0.56 |  |

"—" untreated U-138 MG cells;
ND, Not Determined

Example 6: Assessing the Extent of Nuclease Resistance of ANGPTL4 siRNAs

Resistance of select ANGPTL4 siRNAs to nuclease digestion was assessed by incubating the siRNAs in rat liver tritosomes. Each siRNA (7 ng/µL final concentration) was placed into a PCR tube containing a cocktail prepared on ice containing 1× catabolic buffer (Xenotech, Catalog #K5200, Lot #18-1-0698), 0.5× rat tritosomes (Xenotech, Catalog #R0610.LT, Lot #1610405), 0.1 U/4 porcine intestinal heparin (Zageno, Catalog #H3149-10KU). An aliquot was removed, an equal volume of 50 mM EDTA was added, and the sample placed at −80° C. This sample was designated as the 0 hr timepoint. The remainder of the reaction was placed in an Eppendorf Mastercycler Gradient and incubated at 37° C. After incubation for 4 and 24 hours, an aliquot was removed from the reaction and stopped by addition of an equal volume of 50 mM EDTA and placed at −80° C. until analysis by gel electrophoresis. All samples were then thawed on ice and 6×DNA Gel Loading Dye (ThermoFisher Catalog #R0611) was added to 1× final concentration. 20 µL of each sample was loaded onto a 20% polyacrylamide TBE gel (ThermoFisher, Catalog #EC63155BOX). Electrophoresis was carried out at a constant 100V for 75 minutes in an XCell SureLock Mini-Cell Electrophoresis System (ThermoFisher) using 1× TBE (Tris/boric/EDTA) (Fisher, Catalog #FERB52) as the tank buffer. The siRNA was visualized by staining the gel with a 1:10,000 dilution of SYBR Gold (ThermoFisher, Catalog #S-11494) in TBE for 15 minutes at room temperature with rocking. The gel was washed with 1× TBE for 15 minutes and then placed on a FotoPrep1 UV transilluminator (Fotodyne). The gel was imaged using the camera app set on MONO on an iPhone 6s with a yellow gel filter (Neewer) placed over the lens. Band intensity was measured using NIH ImageJ using the "Analyze: Gels" function. The remaining siRNA percent was normalized to the value obtained at the 0 hr timepoint for that siRNA. Results are shown in Table 10. By using this assay, we were able to determine that some siRNAs are more resistant to nuclease digestion with more remaining intact over time compared with other siRNAs with the same modification pattern.

TABLE 10

Resistance of ANGPTL4 siRNAs to Nucleases Present in Rat Liver Tritosomes

| siRNA | Timepoint (hr) | % remaining |
|---|---|---|
| ETD00686 | 0 | 100% |
|  | 4 | 79% |
|  | 24 | 27% |
| ETD00714 | 0 | 100% |
|  | 4 | 66% |
|  | 24 | 33% |
| ETD00721 | 0 | 100% |
|  | 4 | 77% |
|  | 24 | 47% |
| ETD00728 | 0 | 100% |
|  | 4 | 74% |
|  | 24 | 32% |
| ETD00736 | 0 | 100% |
|  | 4 | 81% |
|  | 24 | 39% |
| ETD00916 | 0 | 100% |
|  | 4 | 85% |
|  | 24 | 59% |
| ETD00924 | 0 | 100% |
|  | 4 | 68% |
|  | 24 | 24% |
| ETD00926 | 0 | 100% |
|  | 4 | 74% |
|  | 24 | 47% |

TABLE 10-continued

Resistance of ANGPTL4 siRNAs to Nucleases Present in Rat Liver Tritosomes

| siRNA | Timepoint (hr) | % remaining |
|---|---|---|
| ETD00928 | 0 | 100% |
| | 4 | 73% |
| | 24 | 25% |
| ETD00933 | 0 | 100% |
| | 4 | 73% |
| | 24 | 28% |

Example 7: Screening ANGPTL4 ASOs for Activity in Cells in Culture

ANGPTL4 ASOs with sequences provided in SEQ ID NOs: 3709-13934 and those possessing modification pattern ASO1 (SEQ ID NO: 13969) are to be assayed for ANGPTL4 mRNA reduction activity in cells in culture. A cell line such as ARPE-19 that expresses ANGPTL4 (ATCC® CRL-2302) will be seeded in 96-well tissue culture plates at a cell density of 10,000 cells per well in DMEM supplemented with 10% fetal bovine serum and incubated overnight in a water-jacketed, humidified incubator at 37° C. in an atmosphere of air plus 5% carbon dioxide. The ANGPTL4 ASOs are individually transfected into cells in duplicate wells at 1 uM final concentration using 0.3 uL Lipofectamine RNAiMax (Fisher) per well. A negative control ASO (SEQ ID NO: 13953) is also transfected at 1 uM final concentration. After incubation for 48 hours at 37° C., total RNA is harvested from each well and cDNA prepared using TaqMan® Fast Advanced Cells-to-CT™ Kit (ThermoFisher, Catalog #A35374) according to the manufacturer's instructions. The level of ANGPTL4 mRNA from each well will be measured in triplicate by real-time qPCR on an Applied Biosystems 7500 Fast Real-Time PCR machine using TaqMan Gene Expression Assay for human ANGPTL4 (ThermoFisher, assay #Hs01101127_m1). The level of PPIA mRNA is measured using TaqMan Gene Expression Assay (ThermoFisher, assay #Hs99999904_m1) and used to determine relative ANGPTL4 mRNA levels in each well using the delta-delta Ct method. Data are normalized to relative ANGPTL4 mRNA levels in untreated ARPE-19 cells.

The ANGPTL4 ASOs showing the greatest degree of reduction of ANGPTL4 mRNA at 1 uM are to be tested in a second screen for activity at 100 nM concentration using the transfection procedures as described above.

Example 8: GalNAc Ligand for Hepatocyte Targeting of Oligonucleotides

Without limiting the disclosure to these individual methods, there are at least two general methods for attachment of multivalent N-acetylgalactosamine (GalNAc) ligands to oligonucleotides: solid or solution-phase conjugations. GalNAc ligands may be attached to solid phase resin for 3' conjugation or at the 5' terminus using GalNAc phosphoramidite reagents. GalNAc phosphoramidites may be coupled on solid phase as for other nucleosides in the oligonucleotide sequence at any position in the sequence. Reagents for GalNAc conjugation to oligonucleotides are shown in Table 11.

TABLE 11

GalNAc Conjugation Reagents

| Type of conjugation | Structure |
|---|---|
| Solid phase 3' attachment where squiggly line is rest of oligonucleotide chain and rightmost OH is where attachment' to solid phase is. | 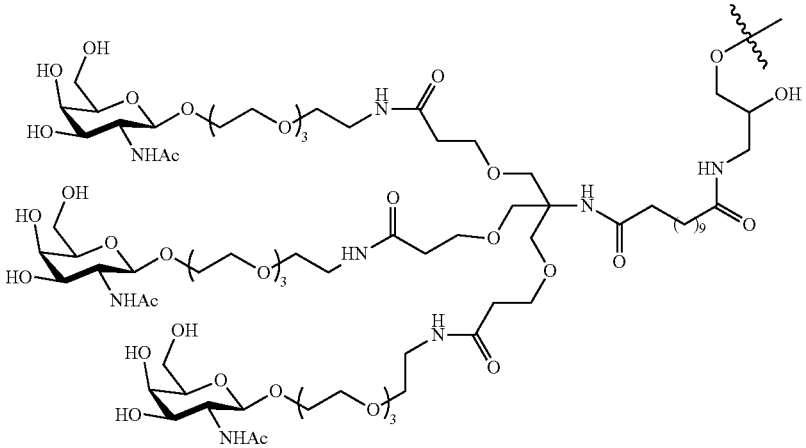 |

This GalNAc ligand may be referred to as "GalNAc23" or "GalNAc#23."

TABLE 11-continued

GalNAc Conjugation Reagents

| Type of conjugation | Structure |
|---|---|
| Solid phase 5' attachment phosphoramidite | *[chemical structure]* |
| Solid phase 5' attachment Phosphoramidite | *[chemical structure]* |

TABLE 11-continued

GalNAc Conjugation Reagents

| Type of conjugation | Structure |
|---|---|
| Solution phase Carboxylic acid for amide coupling anywhere on oligonucleotide | 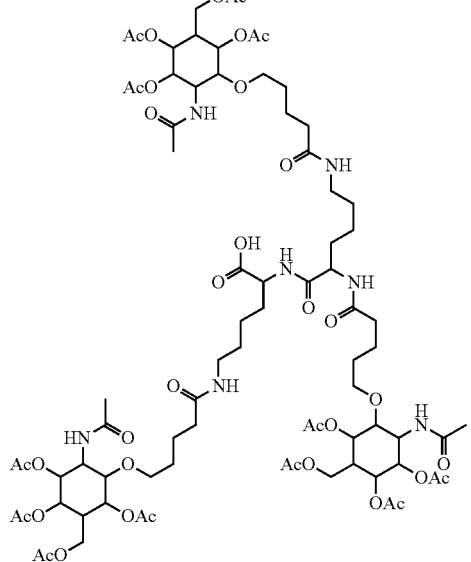 |

Where Ac is an acetyl group or other hydroxyl protecting group that can be removed under basic, acid or reducing conditions.

In solution phase conjugation, the oligonucleotide sequence—including a reactive conjugation site—is formed on the resin. The oligonucleotide is then removed from the resin and GalNAc is conjugated to the reactive site.

The carboxy GalNAc derivatives may be coupled to amino-modified oligonucleotides. The peptide coupling conditions are known to the skilled in the art using a carbodiimide coupling agent like DCC (N,N'-Dicyclohexylcarbodiimide), EDC (N-(3-dimethylaminopropyl)-N'-ethylcarbodiimide) or EDC.HCl (N-(3-dimethylaminopropyl)-N'-ethylcarbodiimide hydrochloride and an additive like HOBt (1-hydroxybenztriazole), HOSu (N-hydroxysuccinimide), TBTU (N,N,N,N-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combinations thereof such as TBTU/HOBt or HBTU/HOAt to form activated amine-reactive esters.

Amine groups may be incorporated into oligonucleotides using a number of known, commercially available reagents at the 5' terminus, 3' terminus or anywhere in between.

Non-limiting examples of reagents for oligonucleotide synthesis to incorporate an amino group include:
5' attachment:
6-(4-Monomethoxytritylamino)hexyl-(2-cyanoethyl)-(N,N-diisopropyl)-phosphoramidite CAS Number: 114616-27-2
5'-Amino-Modifier TEG CE-Phosphoramidite
10-(O-trifluoroacetamido-N-ethyl)-triethyleneglycol-1-[(2-cyanoethyl)-(N,N-diisopropyl)]-phosphoramidite
3' attachment:
3'-Amino-Modifier Serinol CPG
3-Dimethoxytrityloxy-2-(3-(fluorenylmethoxycarbonylamino)propanamido)propyl-1-O-succinyl-long chain alkylamino-CPG (where CPG stands for controlled-pore glass and is the solid support)
Amino-Modifier Serinol Phosphoramidite
3-Dimethoxytrityloxy-2-(3-(fluorenylmethoxycarbonylamino)propanamido)propyl-1-O-(2-cyanoethyl)-(N,N-diisopropyl)-phosphoramidite
Internal (base modified):
Amino-Modifier C6 dT
5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite. CAS Number: 178925-21-8

Solution phase conjugations may occur after oligonucleotide synthesis via reactions between non-nucleosidic nucleophilic functional groups that are attached to the oligonucleotide and electrophilic GalNAc reagents. Examples of nucleophilic groups include amines and thiols, and examples of electrophilic reagents include activated esters (e.g. N-hydroxysuccinimide, pentafluorophenyl) and maleimides.

Example 9: Inhibition of ANGPTL4 in a Mouse Model of Hypertriglyceridemia

In this experiment, a murine model of hypertriglyceridemia is to be used to evaluate the effect of siRNA or ASO inhibition of ANGPTL4 expressed in the liver compared to an anti-mouse ANGPTL4 antibody. The mouse strain C57Bl/6 Apoetm1Unc mice (Jackson Labs) will be maintained on a high fat Western diet (Research Diets, D12492; 60% fat by calories).

Four groups of mice (n=12/group) will be utilized in this study. Animals will be maintained on a high fat diet during the study. On Day −4 before the first injection, chow will be removed for an overnight fast. On Day −3 before the first injection, all animals will be anesthetized and 300 uL of blood collected in serum separator tubes via the submandibular vein to assess baseline triglyceride, serum glucose, insulin sensitivity, total cholesterol levels, HDL Cholesterol levels, liver function and serum levels of ANGPTL4 protein. On Study Day 0, Group 1 mice will be injected intraperitoneally with 600 uL normal saline, Group 2 mice will be injected intraperitoneally with 600 ug of anti-mouse ANGPTL4 antibody in 600 uL, Group 3 mice will be injected subcutaneously with 100 ug of GalNAc-ANGPTL4 siRNA targeting mouse ANGPTL4 with sense strand selected from sequences provided in SEQ ID NO: 13937-13944, 14289, or 14291, and antisense strands selected from sequences provided in SEQ ID NO: 13945-13952, 14290, or 14292, in 200 uL of normal saline, and Group 4 mice will be injected subcutaneously with 150 ug of GalNAc-ANGPTL4 ASO targeting mouse ANGPTL4 in 200 uL of normal saline. The sense strands selected from sequences provided in SEQ ID NO: 13937-13944, 14289, or 14291 will comprise a GalNAc ligand attached to the 3' end of the sense strands. On the afternoon of Day 3, the chow will be removed from all Groups for an overnight fast. On Day 4, the animals from all Groups will be anesthetized and 150 uL of blood collected in serum separator tubes via the submandibular vein to assess serum triglycerides, glucose, total cholesterol, HDL cholesterol and levels of ANGPTL4 protein. Animals from all groups will then undergo an oral glucose tolerance test and insulin tolerance test to evaluate insulin sensitivity. Chow will be supplied again as normal after blood has been collected and insulin sensitivity tests conducted. Weekly thereafter starting on Day 7 the animals from Group 2 will be dosed as on Day 0 for a total of 15 injections. Every other week thereafter starting on Day 14 the animals from Group 3 and Group 4 will be dosed as on Day 0 for a total of 8 injections. Every other week starting on Day 10, the mice from all Groups will be fasted (overnight) and bled (150 uL into serum separator tubes) to assess serum triglyceride, glucose, total cholesterol, HDL cholesterol and levels of ANGPTL4 protein, and undergo insulin sensitivity tests. On the third day after the final injection, the chow will be removed from all Groups for an overnight fast. On the fourth day after the final injection, the animals from all Groups will be anesthetized, euthanized and bled via cardiac puncture to collect 500 uL of blood into serum separator tubes to assess triglyceride, serum glucose, insulin sensitivity, total cholesterol levels, HDL cholesterol levels, liver function and serum levels of ANGPTL4 protein. Tissue from the liver, small intestine and mesenteric lymph nodes will be collected from all animals and immersed in 10% neutral buffered formalin for histopathological analysis. A liver sample will also be collected from all animals and placed in RNAlater. The levels of ANGPTL4 mRNA will be assessed by RT-qPCR using TaqMan assays for mouse ANGPTL4 (ThermoFisher, assay #Mm00480431_m1) and the mouse housekeeping gene PPIA (ThermoFisher, assay #Mm02342430_g1).

Animals treated with the anti-mouse ANGPTL4 antibody (Group 2), mice treated with GalNAc-ANGPTL4 siRNA (Group 3), and mice treated with GalNAc-ANGPTL4 ASO (Group 4) are expected to have decreased triglycerides, total serum cholesterol, serum glucose as well as decreased serum ANGPTL4 protein levels, and increased HDL cholesterol and insulin sensitivity, compared with mice from Group 1 (saline). Animals in Group 2 and Group 3 are also expected to have decreased ANGPTL4 mRNA in liver samples.

Example 10: Inhibition of ANGPTL4 in Non-Human Primates Using GalNAc-ANGPTL4 siRNA and GalNAc-ANGPTL4 ASO In this experiment, a NHP model of hypertriglyceridemia is used to evaluate the effect of siRNA or ASO inhibition of ANGPTL4 expressed in the liver. Three groups of cynomolgus monkeys will be used (n=5/group) that are placed on a high-fat diet (Western Primate Diet, 5S2T) before the initiation of the study. Alternatively, three groups of rhesus monkeys will be used (n=5/group) that are placed on a high fructose diet before the initiation of the study. Animals are to be given 7 biweekly subcutaneous injections of saline (Group 1), GalNAc-ANGPTL4 siRNA (Group 2), or GalNAc-ANGPTL4 ASO (Group 3). The modified GalNAc-ANGPTL4 siRNA sequences are chosen from subset A that are cross-reactive between human and NHP, and include modification pattern 1S, 2S or 3S and 1AS or 3AS. Other GalNAc-ANGPTL4 siRNA sequences may be chosen from subset F that are cross-reactive between human and NHP, or modifications thereof. Blood samples for lipid and glycemic measurements will be collected at baseline and at 4, 8, and 14 weeks of the study and analyzed for lipid content, serum glucose, insulin sensitivity and ANGPTL4 protein. All animals from each group are necropsied 2 weeks after the last blood collection. Tissue from the liver, small intestine and mesenteric lymph nodes will be collected from all animals and immersed in 10% neutral buffered formalin for histopathological analysis. A liver sample will also be collected from all animals and placed in RNAlater. The levels of ANGPTL4 mRNA will be assessed by RT-qPCR using TaqMan assays for cynomolgus ANGPTL4 (ThermoFisher, assay #Mf01101127_m1) or rhesus ANGPTL4, and the cynomolgus housekeeping gene PPIA (ThermoFisher, assay #Mf04932064_gH) or rhesus PPIA.

It is expected that animals treated with the GalNAc ANGPTL4 siRNA (Group 2) and animals treated with GalNAc-ANGPTL4 ASO (Group 3) will show decreased triglycerides, total serum cholesterol and serum glucose as well as decreased serum ANGPTL4 protein levels, and increased HDL cholesterol and insulin sensitivity, compared with animals from Group 1 (saline). It is also expected that animals in Group 1 and Group 3 will show decreased ANGPTL4 mRNA in liver samples.

Example 11: Inhibition of ANGPTL4 in a Clinical Trial Using GalNAc-ANGPTL4 siRNA and GalNAc-ANGPTL4 ASO In this study, human subjects with hypertriglyceridemia are used to evaluate the effect of siRNA or ASO inhibition of ANGPTL4 expressed in the liver. Selection criteria for inclusion in the study are ages 40-90, BMI≥30, and serum triglycerides≥250 mg/dL. Three groups of subjects will be included (n=15/group) in the study. Subjects are to be given 5 weekly subcutaneous injections of saline (Group 1), GalNAc-ANGPTL4 siRNA (Group 2), or GalNAc-ANGPTL4 ASO (Group 3). The modified GalNAc-ANGPTL4 siRNA sequences are chosen from subset A that show high activity in cells in culture in the experiments of Example 4. Blood samples for lipid and glycemic measurements will be collected at baseline and at 3, 6, and 12 weeks of the study and analyzed for lipid content, serum glucose, insulin sensitivity, ANGPTL4 protein, and liver and kidney function.

It is expected that subjects treated with the GalNAc ANGPTL4 siRNA (Group 2) and subjects treated with GalNAc-ANGPTL4 ASO (Group 3) will show decreased triglycerides, total serum cholesterol and serum glucose as well as decreased serum ANGPTL4 protein levels, and increased HDL cholesterol and insulin sensitivity, compared with subjects from Group 1 (saline).

Example 12: siRNA-Mediated Knockdown of ANGPTL4 in a Mouse Model of Hypertriglyceridemia The effects of siRNA-mediated knockdown of ANGPTL4 in the liver was investigated in a murine model of hypertriglyceridemia. Eight- to ten-week-old C57Bl/6 Apoetm1Unc mice (Jackson Labs) were placed on a high fat Western diet (Research Diets, D12492; 60% fat by calories) for two weeks prior to the start of the study on Day 0. On Day 0 and Day 7, mice in Group 1 (n=4) were given 200 uL of phosphate buffered saline (PBS) and mice in Group 2 (n=4) were given 200 ug of the siRNA targeting mouse ANGPTL4 (ETD00642: sense strand having the sequence of SEQ ID NO: 13941 and a 3' conjugated GalNAc ligand, and antisense strand having the sequence of SEQ ID NO: 13949) in 200 uL PBS by subcutaneous injection. Serum samples were collected from all mice fed ad libidum on Day 13. On Day 14, serum samples were collected from all mice after a 24 hour fast. Clinical chemistry assays including those for triglyceride and glucose were performed at IDEXX Laboratories, Incorporated. All mice were then euthanized and a liver sample from each was collected and placed in RNAlater (ThermoFisher Cat #AM7020). Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. The levels of liver ANGPTL4 mRNA were assessed by RT-qPCR using TaqMan assays for mouse ANGPTL4 (ThermoFisher, assay #Mm00480431_m1) and the mouse housekeeping gene PPIA (ThermoFisher, assay #Mm02342430_g1). Data were normalized to the level in animals receiving PBS (Group 1). Results are shown in Table 12. Mice receiving ETD00642 (Group2) had reduced levels of liver ANGPTL4 mRNA compared to mice receiving PBS (Group 1).

TABLE 12

Day 14 ANGPTL4 mRNA Levels in Mice Treated with ETD00642

| Group # | Animal # | Relative Liver ANGPTL4 mRNA Level | Mean Relative Liver ANGPTL4 mRNA level |
|---|---|---|---|
| 1 | 1 | 1.30 | 1.00 |
|   | 2 | 0.95 |  |
|   | 3 | 1.11 |  |
|   | 4 | 0.73 |  |
| 2 | 5 | 0.48 | 0.47 |
|   | 6 | 0.55 |  |
|   | 7 | 0.51 |  |
|   | 8 | 0.36 |  |

The levels of triglycerides and glucose are shown in Table 13. The serum triglyceride levels in fed mice on Day 13 and fasted mice on Day 14 were lower in mice receiving ETD00642 (Group 2) than in control mice receiving PBS (Group1). The serum glucose levels in fed mice on Day 13 were lower in mice receiving ETD00642 (Group 2) than in control mice receiving PBS (Group1). The serum glucose levels in fasted mice on Day 14 were also lower in mice receiving ETD00642 (Group 2) than in control mice receiving PBS (Group1), but the difference between Groups was less than that in the fasted mice.

TABLE 13

Triglyceride and Glucose Levels in Mice Treated with ETD00642

| | | Triglycerides (mg/dL) | | | | Glucose (mg/dL) | | | |
|---|---|---|---|---|---|---|---|---|---|
| | | Fed (Day 13) | | Fasted (Day 14) | | Fed (Day 13) | | Fasted (Day 14) | |
| Group # | Animal # | individual | Mean | individual | Mean | individual | Mean | individual | Mean |
| 1 | 1 | 180 | 201 | 119 | 117 | 297 | 296 | 129 | 103 |
|   | 2 | 213 |     | 135 |     | 300 |     | 110 |     |
|   | 3 | 193 |     | 99  |     | 305 |     | 91  |     |
|   | 4 | 217 |     | 113 |     | 280 |     | 80  |     |
| 2 | 5 | 148 | 140 | 65  | 69  | 210 | 202 | 97  | 89  |
|   | 6 | 158 |     | 66  |     | 218 |     | 100 |     |
|   | 7 | 66  |     | 61  |     | 221 |     | 76  |     |
|   | 8 | 186 |     | 85  |     | 158 |     | 83  |     |

Example 13: Activity of siRNAs Targeting ANGPTL4 in Non-Human Primates

The activity of four siRNAs targeting ANGPTL4 were tested individually in cynomolgus monkeys. The siRNAs utilized in this study included ETD01117, ETD01118, ETD01119, and ETD01120 (see Table 16 for siRNA details).

Female cynomolgus monkeys (*Macaca fascicularis*, Cambodian origin, Orient BioResource Center, Alice, Tex.) were at least 18 months of age and weighed 2.5-3 kg at study start. After arrival, the animals were pair housed in stainless steel cages suspended over flush pans. Fluorescent lighting on a 12 hour on/off cycle was used and the temperature maintained at 18-29□ C. at a target relative humidity of 30-70% with at least 10-15 air exchanges per hour. Animals were acclimated for a period of at least twenty-eight days, during which time they were examined for overall general health and observed daily. Animals were limit fed daily with certified primate diet (5048). Tap water was provided ad libitum.

Monkeys (3/group) were administered the siRNA test article once on Day 0 by subcutaneous injection as described in Table 14. In-life, animals were evaluated for clinical signs of toxicity, body weights, and food consumption. Prior to and during the study evaluations for clinical chemistry parameters were performed.

TABLE 14 siRNA Dosing Information

| Group | siRNA | Dosage (mg/kg) | Conc. (mg/mL) | Animal No. |
|---|---|---|---|---|
| 1 | ETD01117 | 5 | 50 | 1-3 |
| 2 | ETD01118 | 5 | 50 | 4-6 |
| 3 | ETD01119 | 5 | 50 | 7-9 |
| 4 | ETD01120 | 5 | 50 | 10-12 |

Whole blood (approximately 2-3 mL) was collected from fasted animals twice prior to first dose (Day −7 and −2), and from surviving animals on Days 7, 14. Whole blood (approximately 2-3 mL) was collected from non-fasted animals once prior to dosing (Day −8). Blood samples were analyzed for clinical chemistry parameters, processed to serum for measurement of ANGPTL4 levels, and processed to plasma for lipoprotein profile assay.

An AlphaLISA immunoassay (PerkinElmer AL3017) was used to measure serum ANGPTL4 levels according to the recommended protocols provided by the manufacturer. Briefly, standard analyte (recombinant human ANGPTL4 encoding residues Gly26-Ser406) and serum samples were prepared in 1× AlphaLISA Assay Buffer (PerkinElmer AL000C). For each assay, 5 µL of prepared standard analyte or diluted sample were added to a 96-well white ½ Area OptiPlate (PerkinElmer 6002290) followed by the addition of 10 µL of Acceptor bead mix. Then the plate was sealed with TopSeal A-PLUS (PerkinElmer 6050185) and incubated for 30 minutes at room temperature. Next, 10 µL of biotinylated antibody was added to each well of the plate. The plate was sealed and incubated for 60 minutes at room temperature. Afterwards, 25 µL of streptavidin Donor beads were added in the dark to prevent photobleaching. The plate was sealed, covered with foil, and incubated at room temperature for 30 minutes prior to measuring AlphaLISA signal. All Alpha assays were measured on the Alpha-enabled EnVision multilabel plate reader using the 640 as mirror module (#444) and the M570w emission filter (#244). Standard Alpha measurement settings were used: excitation wavelength at 680 nm was used to excite Donor beads and emission wavelength at 615 nm measured as Alpha signal; total measurement time 550 ms and excitation time 180 ms were used. A standard curve was generated by plotting the Alpha signal counts versus the concentration of analyte using GraphPad Prism version 9 for macOS (GraphPad Software). The curve was fit according to a nonlinear regression using the 4-parameter logistic equation (sigmoidal dose-response curve with variable slope) and a 1/Y2 data weighting. Signal for samples was converted to pg/mL from interpolation of the standard curve from each plate and corrected for dilution of sample prior to assay. The results are shown in Table 15. Results indicate that after treatment with siRNAs targeting ANGPTL4 the mean levels of ANGPTL4 protein in serum were reduced. In addition, mean levels of serum ANGPTL4 protein levels were lower in fed animals than in fasted animals.

TABLE 15

Serum ANGPTL4 Protein Levels in Non-Human Primates Treated with ANGPTL4 siRNAs

| Group # (n = 3) | siRNA | Day | Group Means* |
|---|---|---|---|
| 1 | ETD01117 | −8 (fed) | 0.66 |
| | | −7 | 0.97 |
| | | −2 | 1.03 |
| | | 7 | 0.66 |
| | | 14 | 0.38 |
| 2 | ETD01118 | −8 (fed) | 0.68 |
| | | −7 | 1.10 |
| | | −2 | 0.90 |
| | | 7 | 0.61 |
| | | 14 | 0.68 |
| 3 | ETD01119 | −8 (fed) | 0.73 |
| | | −7 | 1.07 |
| | | −2 | 0.93 |
| | | 7 | 0.50 |
| | | 14 | 0.65 |
| 4 | ETD01120 | −8 (fed) | 0.49 |
| | | −7 | 0.94 |
| | | −2 | 1.06 |
| | | 7 | 0.52 |
| | | 14 | 0.52 |

*relative to the mean of Day −7 and Day −2 values in each group

Example 14: siRNAs Targeting ANGPTL4

Some non-limiting examples of siRNAs have one or more characteristics of the siRNAs in Table 16.

TABLE 16

Exemplary modified siRNAs

| siRNA Name | Sense Strand Sequence SEQ ID NO: | Additional Characteristic of Sense Strand | Antisense Strand Sequence - SEQ ID NO: |
|---|---|---|---|
| ETD01062 | 13986 | — | 14134 |
| ETD01063 | 13987 | — | 14135 |
| ETD01064 | 13988 | — | 14136 |
| ETD01065 | 13989 | — | 14137 |
| ETD01117 | 13990 | GalNAc#23 conjugated at 3' end | 14134 |
| ETD01118 | 13991 | GalNAc#23 conjugated at 3' end | 14135 |
| ETD01119 | 13992 | GalNAc#23 conjugated at 3' end | 14136 |
| ETD01120 | 13993 | GalNAc#23 conjugated at 3' end | 14137 |
| ETD01117.1 | 13994 | GalNAc ligand conjugated at 5' end | 14134 |
| ETD01118.1 | 13995 | GalNAc ligand conjugated at 5' end | 14135 |
| ETD01119.1 | 13996 | GalNAc ligand conjugated at 5' end | 14136 |
| ETD01120.1 | 13997 | GalNAc ligand conjugated at 5' end | 14137 |
| ETD01117.2 | 13998 | GalNAc ligand conjugated at 5' end | 14134 |

TABLE 16-continued

Exemplary modified siRNAs

| siRNA Name | Sense Strand Sequence SEQ ID NO | Additional Characteristic of Sense Strand | Antisense Strand Sequence - SEQ ID NO: |
|---|---|---|---|
| ETD01118.2 | 13999 | GalNAc ligand conjugated at 5' end | 14135 |
| ETD01119.2 | 14000 | GalNAc ligand conjugated at 5' end | 14136 |
| ETD01120.2 | 14001 | GalNAc ligand conjugated at 5' end | 14137 |
| ETD01117.3 | 14006 | GalNAc ligand conjugated at 5' end | 14138 |
| ETD01118.3 | 14007 | GalNAc ligand conjugated at 5' end | 14139 |
| ETD01119.3 | 14008 | GalNAc ligand conjugated at 5' end | 14140 |
| ETD01120.3 | 14009 | GalNAc ligand conjugated at 5' end | 14141 |
| ETD01117.4 | 14006 | GalNAc ligand conjugated at 5' end | 14142 |
| ETD01118.4 | 14007 | GalNAc ligand conjugated at 5' end | 14143 |
| ETD01119.4 | 14008 | GalNAc ligand conjugated at 5' end | 14144 |
| ETD01120.4 | 14009 | GalNAc ligand conjugated at 5' end | 14145 |
| ETD01117.5 | 14006 | GalNAc ligand conjugated at 5' end | 14146 |
| ETD01118.5 | 14007 | GalNAc ligand conjugated at 5' end | 14147 |
| ETD01119.5 | 14008 | GalNAc ligand conjugated at 5' end | 14148 |
| ETD01120.5 | 14009 | GalNAc ligand conjugated at 5' end | 14149 |
| ETD01117.6 | 14006 | GalNAc ligand conjugated at 5' end | 14150 |
| ETD01118.6 | 14007 | GalNAc ligand conjugated at 5' end | 14151 |
| ETD01119.6 | 14008 | GalNAc ligand conjugated at 5' end | 14152 |
| ETD01120.6 | 14009 | GalNAc ligand conjugated at 5' end | 14153 |
| ETD01117.7 | 14002 | GalNAc ligand conjugated at 5' end | 14154 |
| ETD01118.7 | 14003 | GalNAc ligand conjugated at 5' end | 14155 |
| ETD01119.7 | 14004 | GalNAc ligand conjugated at 5' end | 14156 |
| ETD01120.7 | 14005 | GalNAc ligand conjugated at 5' end | 14157 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11377658B2). An electronic copy of the "Sequence Listing" will also be available from the USPTO upon request and payment of the fee set forth in 37 CFR 1.19(b)(3).

We claim:

1. A composition comprising an oligonucleotide that targets Angiopoietin like 4 (ANGPTL4) and when administered to a cell decreases expression of ANGPTL4; wherein the oligonucleotide comprises a small interfering RNA (siRNA) comprising a sense strand and an antisense strand, wherein the sense strand comprises an oligonucleotide sequence of any of SEQ ID NOS: 13971-13973 or 13975-13977 in which at least one internucleoside linkage is modified and at least one nucleoside is modified, or an oligonucleotide sequence comprising 1 or 2 nucleoside substitutions, additions, or deletions of any of 13971-13973 or 13975-13977 in which at least one internucleoside linkage is modified and at least one nucleoside is modified; and wherein the antisense strand comprises an oligonucleotide sequence of any of SEQ ID NOS: 13979-13981 or 13983-13985 in which at least one internucleoside linkage is modified and at least one nucleoside is modified, or an oligonucleotide sequence comprising 1 or 2 nucleoside substitutions, additions, or deletions of any of SEQ ID NOS:

13979-13981 or 13983-13985 in which at least one internucleoside linkage is modified and at least one nucleoside is modified.

2. The composition of claim 1, wherein the at least one nucleoside is modified comprises a 2'-fluoro modified nucleoside.

3. The composition of claim 1, wherein the at least one nucleoside is modified comprises a 2'-O-methyl modified nucleoside.

4. The composition of claim 1, wherein the oligonucleotide comprises 15-23 modified nucleosides.

5. The composition of claim 4, wherein the 15-23 modified nucleosides comprises 2'-fluoro modified nucleosides and 2'-O-methyl modified nucleosides.

6. The composition of claim 1, wherein the at least one internucleoside linkage is modified comprises a phosphorothioate linkage.

7. The composition of claim 1, wherein the oligonucleotide comprises a GalNAc ligand attached to the oligonucleotide.

8. The composition of claim 7, wherein the GalNAc ligand comprises 3 GalNAc moieties.

9. The composition of claim 7, wherein the GalNAc ligand attached to the oligonucleotide comprises a GalNAc ligand attached at a 5' or 3' terminus of the sense strand.

10. The composition of claim 1, wherein the antisense strand comprises the nucleoside sequence of any of SEQ ID NOS: 13979-13981 or 13983-13985, and wherein the sense strand comprises the nucleoside sequence of any of SEQ ID NOS: 13971-13973 or 13975-13977.

11. The composition of claim 1, wherein the sense strand or the antisense strand comprises a 3' overhang.

12. A composition comprising an oligonucleotide that targets Angiopoietin like 4 (ANGPTL4) and when administered to a cell decreases expression of ANGPTL4; wherein the oligonucleotide comprises a small interfering RNA (siRNA) comprising a sense strand and an antisense strand, wherein the sense strand comprises an oligonucleotide sequence of any of SEQ ID NOS: 13970-13977 in which at least one internucleoside linkage is modified and at least one nucleoside is modified, or an oligonucleotide sequence comprising 1 or 2 nucleoside substitutions, additions, or deletions of any of SEQ ID NOS: 13970-13977 in which at least one internucleoside linkage is modified and at least one nucleoside is modified; wherein the antisense strand comprises an oligonucleotide sequence of any of SEQ ID NOS: 13978-13985 in which at least one internucleoside linkage is modified and at least one nucleoside is modified, or an oligonucleotide sequence comprising 1 or 2 nucleoside substitutions, additions, or deletions of any of SEQ ID NOS: 13978-13985 in which at least one internucleoside linkage is modified and at least one nucleoside is modified; and
  wherein the sense strand or the antisense strand comprises one of the following modification patterns:
  5'-NfsnsNfnNfnNfNfNfnNfnNfnNfnNfnNfsnsn-3' (SEQ ID NO: 13954), 5'-nsnsnnNfnNfNf NfnnnnnnnnnnsnsN-3' (SEQ ID NO: 13955), 5'-nsnsnnNfnNfnNfnnnnnnnnnnnsnsn-3' (SEQ ID NO: 13956), 5'-NfsnsNfnNfnNfNfNfnNfnNfnNfn NfnNfs nsnN-3' (SEQ ID NO: 13957), 5'-nsnsnnNfnNfNfNfnn nnnnnnnnnsnsN-3' (SEQ ID NO: 13958), 5'-NfsnsN fnNfnNfnNfnNfnNfnNfnNfnNfnNfsnsn-3' (SEQ ID NO: 13959), 5'-nsNfsnNfnNfnNfnNfnnnNfnNfnNfnsnsn-3' (SEQ ID NO: 13960), 5'-nsNfsnnnNfnNf NfnnnnNfnNfnnnsnsn-3' (SEQ ID NO: 13961), 5'-nsNfsnnnNfnnnnnnnnNfnNfnnnsnsn-3' (SEQ ID NO: 13962), 5'-nsNfsnNfnNfnnnnnnnnNfnNfnnnsnsn-3' (SEQ ID NO: 13963), 5'-nsNfsnnnNfn NfnnnnnNfnNfnnnsnsn-3' (SEQ ID NO: 13964), 5'-nsNfsnNfnNfnNfnNfnNfnNfnNfnNfsnsn-3' (SEQ ID NO: 13965), 5'-nsNfsnNfnNfnNfNf nnnnNfnNfnnnsnsn-3' (SEQ ID NO: 13966), 5'-nsNfsnnnnnnnnnnNfnnnnnnsnsn-3' (SEQ ID NO: 13967), or 5'-nsNfsnnnNfnnnnnnnnNfnNfnNfnsnsn-3' (SEQ ID NO: 13968), wherein "N" comprises one or more nucleosides, "Nf" is a 2' fluoro-modified nucleoside, "n" is a 2' O-methyl modified nucleoside, and "s" is a phosphorothioate linkage.

13. The composition of claim 1, wherein the sense strand comprises the nucleoside sequence of any of SEQ ID NOS: 13973 or a sense strand sequence thereof having 1 or 2 nucleoside substitutions, additions, or deletions; and wherein the antisense strand comprises the nucleoside sequence of SEQ ID NO: 13981 or an antisense strand sequence thereof having 1 or 2 nucleoside substitutions, additions, or deletions.

14. The composition of claim 1, wherein the sense strand comprises the nucleoside sequence of SEQ ID NO: 13977, and wherein the antisense strand comprises the nucleoside sequence of SEQ ID NO: 13985.

15. The composition of claim 14, wherein the sense strand comprises modification pattern 2S: 5'-nsnsnnNfnN fNfNfnnnnnnnnnnnsnsn-3' (SEQ ID NO: 13955), and wherein the antisense strand comprises modification pattern 3AS: 5'-nsNfsnnnNfnnnnnnnnNfnNfnnnsnsn-3' (SEQ ID NO: 13962), wherein "Nf" is a 2' fluoro-modified nucleoside, "n" is a 2' O-methyl modified nucleoside, and "s" is a phosphorothioate linkage.

16. The composition of claim 15, wherein the oligonucleotide comprises a GalNAc ligand attached at a 3' end of the sense strand.

17. The composition of claim 14, wherein the sense strand comprises modification pattern 6S: 5'-NfsnsNfn NfnNfnNfnNfnNfnNfnNfnNfsnsn-3' (SEQ ID NO: 13959), wherein "Nf" is a 2' fluoro-modified nucleoside, "n" is a 2' O-methyl modified nucleoside, and "s" is a phosphorothioate linkage.

18. The composition of claim 17, wherein the oligonucleotide comprises a GalNAc ligand attached at a 5' end of the sense strand.

19. The composition of claim 17, wherein the oligonucleotide comprises a GalNAc ligand attached at a 3' end of the sense strand.

20. The composition of claim 17, wherein the antisense strand comprises modification pattern 6AS: 5'-nsNfsnNfn NfnNfnNfnNfnNfnNfnNfnsnsn-3' (SEQ ID NO: 13965), or 8AS: 5'-nsNfsnnnnnnnnnnNfnnnnnsnsn-3' (SEQ ID NO: 13967), wherein "Nf" is a 2' fluoro-modified nucleoside, "n" is a 2' O-methyl modified nucleoside, and "s" is a phosphorothioate linkage.

* * * * *